US009492508B2

(12) United States Patent
Gardella et al.

(10) Patent No.: US 9,492,508 B2
(45) Date of Patent: Nov. 15, 2016

(54) PARATHYROID HORMONE ANALOGS AND USES THEREOF

(75) Inventors: Thomas J. Gardella, Needham, MA (US); John T. Potts, Jr., Newton, MA (US); Harald Jueppner, Lexington, MA (US); Makoto Okazaki, Tokyo (JP)

(73) Assignees: The General Hospital Corporation, Boston, MA (US); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/697,249

(22) PCT Filed: May 12, 2011

(86) PCT No.: PCT/US2011/036222
§ 371 (c)(1),
(2), (4) Date: Jan. 22, 2013

(87) PCT Pub. No.: WO2011/143406
PCT Pub. Date: Nov. 17, 2011

(65) Prior Publication Data
US 2013/0116180 A1  May 9, 2013

Related U.S. Application Data

(60) Provisional application No. 61/334,319, filed on May 13, 2010, provisional application No. 61/415,141, filed on Nov. 18, 2010.

(51) Int. Cl.
A61K 38/29 (2006.01)
C07K 14/635 (2006.01)

(52) U.S. Cl.
CPC ............. *A61K 38/29* (2013.01); *C07K 14/635* (2013.01)

(58) Field of Classification Search
None
See application file for complete search history.

(56) References Cited

U.S. PATENT DOCUMENTS

| | | |
|---|---|---|
| 4,086,196 A | 4/1978 | Tregear |
| 4,366,241 A | 12/1982 | Tom et al. |
| 4,423,037 A | 12/1983 | Rosenblatt et al. |
| 4,511,502 A | 4/1985 | Builder et al. |
| 4,512,922 A | 4/1985 | Jones et al. |
| 4,518,526 A | 5/1985 | Olson |
| 4,620,948 A | 11/1986 | Builder et al. |
| 4,675,189 A | 6/1987 | Kent et al. |
| 4,698,328 A | 10/1987 | Neer et al. |
| 4,736,866 A | 4/1988 | Leder et al. |
| 4,761,406 A | 8/1988 | Flora et al. |
| 4,771,124 A | 9/1988 | Rosenblatt et al. |
| 4,843,000 A | 6/1989 | Litman et al. |
| 4,849,338 A | 7/1989 | Litman et al. |
| 5,010,010 A | 4/1991 | Gautvik et al. |
| 5,208,041 A | 5/1993 | Sindrey |
| 5,217,896 A | 6/1993 | Kramer et al. |
| 5,227,487 A | 7/1993 | Haugland et al. |
| 5,274,113 A | 12/1993 | Kang et al. |
| 5,326,692 A | 7/1994 | Brinkley et al. |
| 5,350,836 A | 9/1994 | Kopchick et al. |
| 5,382,658 A | 1/1995 | Kronis et al. |
| 5,393,869 A | 2/1995 | Nakagawa et al. |
| 5,405,975 A | 4/1995 | Kuhn et al. |
| 5,433,896 A | 7/1995 | Kang et al. |
| 5,442,045 A | 8/1995 | Haugland et al. |
| 5,451,663 A | 9/1995 | Kang et al. |
| 5,453,517 A | 9/1995 | Kuhn et al. |
| 5,457,034 A | 10/1995 | della Valle et al. |
| 5,459,276 A | 10/1995 | Kuhn et al. |
| 5,462,856 A | 10/1995 | Lerner et al. |
| 5,494,806 A | 2/1996 | Segre et al. |
| 5,496,801 A | 3/1996 | Holthuis et al. |
| 5,501,979 A | 3/1996 | Geller et al. |
| 5,516,864 A | 5/1996 | Kuhn et al. |
| 5,527,772 A | 6/1996 | Holick |
| 5,556,940 A | 9/1996 | Willick et al. |
| 5,573,909 A | 11/1996 | Singer et al. |
| 5,578,461 A | 11/1996 | Sherwin et al. |
| 5,589,452 A | 12/1996 | Krstenansky et al. |
| 5,605,815 A | 2/1997 | Broadus et al. |
| 5,616,560 A | 4/1997 | Geddes et al. |
| 5,648,270 A | 7/1997 | Kuhn et al. |
| 5,656,465 A | 8/1997 | Panicali et al. |
| 5,693,616 A | 12/1997 | Krstenansky et al. |

(Continued)

FOREIGN PATENT DOCUMENTS

| | | |
|---|---|---|
| AU | 668118 B2 | 4/1996 |
| CA | 2126132 A1 | 12/1995 |

(Continued)

OTHER PUBLICATIONS

Shimizu, Naoto et al; "Parathyroid hormone (PTH)-(1-14) and -_1-11) analogs conformationally constrained by alpha aminoisobutyric acid mediate full agonist responses via the juxtamembrane region of the PTH-1 receptor." J. Biol. Chem. (2001) 276(52) p. 49003-49012.*

(Continued)

*Primary Examiner* — Maury Audet
*Assistant Examiner* — Fred Reynolds
(74) *Attorney, Agent, or Firm* — Clark & Elbing LLP

(57) ABSTRACT

Disclosed are two PTH analog ligands, SP-PTH-AAK and Aib-SP-PTH-AAK, that have long-acting activity at the PTH receptor, as demonstrated both in vitro and in vivo. These polypeptides are thus particularly useful in the treatment of diseases, such as hypoparathyroidism, in which long-acting activity is desired. The method of making the analog polypeptides is also disclosed.

10 Claims, 50 Drawing Sheets

(56) References Cited

U.S. PATENT DOCUMENTS

| | | |
|---|---|---|
| 5,695,955 A | 12/1997 | Krstenansky et al. |
| 5,717,062 A | 2/1998 | Chorev et al. |
| 5,723,218 A | 3/1998 | Haugland et al. |
| 5,723,577 A | 3/1998 | Dong |
| 5,741,486 A | 4/1998 | Pathak et al. |
| 5,763,416 A | 6/1998 | Bonadio et al. |
| 5,798,225 A | 8/1998 | Krstenansky et al. |
| 5,807,823 A | 9/1998 | Krstenansky et al. |
| 5,814,603 A * | 9/1998 | Oldenburg et al. ......... 514/11.8 |
| 5,821,225 A | 10/1998 | Vickery |
| 5,836,905 A | 11/1998 | Lemelson et al. |
| 5,840,690 A | 11/1998 | Holick |
| 5,840,837 A | 11/1998 | Krstenansky et al. |
| 5,840,853 A | 11/1998 | Segre et al. |
| 5,854,004 A | 12/1998 | Czernilofsky et al. |
| 5,871,486 A | 2/1999 | Huebner et al. |
| 5,874,086 A | 2/1999 | Krstenansky et al. |
| 5,880,093 A | 3/1999 | Bagnoli et al. |
| 5,886,148 A | 3/1999 | Segre et al. |
| 5,917,123 A | 6/1999 | McTiernan et al. |
| 5,922,927 A | 7/1999 | Bujard et al. |
| 5,969,095 A | 10/1999 | Dong |
| 5,977,070 A | 11/1999 | Piazza et al. |
| 6,030,790 A | 2/2000 | Adermann et al. |
| 6,051,686 A | 4/2000 | Krstenansky et al. |
| 6,066,618 A | 5/2000 | Holick |
| 6,147,186 A | 11/2000 | Gardella et al. |
| 6,183,974 B1 | 2/2001 | Bringhurst et al. |
| 6,362,163 B1 | 3/2002 | Gardella et al. |
| 6,417,333 B1 | 7/2002 | Bringhurst et al. |
| 6,495,662 B1 * | 12/2002 | Gardella et al. ............. 530/300 |
| 6,537,965 B1 | 3/2003 | Bringhurst et al. |
| 6,541,220 B1 | 4/2003 | Juppner et al. |
| 6,756,480 B2 | 6/2004 | Kostenuik et al. |
| 6,803,213 B2 | 10/2004 | Bringhurst et al. |
| 7,022,815 B1 | 4/2006 | Gardella et al. |
| 7,033,773 B1 | 4/2006 | Bringhurst et al. |
| 7,057,012 B1 | 6/2006 | Gardella et al. |
| 7,078,487 B2 | 7/2006 | Juppner et al. |
| 7,132,260 B2 | 11/2006 | Segre et al. |
| 7,150,974 B1 | 12/2006 | Segre et al. |
| 7,153,951 B2 | 12/2006 | Gardella et al. |
| 7,169,567 B1 | 1/2007 | Gardella et al. |
| 7,244,834 B2 | 7/2007 | Gardella et al. |
| 7,253,264 B1 | 8/2007 | Lauffer et al. |
| 7,371,844 B2 | 5/2008 | Gardella et al. |
| 7,479,478 B2 | 1/2009 | Bringhurst et al. |
| 7,521,528 B2 | 4/2009 | Gardella et al. |
| 7,572,765 B2 | 8/2009 | Gardella |
| 7,632,811 B2 | 12/2009 | Dong |
| 7,795,220 B2 | 9/2010 | Gardella et al. |
| 7,910,544 B2 | 3/2011 | Gardella et al. |
| 7,985,835 B2 | 7/2011 | Gardella et al. |
| 8,143,374 B2 | 3/2012 | Kronenberg et al. |
| 8,568,737 B2 | 10/2013 | Gardella et al. |
| 2002/0110871 A1 | 8/2002 | Zahradnik et al. |
| 2003/0144209 A1 | 7/2003 | Bringhurst et al. |
| 2003/0162256 A1 | 8/2003 | Juppner et al. |
| 2003/0166838 A1 | 9/2003 | Gardella et al. |
| 2003/0171288 A1 | 9/2003 | Stewart |
| 2004/0176285 A1 | 9/2004 | Juppner et al. |
| 2005/0026839 A1 | 2/2005 | Gardella |
| 2005/0124537 A1 | 6/2005 | Kostenuik et al. |
| 2005/0203012 A1 | 9/2005 | Bringhurst et al. |
| 2005/0282749 A1 | 12/2005 | Henriksen et al. |
| 2006/0078559 A1 | 4/2006 | Migeotte et al. |
| 2007/0111946 A1 | 5/2007 | Gardella et al. |
| 2007/0161569 A1 | 7/2007 | Gardella |
| 2007/0203071 A1 | 8/2007 | Gardella |
| 2008/0119401 A1 | 5/2008 | Dong |
| 2009/0264365 A1 | 10/2009 | Gardella et al. |
| 2010/0048462 A1 * | 2/2010 | Ryge et al. ......... 514/9 |
| 2011/0009328 A1 | 1/2011 | Gardella et al. |
| 2011/0172153 A1 | 7/2011 | Gardella et al. |

FOREIGN PATENT DOCUMENTS

| | | |
|---|---|---|
| CA | 2126299 A1 | 12/1995 |
| EP | 0 341 962 A2 | 11/1989 |
| EP | 0 464 533 A1 | 1/1992 |
| EP | 0 477 885 A2 | 4/1992 |
| EP | 0 561 412 A1 | 9/1993 |
| EP | 0 748 817 A2 | 12/1996 |
| EP | 0 783 522 A1 | 7/1997 |
| GB | 2 269 176 A | 2/1994 |
| JP | 58096052 A | 6/1983 |
| JP | 59204159 A | 11/1984 |
| JP | 5-32696 A | 2/1993 |
| JP | 9-157294 A | 6/1997 |
| JP | 11-509201 | 8/1999 |
| WO | WO-87/01130 A1 | 2/1987 |
| WO | WO-91/05050 A1 | 4/1991 |
| WO | WO-92/01810 A1 | 2/1992 |
| WO | WO-92/17581 A1 | 10/1992 |
| WO | WO-92/17602 A1 | 10/1992 |
| WO | WO-93/06121 A1 | 4/1993 |
| WO | WO-93/06846 A1 | 4/1993 |
| WO | WO-93/09222 A2 | 5/1993 |
| WO | WO-93/11257 A2 | 6/1993 |
| WO | WO-94/02510 A2 | 2/1994 |
| WO | WO-94/12650 A2 | 6/1994 |
| WO | WO-95/02610 A1 | 1/1995 |
| WO | WO-95/11988 A1 | 5/1995 |
| WO | WO-96/03437 A1 | 2/1996 |
| WO | WO-96/10041 A1 | 4/1996 |
| WO | WO-96/19206 A1 | 6/1996 |
| WO | WO-97/02834 A1 | 1/1997 |
| WO | WO-98/04591 A1 | 2/1998 |
| WO | WO-98/05683 A1 | 2/1998 |
| WO | WO-98/30590 A2 | 7/1998 |
| WO | WO-99/18945 A1 | 4/1999 |
| WO | WO-99/57139 A2 | 11/1999 |
| WO | WO-00/23594 A1 | 4/2000 |
| WO | WO-00/31137 A1 | 6/2000 |
| WO | WO-00/31266 A1 | 6/2000 |
| WO | WO-00/32771 A1 | 6/2000 |
| WO | WO-00/32775 A1 | 6/2000 |
| WO | WO-00/39278 A2 | 7/2000 |
| WO | WO-00/40698 A1 | 7/2000 |
| WO | WO-01/23427 A1 | 4/2001 |
| WO | WO-01/23521 A2 | 4/2001 |
| WO | WO-03/009804 A2 | 2/2003 |
| WO | WO-2004/067021 A1 | 8/2004 |
| WO | WO-2004/093902 A1 | 11/2004 |
| WO | WO-2005/009358 A2 | 2/2005 |
| WO | WO-2006/033912 A2 | 3/2006 |
| WO | WO-2008/019062 A2 | 2/2008 |
| WO | WO-2009/017809 A2 | 2/2009 |
| WO | WO 2009017809 A2 * | 2/2009 |
| WO | WO-2011/143406 A2 | 11/2011 |

OTHER PUBLICATIONS

SigmaAldrich product sheet for l-histidine monohydrochloride, product No. H5659, published Mar. 2007.*

Chen, Liang et al, "The role of surface charge on the uptake and biocompatibility of hydroxyapatite nanoparticles with osteoblast cells." Nanotechnology (2011) 22(10) p. 1-20.*

The GE product literature for Biacore affinity determination equipment http://www.iqm.csic.es/wp-content/uploads/2013/equipamiento/spr/DD%20Toolbox%20-%20Characterization_GE.pdf, downloaded Aug. 13, 2015.*

Burk, Dan L. and Lemley, Mark A., "The patent crisis and how the courts can solve it" (2009) ISBN 97-0-226-08061-1.*

The Prentice Hall webpage http://wps.prenhall.com/wps/media/objects/3312/3392202/blb1705.html, available online Dec. 2007.*

Shimizu et al., "A new long-acting PTH/PTHrP hybrid analog that binds to a distinct PTHR conformation has superior efficacy in a rat model of hypoparathyroidism," J. Bone Min Res. 23:S128 (2008). Abstract F483.

Extended European Search Report and Search Opinion for European Application No. 11781266.9, dated Oct. 28, 2013 (5 pages).

(56) References Cited

OTHER PUBLICATIONS

Chorev et al., "Modifications of position 12 in parathyroid hormone and parathyroid hormone related protein: toward the design of highly potent antagonists," Biochemistry. 29(6): 1580-1586 (1990).
Extended European Search Report for European Patent Application No. 13001965.6, dated Jan. 8, 2014 (10 pages).
Horwitz et al., "Short-term, high-dose parathyroid hormone-related protein as a skeletal anabolic agent for the treatment of postmenopausal osteoporosis," J Clin Endocrinol Metab. 88(2):569-75 (2003).
International Preliminary Report on Patentability for PCT/US2008/009288, issued Feb. 2, 2010 (10 pages).
International Search Report and Written Opinion for PCT/US2008/009288, mailed Mar. 11, 2009 (15 pages).
Partial European Search Report for European Application No. 13001965.6, mailed Sep. 5, 2013 (6 pages).
Supplementary European Search Report for European Application No. 08794952.5, dated Sep. 29, 2010 (8 pages).
Tashjian et al., "Teriparatide [human PTH(1-34)]: 2.5 years of experience on the use and safety of the drug for the treatment of osteoporosis," J Bone Miner Res. 21(3):354-65 (2006).
Abou-Samra et al., "Phorbol 12-Myristate 13-Acetate and Vasopressin Potentiate the Effect of Corticotropin-Releasing Factor on Cyclic AMP Production in Rat Anterior Pituitary Cells. Mechanisms of Action," *J. Biol. Chem.* 262: 1129-1136 (1987).
Abou-Samra et al., "Non-Homologous Sequences of Parathyroid Hormone and the Parathyroid Hormone Related Peptide Bind to a Common Receptor on ROS 17/2.8 Cells," *Endocrinology* 125: 2215-2217 (1989).
Abou-Samra et al., "Cyclic Adenosine 3', 5'-Monophosphate (cAMP)-Dependent and cAMP-Independent Regulation of Parathyroid Hormone Receptors on UMR 106-01 Osteoblastic Osteosarcoma Cells," *Endocrinology* 129: 2547-2554 (1991).
Abou-Samra et al., "Expression Cloning of a Common Receptor for Parathyroid Hormone and Parathyroid Hormone-Related Peptide From Rat Osteoblast-Like Cells: A Single Receptor Stimulates Intracellular Accumulation of Both cAMP and Inositol Trisphosphates and Increases Intracellular Free Calcium," *Proc. Natl. Acad. Sci. USA* 89: 2732-2736 (1992).
Abou-Samra et al., "Down-Regulation of Parathyroid (PTH)/PTH-Related Peptide Receptor Immunoreactivity and PTH Binding in Opossum Kidney Cells by PTH and Dexamethasone," *Endocrinology* 135: 2588-2594 (1994).
Adams et al., "Probing the Bimolecular Interactions of Parathyroid Hormone and the Human Parathyroid Hormone/Parathyroid Hormone-Related Protein Receptor. 2. Cloning, Characterization, and Photoaffinity Labeling of the Recombinant Human Receptor," *Biochemistry* 34: 10553-10559 (1995).
Alberts et al., "Chapter 6: Basic Genetic Mechanisms" in: *Molecular Biology of the Cell*, 3rd Edition, pp. 234-237 and the Genetic Code Table (Garland Pub., New York, NY, 1994).
Azarani et al., "Parathyroid Hormone and Parathyroid Hormone-Related Peptide Activate the $Na^+/H^+$ Exchanger NHE-1 Isoform in Osteoblastic Cells (UMR-106) via a cAMP-dependent Pathway," *J. Biol. Chem.* 270: 23166-23172 (1995).
Azarani et al., "Structurally Diverse N-terminal Peptides of Parathyroid Hormone (PTH) and PTH-Related Peptide (PTHRP) Inhibit the Na+/H+ Exchanger NHE3 Isoform by Binding to the PTH/PTHRP Receptor Type I and Activating Distinct Signaling Pathways," *J. Biol. Chem.* 271: 14931-14936 (1996).
Barbier et al., "Bioactivities and Secondary Structures of Constrained Analogues of Human Parathyroid Hormone: Cyclic Lactams of the Receptor Binding Region," *J. Med. Chem.* 40: 1373-1380 (1997).
Barbier et al., "Structural Requirements for Conserved Arginine of Parathyroid Hormone," *Biochemistry* 40: 8955-8961 (2001).
Barbier et al., "Backbone-Methylated Analogues of the Principle Receptor Binding Region of Human Parathyroid Hormone. Evidence for Binding to Both the N-Terminal Extracellular Domain and Extracellular Loop Region," *J. Biol. Chem.* 280: 23771-23777 (2005).
Barden et al., "NMR Study of a 34-Residue N-Terminal Fragment of a Parathyroid Hormon-Related Protein Secreted During Humoral Hypercalcemia of Malignancy," *Eur. J. Biochem.* 184: 379-394 (1989).
Barden et al., "NMR Solution Structure of Human Parathyroid Hormone(1-34)," *Biochemistry* 32: 7126-7132 (1993).
Barden et al., "Stabilized NMR Structure of the Hypercalcemia of Malignancy Peptide PTHrP[Ala-26](1-34)Amide," *Biochim. Biophys. Acta* 1208: 256-262 (1994).
Becker et al., "Procedure Guideline for Thyroid Scintigraphy: 1.0," *J. Nucl. Med.* 37: 1264-1266 (1996).
Behar et al., "Histidine at Position 5 is the Specificity "Switch" between Two Parathyroid Hormone Receptor Subtypes," *Endocrinology* 137: 4217-4224 (1996).
Behar et al., "Photoaffinity Cross-Linking Identifies Differences in the Interactions of an Agonist and an Antagonist with the Parathyroid Hormone/Parathyroid Hormone-Related Protein Receptor," *J. Biol. Chem.* 275: 9-17 (2000).
Belinsky et al., "$Ca^{2+}$ and Extracellular Acidification Rate Responses to Parathyroid Hormone Fragments in Rat ROS 17/2 and Human SaOS-2 Cells," *Biochem. Biophys. Res. Commun.* 266: 448-453 (1999).
Bergwitz et al., "Full Activation of Chimeric Receptors by Hybrids between Parathyroid Hormone and Calcitonin. Evidence for a Common Pattern of Ligand-Receptor Interaction," *J. Biol. Chem.* 271: 26469-26472 (1996).
Bergwitz et al., "Residues in the Membrane-spanning and Extracellular Loop Regions of the Parathyroid Hormone (PTH)-2 Receptor Determine Signaling Selectivity for PTH and PTH-Related Peptide," *J. Biol. Chem.* 272: 28861-28868 (1997).
Bergwitz et al., "Identification, Functional Characterization, and Developmental Expression of Two Nonallelic Parathyroid Hormone (PTH)/PTH-Related Peptide Receptor Isoforms in *Xenopus laevis* (Daudin)," *Endocrinology* 139: 723-732 (1998).
Berlot, "A Highly Effective Dominant Negative $\alpha_s$ Construct Containing Mutations that Affect Distinct Functions Inhibits Multiple $G_s$-Coupled Receptor Signaling Pathways," *J. Biol. Chem.* 277: 21080-21085 (2002).
Berridge et al., "Changes in the Levels of Inositol Phosphates after Agonist-Dependent Hydrolysis of Membrane Phosphoinositides," *Biochem. J.* 212: 473-482 (1983).
Bettoun et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab.* 82: 1031-1040 (1997).
Bettoun et al., "Developmental Upregulation of Human Parathyroid Hormone (PTH)/PTH-Related Peptide Receptor Gene Expression from Conserved and Human-specific Promoters," *J. Clin. Invest.* 102: 958-967 (1998).
Bisello et al., "Parathyroid Hormone-Receptor Interactions Identified Directly by PhotocrossLinking and Molecular Modeling Studies," *J. Biol. Chem.* 273: 22498-22505 (1998).
Bisello et al., "Selective Ligand-Induced Stabilization of Active and Desensitized Parathyroid Hormone Type 1 Receptor Conformations," *J. Biol. Chem.* 277: 38524-38530 (2002).
Bork et al., "Go Hunting in Sequence Databases but Watch Out for the Traps," *Trends Genet.* 12: 425-427 (1996).
Bork, "Powers and Pitfalls in Sequence Analysis: The 70% Hurdle," *Genome Res.* 10: 398-400 (2000).
Born et al., "Inhibition of Parathyroid Hormone Bioactivity by Human Parathyroid Hormone (PTH)-(3-84) and PTH-(8-84) Synthesized in *Escherichia coli*," *Endocrinology* 123:1848-1853 (1988).
Bos et al., "Expression of the Parathyroid Hormone Receptor and Correlation with Other Osteoblastic Parameters in Fetal Rat Osteoblasts," *Calcif. Tisse Int.* 58:95-100 (1996).
Bounoutas et al., "Impact of Impaired Receptor Internalization on Calcium Homeostasis in Knock-In Mice Expressing a

(56) References Cited

OTHER PUBLICATIONS

Phosphorylation-Deficient Parathryoid Hormone (PTH)/PTH-Related Peptide Receptor," *Endocrinology.* 147:4674-4679 (2006).
Brenner, "Errors in Genome Annotation," *Trends Genet.* 15: 132-133 (1999).
Bringhurst et al., "Cloned, Stably Expressed Parathyroid Hormone (PTH)/PTH-Related Peptide Receptors Activate Multiple Messenger Signals and Biological Responses in LLC-PK$_1$ Kidney Cells," *Endocrinology* 132: 2090-2098 (1993).
Broadus et al., "Parathyroid Hormone-Related Protein: Structure, Processing, and Physiological Actions," in: *The Parathyroids* (eds. J. P. Bilezikan et al.), pp. 259-294 (Raven Press Ltd., New York, NY, 1994).
Bryant et al., "Helix-Inducing α-Aminoisobutyric Acid in Opioid Mimetic Deltorphin C Analogues," *J. Med. Chem.* 40: 2579-2587 (1997).
Bundi et al., "Characterisation of a Local Structure in the Synthetic Parathyroid Hormone Fragment 1-34 by $^1$H Nuclear-Magnetic-Resonance Techniques," *Eur. J. Biochem.* 91: 201-208 (1978).
Campbell et al., "Totipotency or Multipotentiality of Cultured Cells: Applications and Progress," *Theriogenology* 47: 63-72 (1997).
Carter et al., "Studies of the N-Terminal Region of a Parathyroid Hormone-Related Peptide(1-36) Analog: Receptor Subtype-Selective Agonists, Antagonists, and Photochemical Cross-Linking Agents," *Endocrinology* 140: 4972-4981 (1999).
Carter et al., "Zinc(II)-Mediated Enhancement of the Agonist Activity of Histidine-Substituted Parathyroid Hormone (1-14) Analogues," *Biochem. Biophys. Acta* 1538: 290-304 (2001).
Castro et al., "Dual Regulation of the Parathyroid Hormone (PTH)/PTH-Related Peptide Receptor Signaling by Protein Kinase C and β-Arrestins," *Endocrinology* 143: 3854-3865 (2002).
Castro et al., "Turn-On Switch in Parathyroid Hormone Receptor by a Two-Step Parathyroid Hormone Binding Mechanism," *Proc. Natl. Acad. Sci. USA* 102: 16084-16089 (2005).
Catanzariti et al., "A Novel Expression System for G$_s$-Coupled Receptors," *Bio Techniques* 15: 474-479 (1993).
Caulfield et al., "The Bovine Renal Parathyroid Hormone (PTH) Receptor has Equal Affinity for Two Different Amino Acid Sequences: The Receptor Binding Domains of PTH and PTH-related Protein are Located within the 14-34 Region," *Endocrinology* 127: 83-87 (1990).
Caulfield et al., "Parathyroid Hormone-Receptor Interactions," *Trends Endocrinol. Metab.* 1: 164-168 (1990).
Cervini et al., "Human Growth Hormone-Releasing hGHRH(1-29)-NH$_2$: Systematic Structure-Activity Relationship Studies," *J. Med. Chem.* 41: 717-727 (1998).
Chakrabartty et al., "Large Differences in the Helix Propensities of Alanine and Glycine," *Nature* 351: 586-588 (1991).
Chakravarthy et al., "Parathyroid Hormone Fragment [3-34] Stimulates Protein Kinase C (PKC) Activity in Rat Osteosarcoma and Murine T-lymphoma Cells," *Biochem. Biophys. Res. Commun.* 171: 1105-1110 (1990).
Chauvin et al., "Parathyroid Hormone Receptor Recycling: Role of Receptor Dephosphorylation and β-Arrestin," *Mol. Endocrinol.* 16: 2720-2732 (2002).
Chen et al., "Solution Structure of the Osteogenic 1-31 Fragment of Human Parathyroid Hormone," *Biochemistry* 39: 12766-12777 (2000).
Chorev et al., "Cyclic Parathyroid Hormone Related Protein Antagonists: Lysine 13 to Aspartic Acid 17 [i to (i+4)] Side Chain to Side Chain Lactamization," *Biochemistry* 30: 5968-5974 (1991).
Chu et al., "Porcine Proparathyroid Hormone. Identification, Biosynthesis, and Partial Amino Acid Sequence," *Biochemistry* 14: 3631-3635 (1975).
Civitelli et al., "PTH Elevates Inositol Polyphosphates and Diacylglycerol in a Rat Osteoblast-Like Cell Line," *Am. J. Physiol.* 255: E660-667 (1988).

Civitelli et al., "Parathyroid Hormone-Related Peptide Transiently Increases Cytosolic Calcium in Osteoblast-Like Cells: Comparison with Parathyroid Hormone," *Endocrinology* 125: 1204-1210 (1989).
Cohen et al., "Analogues of Parathyroid Hormone Modified at Positions 3 and 6. Effects on Receptor Binding and Activation of Adenylyl Cyclase in Kidney and Bone," *J. Biol. Chem.* 266: 1997-2004 (1991).
Cole et al., "Regulation of Sodium-Dependent Phosphate Transport by Parathyroid Hormone in Opossum Kidney Cells: Adenosine 3', 5'-Monophosphate-Dependent and -Independent Mechanisms," *Endocrinology* 122: 2981-2989 (1988).
Colquhoun, "Binding, Gating, Affinity, and Efficacy: The Interpretation of Structure-Activity Relationships for Agonists and of the Effects of Mutating Receptors," *Br. J. Pharmacol.* 125: 924-947 (1998).
Condon et al., "The Bioactive Conformation of Human Parathyroid Hormone. Structural Evidence for the Extended Helix Postulate," *J. Am. Chem. Soc.* 122: 3007-3014 (2000).
Cwirla et al., "Peptide Agonist of the Thrombopoietin Receptor as Potent as the Natural Cytokine," *Science* 276: 1696-1699 (1997).
Dang et al., "Gene Therapy and Translational Cancer Research," *Clin. Cancer Res.* 5: 471-474 (1999).
Dautzenberg et al., "Mapping of the Ligand-Selective Domain of the Xenopus laevis Corticotropin-Releasing Factor Receptor 1: Implications for the Ligand-Binding Site," *Proc. Natl. Acad. Sci. USA* 95: 4941-4946 (1998).
DeAlmeida et al., "Identification of Binding Domains of the Growth Hormone-Releasing Hormone Receptor by Analysis of Mutant and Chimeric Receptor Proteins," *Mol. Endocrinol.* 12: 750-765 (1998).
Dean et al., "Mechanisms of Ligand Binding to the Parathyroid Hormone (PTH)/PTH-Related Protein Receptor: Selectivity of a Modified PTH(1-15) Radioligand for Gα$_s$-Coupled Receptor Conformations," *Mol. Endocrinol.* 20: 931-943 (2006).
Dean et al., "Altered Selectivity of Parathyroid Hormone (PTH) and PTH-Related Protein (PTHrP) for Distinct Conformations of the PTH/PTHrP Receptor," *Mol. Endocrinol.* 22:156-166 (2008).
Dempster et al., "Anabolic Actions of Parathyroid Hormone on Bone," *Endocrine Rev.* 14: 690-709 (1993).
Dempster et al., "Erratum: Anabolic Actions of Parathyroid Hormone on Bone," *Endocrine Rev.* 15: 261 (1994).
Dempster et al., "On the Mechanism of Cancellous Bone Preservation in Postmenopausal Women with Mild Primary Hyperparathyroidism," *J. Clin. Endocrinol. Metab.* 84: 1562-1566 (1999).
Ding et al., "A Single Amino Acid Determines the Immunostimulatory Activity of Interleukin 10," *J. Exp. Med.* 191: 213-223 (2000).
Doerks et al., "Protein Annotation: Detective Work for Function Prediction," *Trends Genet.* 14: 248-250 (1998).
Dohlman et al., "Model Systems for the Study of Seven-Transmembrane-Segment Receptors," *Annu. Rev. Biochem.* 60: 653-688 (1991).
Donahue et al., "Differential Effects of Parathyroid Hormone and Its Analogues on Cytosolic Calcium Ion and cAMP Levels in Cultured Rat Osteoblast-Like Cells," *J. Biol. Chem.* 263: 13522-13527 (1988).
Dong et al., "Demonstration of a Direct Interaction between Residue 22 in the Carboxyl-Terminal Half of Secretin and the Amino-Terminal Tail of the Secretin Receptor Using Photoaffinity Labeling," *J. Biol. Chem.* 274: 903-909 (1999).
Dunlay et al., "PTH Receptor Coupling to Phospholipase C is an Alternate Pathway of Signal Transduction in Bone and Kidney," *Am. J. Physiol.* 258: F223-F231 (1990).
Ebert et al., "A Moloney MLV-Rat Somatotropin Fusion Gene Produces Biologically Active Somatotropin in a Transgenic Pig," *Mol. Endocrinol.* 2: 277-283 (1988).
Epand, "Relationships Among Several Different Non-Homologous Polypeptide Hormones," *Mol. Cell Biochem.* 57: 41-47 (1983).
Fairwell et al., "Total Solid-Phase Synthesis, Purification, and Characterization of Human Parathyroid Hormone-(1-84)," *Biochemistry* 22: 2691-2697 (1983).
Fischer et al., "Human Parathyroid Hormone. Immunological Characterization of Antibodies Against a Glandular Extract and the

(56) References Cited

OTHER PUBLICATIONS

Synthetic Amino-Terminal Fragments 1-12 and 1-34 and their Use in the Determination of Immunoreactive Hormone in Human Sera," *J. Clin. Invest.* 54: 1382-1394 (1974).
Freyaldenhoven et al., "Protein Kinase C Differentially Modulates PTH- and $PGE_2$-Sensitive Adenylate Cyclase in Osteoblast-Like Cells," *Am. J. Physiol.* 262: E87-E95 (1992).
Fujimori et al., "Dissociation of Second Messenger Activation by Parathyroid Hormone Fragments in Osteosarcoma Cells," *Endocrinology* 128: 3032-3039 (1991).
Fujimori et al., "Structure-Function Relationship of Parathyroid Hormone: Activation of Phospholipase-C, Protein Kinase-A and -C in Osteosarcoma Cells," *Endocrinology* 130: 29-36 (1992).
Fukayama et al., "Mechanisms of Desensitization to Parathyroid Hormone in Human Osteoblast-Like SaOS-2 Cells," *Endocrinology* 131: 1757-1769 (1992).
Fukayama et al., "Role of Protein Kinase-A in Homologous Down-Regulation of Parathyroid Hormone (PTH)/PTH-Related Peptide Receptor Messenger Ribonucleic Acid in Human Osteoblast-Like SaOS-2 Cells," *Endocrinology* 134: 1851-1858 (1994).
Gaich et al., "Amino-Terminal Parathyroid Hormone-Related Protein: Specific Binding and Cytosolic Calcium Responses in Rat Insulinoma Cells," *Endocrinology* 132: 1402-1409 (1993).
Gardella et al., "Expression of Human Parathyroid Hormone-(1-84) in *Escherichia coli* as a Factor X-cleavable Fusion Protein," *J. Biol. Chem.* 265: 15854-15859 (1990).
Gardella et al., "Mutational Analysis of the Receptor-Activating Region of Human Parathyroid Hormone," *J. Biol. Chem.* 266: 13141-13146 (1991).
Gardella et al., "Scanning Mutagenesis of the 23-35 Region of Parathyroid Hormone Reveals Important Determinants of Receptor Binding," *Calcium Regulating Hormones and Bone Metabolism: Basic and Clinical Aspects* (eds. D.V. Cohn et al.), vol. 11, pp. 218-222 (Excerpta Medica, Amsterdam, 1992).
Gardella et al., "Analysis of Parathyroid Hormone's Principal Receptor-Binding Region by Site-Directed Mutagenesis and Analog Design," *Endocrinology* 132: 2024-2030 (1993).
Gardella et al., "Determinants of $[Arg^2]$PTH-(1-34) Binding and Signaling in the Transmembrane Region of the Parathyroid Hormone Receptor," *Endocrinology* 135: 1186-1194 (1994).
Gardella et al., "Parathyroid Hormone (PTH)-PTH-Related Peptide Hybrid Peptides Reveal Functional Interactions Between the 1-14 and 15-34 Domains of the Ligand," *J. Biol. Chem.* 270: 6584-6588 (1995).
Gardella et al., "Converting Parathyroid Hormone-Related Peptide (PTHrP) into a Potent PTH-2 Receptor Agonist," *J. Biol. Chem.* 271: 19888-19893 (1996).
Gardella et al., "Transmembrane Residues of the Parathyroid Hormone (PTH)/PTH-Related Peptide Receptor that Specifically Affect Binding and Signaling by Agonist Ligands," *J. Biol. Chem.* 271: 12820-12825 (1996).
Gensure et al., "Multiple Sites of Contact between the Carboxyl-Terminal Binding Domain of PTHrP-(1-36) Analogs and the Amino-Terminal Extracellular Domain of the PTH/PTHrP Receptor Identified by Photoaffinity Cross-Linking," *J. Biol. Chem.* 276: 28650-28658 (2001).
Gensure et al., "Identification of Determinants of Inverse Agonism in a Constitutively Active Parathyroid Hormone/Parathyroid Hormone-Related Peptide Receptor by Photoaffinity Cross-Linking and Mutational Analysis," *J. Biol. Chem.* 276:42692-42699 (2001).
Gensure et al., "Identification of a Contact Site for Residue 19 of Parathyroid Hormone (PTH) and PTH-Related Protein Analogs in Transmembrane Domain Two of the Type 1 PTH Receptor," *Mol Endocrinol.* 17: 2647-2658 (2003).
Gensure et al., "Parathyroid Hormone and Parathyroid Hormone-Related Peptide, and their Receptors," *Biochem. Biophys. Res. Commun.* 328: 666-678 (2005).
Goltzman et al., "Influence of Guanyl Nucleotides on Parathyroid Hormone-Stimulated Adenylyl Cyclase Activity in Renal Cortical Membranes," *Endocrinology* 103: 1352-1360 (1978).
Goltzmann et al., "Analysis of the Requirements for Parathyroid Hormone Action in Renal Membranes with the Use of Inhibiting Analogues," *J. Biol. Chem.* 250: 3199-3203 (1975).
Gombert et al., "Alanine and D-Amino Acid Scan of Human Parathyroid Hormone," *Peptides: Chemistry, Structure and Biology* (eds. P.T.P. Kaumaya et al.), pp. 661-662 (Mayflower Sci. Ltd., England, 1996).
Goud et al., "Solid-Phase Synthesis and Biologic Activity of Human Parathyroid Hormone (1-84)," *J. Bone Miner. Res.* 6: 781-789 (1991).
Grace et al., "NMR Structure and Peptide Hormone Binding Site of the First Extracellular Domain of a Type B1 G Protein-Coupled Receptor," *Proc. Natl. Acad. Sci. USA* 101: 12836-12841 (2004).
Greenberg et al., "Mapping the Bimolecular Interface of the Parathyroid Hormone (PTH)-PTH1 Receptor Complex: Spatial Proximity between $Lys^{27}$ (of the Hormone Principal Binding Domain) and $Leu^{261}$ (of the First Extracellular Loop) of the Human PTH1 Receptor," *Biochemistry* 39: 8142-8152 (2000).
Gronwald et al., "Structure of Recombinant Human Parathyroid Hormone Solution Using Multidimensional NMR Spectroscopy," *Biol. Chem. Hoppe-Seyler* 377: 175-186 (1996).
Guo et al., "Parathyroid Hormone (PTH)/PTH-Related Peptide Receptor Density Modulates Activation of Phospholipase C and Phosphate Transport by PTH in LLC-PK1 Cells," *Endocrinology* 136: 3884-3891 (1995).
Habashita et al., "Synthesis and Biological Activities of hPTH(1-34) Analogues: Modification of the Middle Part and C-terminal Alkylamides," *Peptide Science—Present and Future: Proceedings of the 1st International Peptide Symposium* (ed. Y. Shimonishi), pp. 711-713 (Kluwer Acad. Pub., Great Britain, 1997).
Hammer et al., "Genetic Engineering of Mammalian Embryos," *J. Anim. Sci.* 63: 269-278 (1986).
Heinrich et al., "Gene Encoding Parathyroid Hormone. Nucleotide Sequence of the Rat Gene and Deduced Amino Acid Sequence of Rat Preproparathyroid Hormone," *J. Biol. Chem.* 259: 3320-3329 (1984).
Heinrich et al., "Rat Parathyroid Hormone Gene, Exons II and III," Alignment result 8, SEQ ID No. 1, Database: GenEmbl, Accession No. K01268 (Apr. 27, 1993).
Hilliker et al., "Truncation of the Amino Terminus of PTH Alters Its Anabolic Activity on Bone In Vivo," *Bone* 19: 469-477 (1996).
Hjorth et al., "Constitutive Activity of Glucagon Receptor Mutants," *Mol. Endocrinol.* 12: 78-86 (1998).
Hoare et al., "Measurement of Agonist and Antagonist Ligand-Binding Parameters at the Human Parathyroid Hormone Type 1 Receptor: Evaluation of Receptor States and Modulation by Guanine Nucleotide," *J. Pharmacol. Exp. Ther.* 289: 1323-1333 (1999).
Hoare et al., "Evaluating the Signal Transduction Mechanism of the Parathyroid Hormone 1 Receptor," *J. Biol. Chem.* 276: 7741-7753 (2001).
Hoare et al., "Conformational States of the Corticotropin Releasing Factor 1 (CRF1) Receptor: Detection, and Pharmacological Evaluation by Peptide Ligands," *Peptides* 24: 1881-1897 (2003).
Hollnagel et al., "Domain-Specific Gene Activation by Parathyroid Hormone in Osteoblastic ROS17/2.8 Cells," *J. Biol. Chem.* 271: 21870-21877 (1996).
Holtmann et al., "Critical Contributions of Amino-terminal Extracellular Domains in Agonist Binding and Activation of Secretin and Vasoactive Intestinal Polypeptide Receptors. Studies of Chimeric Receptors," *J. Biol. Chem.* 270: 14394-14398 (1995).
Holtmann et al., "Molecular Basis and Species Specificity of High Affinity Binding of Vasoactive Intestinal Polypeptide by the Rat Secretin Receptor," *J. Pharmacol. Exp. Ther.* 279: 555-560 (1996).
Horiuchi et al., "A Parathyroid Hormone Inhibitor In Vivo: Design and Biological Evaluation of a Hormone Analog," *Science* 220: 1053-1055 (1983).
Horiuchi et al., "Evaluation of a Parathyroid Hormone Antagonist in an In Vivo Multiparameter Bioassay," *Am. J. Physiol.* 253: E187-192 (1987).
Hruska et al., "Stimulation of Inositol Trisphosphate and Diacylglycerol Production in Renal Tubular Cells by Parathyroid Hormone," *J. Clin. Invest.* 79: 230-239 (1987).

(56) References Cited

OTHER PUBLICATIONS

Iida-Klein et al., "Truncation of the Carboxyl-terminal Region of the Rat Parathyroid Hormone (PTH)/PTH-Related Peptide Receptor Enhances PTH Stimulation of Adenylyl Cyclase but Not Phospholipase C," *J. Biol. Chem.* 270: 8458-8465 (1995).
Iida-Klein et al., "Structural Requirements of Parathyroid Hormone/Parathyroid Hormone-Related Peptide Receptors for Phospholipase C Activation and Regulation of Phosphate Uptake," *Miner. Electrolyte Metab.* 21: 177-179 (1995).
Iida-Klein et al., "Mutations in the Second Cytoplasmic Loop of the Rat Parathyroid Hormone (PTH)/PTH-Related Protein Receptor Result in Selective Loss of PTH-stimulated Phospholipase C Activity," *J. Biol. Chem.* 272: 6882-6889 (1997).
Inomata et al., "Characterization of a Novel Parathyroid Hormone (PTH) Receptor with Specificity for the Carboxyl-Terminal Region of PTH-(1-84)," *Endocrinology* 136: 4732-4740 (1995).
Ishihara et al., "Molecular Cloning and Expression of a cDNA Encoding the Secretin Receptor," *EMBO J.* 10: 1635-1641 (1991).
Iwakura et al., "Effects of the Length of a Glycine Linker Connecting the N- and C-Termini of a Circularly Permuted Dihydrofolate Reductase," *Protein Eng.* 11: 707-713 (1998).
Jans et al., "LLC-$PK_1$ Cell Mutants in cAMP Metabolism Respond Normally to Phorbol Esters," *FEBS Lett.* 205: 127-131 (1986).
Janulis et al., "Structure-Function Requirements of Parathyroid Hormone for Stimulation of 1,25-Dihydroxyvitamin $D_3$ Production by Rat Renal Proximal Tubules," *Endocrinology* 133: 713-719 (1993).
Ji et al., "Human Choriogonadotropin Binds to a Lutropin Receptor with Essentially No N-terminal Extension and Stimulates cAMP Synthesis," *J. Biol. Chem.* 266: 13076-13079 (1991).
Jin et al., "Crystal Structure of Human Parathyroid Hormone 1-34 at 0.9-A Resolution," *J. Biol. Chem.* 275: 27238-27244 (2000).
Jing et al., "GDNF-Induced Activation of the Ret Protein Tyrosine Kinase Is Mediated by GDNFR-α, a Novel Receptor for GDNF," *Cell* 85: 1113-1124 (1996).
Jobert et al., "Parathyroid Hormone-Induced Calcium Release from Intracellular Stores in a Human Kidney Cell Line in the Absence of Stimulation of Cyclic Adenosine 3',5'-Monophosphate Production," *Endocrinology* 138: 5282-5292 (1997).
Jouishomme et al., "The Protein Kinase-C Activation Domain of the Parathyroid Hormone," *Endocrinology* 130: 53-60 (1992).
Jouishomme et al., "Further Definition of the Protein Kinase C Activation Domain of the Parathyroid Hormone," *J. Bone Miner. Res.* 9: 943-949 (1994).
Joun et al., "Tissue-specific Transcription Start Sites and Alternative Splicing of the Parathyroid Hormone (PTH)/PTH-related Peptide (PTHrP) Receptor Gene: A New PTH/PTHrP Receptor Splice Variant that Lacks the Signal Peptide," *Endocrinology* 138: 1742-1749 (1997).
Jüppner et al., "The Parathyroid Hormone-Like Peptide Associated with Humoral Hypercalcemia of Malignancy and Parathyroid Hormone Bind to the Same Receptor on the Plasma Membrane of ROS 17/2.8 Cells," *J. Biol. Chem.* 263: 8557-8560 (1988).
Jüppner et al., "Properties of Amino-Terminal Parathyroid Hormone-Related Peptides Modified at Positions 11-13," *Peptides* 11: 1139-1142 (1990).
Jüppner et al., "A G Protein-linked Receptor for Parathyroid Hormone and Parathyroid Hormone-Related Peptide," *Science* 254: 1024-1026 (1991).
Jüppner et al., "The Extracellular Amino-Terminal Region of the Parathyroid Hormone (PTH)/PTH-related Peptide Receptor Determines the Binding Affinity for Carboxyl-Terminal Fragments of PTH-(1-34)," *Endocrinology* 134: 879-884 (1994).
Kappel et al., "Regulating Gene Expression in Transgenic Animals," *Curr. Op. Biotechnol.* 3: 548-553 (1992).
Karaplis et al., "Lethal Skeletal Dysplasia From Targeted Disruption of the Parathyroid Hormone-Related Peptide Gene," *Genes Dev.* 8: 277-289 (1994).

Kaufman et al., "Transgenic Analysis of a 100-kb Human β-Globin Cluster-Containing DNA Fragment Propagated as a Bacterial Artificial Chromosome," *Blood* 94: 3178-3184 (1999).
Kaufmann et al., "Functional Expression of a Stably Transfected Parathyroid Hormone/Parathyroid Hormone Related Protein Receptor Complementary DNA in CHO cells," *Mol. Cell. Endocrinol.* 104: 21-27 (1994).
Kaul et al., "Stereochemical Control of Peptide Folding," *Bioorg. Med. Chem.* 7: 105-117 (1999).
Kemp et al., "Parathyroid Hormone-Related Protein of Malignancy: Active Synthetic Fragments," *Science* 238: 1568-1570 (1987).
Kimura et al., "Strategy for the Synthesis of Large Peptides: An Application to the Total Synthesis of Human Parathyroid Hormone [hPTH)1-84)]," *Biopolymers* 20: 1823-1832 (1981).
Kimura et al., "Discovery of a Novel Thrombopoietin Mimic Agonist Peptide," *J. Biochem.* 122: 1046-1051 (1997).
Klaus et al., "Investigation of the Solution Structure of the Human Parathyroid Hormone Fragment (1-34) by $^1H$ NMR Spectroscopy, Distance Geometry, and Molecular Dynamics Calculations," *Biochemistry* 30: 6936-6942 (1991).
Kolakowski, "GCRDb: A G-Protein-Coupled Receptor Database," *Receptors and Channels* 2: 1-7 (1994).
Kong et al., "The Rat, Mouse and Human Genes Encoding the Receptor for Parathyroid Hormone and Parathyroid Hormone-Related Peptide are Highly Homologous," *Biochem. Biophys. Res. Commun.* 200: 1290-1299 (1994).
Kovacs et al., "Parathyroid Hormone-Related Peptide (PTHrP) Regulates Fetal-placental Calcium Transport Through a Receptor Distinct from the PTH/PTHrP Receptor," *Proc. Natl. Acad. Sci. USA* 93: 15233-15238 (1996).
Kronenberg et al., "Parathyroid Hormone: Biosynthesis, Secretion, Chemistry, and Action," *Handbook of Experimental Pharmacology* (eds. G.R. Mundy et al.), pp. 507-567 (Springer-Verlag, Heidelberg, Germany, 1993).
Kronenberg et al., "The PTH/PTHrP Receptor: One Receptor for Two Ligands," in: *Molecular Genetics of Endocrine Disorders* (ed. R.V. Thakker), pp. 389-420 (Chapman & Hall, New York, NY, 1997).
Lanske et al., "PTH/PTHrP Receptor in Early Development and Indian Hedgehog-Regulated Bone Growth," *Science* 273: 663-666 (1996).
Lee et al., "Role of the Extracellular Regions of the Parathyroid Hormone (PTH)/PTH-Related Peptide Receptor in Hormone Binding," *Endocrinology* 135: 1488-1495 (1994).
Lee et al., "Homolog-scanning Mutagenesis of the Parathyroid Hormone (PTH) Receptor Reveals PTH-(1-34) Binding Determinants in the Third Extracellular Loop," *Mol. Endocrinol.* 9: 1269-1278 (1995).
Li et al., "Minimization of a Polypeptide Hormone," *Science* 270: 1657-1660 (1995).
Lin et al., "Expression Cloning of an Adenylate Cyclase-Coupled Calcitonin Receptor," *Science* 254: 1022-1024 (1991).
Livnah et al., "Functional Mimicry of a Protein Hormone by a Peptide Agonist: The EPO Receptor Complex at 2.8 A," *Science* 273: 464-471 (1996).
Luck et al., "The (1-14) Fragment of Parathyroid Hormone (PTH) Activates Intact and Amino-terminally Truncated PTH-1 Receptors," *Mol. Endocrinol.* 13: 670-680 (1999).
Majeska et al., "Parathyroid Hormone-Responsive Clonal Cell Lines from Rat Osteosarcoma," *Endocrinology* 107: 1494-1503 (1980).
Mannstadt et al., "Evidence for a Ligand Interaction Site at the Amino-terminus of the Parathyroid Hormone (PTH)/PTH-related Protein Receptor from Cross-Linking and Mutational Studies," *J. Biol. Chem.* 273: 16890-16896 (1998).
Marx et al., "Structure of Human Parathyroid Hormone 1-37 in Solution," *J. Biol. Chem.* 270: 15194-15202 (1995).
Marx et al., "Structure-Activity Relation of $NH_2$-terminal Human Parathyroid Hormone Fragments," *J. Biol. Chem.* 273: 4308-4316 (1998).

(56) References Cited

OTHER PUBLICATIONS

Marx et al., "Solution Structures of Human Parathyroid Hormone Fragments hPTH(1-34) and hPTH (1-39) and Bovine Parathyroid Hormone Fragment bPTH(1-37)," *Biochem. Biophys. Res. Commun.* 267: 213-220 (2000).

Matsumoto et al., "Daily Nasal Spray of hPTH(1-34) for 3 Months Increases Bone Mass in Osteoporotic Subjects: A Pilot Study," *Osteoporos. Int.* 17: 1532-1538 (2006).

McCuaig et al., "Molecular Cloning of the Gene Encoding the Mouse Parathyroid Hormone/Parathyroid Hormone-Related Peptide Receptor," *Proc. Natl. Acad. Sci. USA* 91: 5051-5055 (1994).

Menniti et al., "Different Modes of Regulation for Receptors Activating Phospholipase C in the Rat Pancreatoma Cell Line AR4-2J," *Mol. Pharmacol.* 40: 727-733 (1991).

Mickle et al., "Genotype-Phenotype Relationships in Cystic Fibrosis," *Med. Clin. North Am.* 84: 597-607 (2000).

Mikayama et al., "Molecular Cloning and Functional Expression of a cDNA Encoding Glycosylation-Inhibiting Factor," *Proc. Natl. Acad. Sci USA* 90: 10056-10060 (1993).

Mitchell et al., "Mechanisms of Homologous and Heterologous Regulation of Parathyroid Hormone Receptors in the Rat Osteosarcoma Cell Line UMR-106," *Endocrinology* 126: 2650-2660 (1990).

Moretto et al., "(αMe)Nva: Stereoselective Syntheses and Preferred Conformations of Selected Model Peptides," *J. Pept. Res.* 56: 283-297 (2000).

Mullins et al., "Perspective Series: Molecular Medicine in Genetically Engineered Animals," *J. Clin. Invest.* 98: S37-S40 (1996).

Murray et al., "Dexamethasone-Treated ROS 17/2.8 Rat Osteosarcoma Cells are Responsive to Human Carboxylterminal Parathyroid Hormone Peptide hPTH (53-84): Stimulation of Alkaline Phosphatase," *Calcif. Tissue Int.* 49: 120-123 (1991).

Musso et al., "Renal Vasodilatation and Microvessel Adenylate Cyclase Stimulation by Synthetic Parathyroid Hormone-Like Protein Fragments," *Eur. J. Pharmacol.* 174: 139-151 (1989).

Nakamoto et al., "Probing the Bimolecular Interactions of Parathyroid Hormone with the Human Parathyroid Hormone/Parathyroid Hormone-Related Protein Receptor. 1. Design, Synthesis and Characterization of Photoreactive Benzophenone-Containing Analogs of Parathyroid Hormone," *Biochemistry* 34: 10546-10552 (1995).

Nakamura et al., "Action of Fragments of Human Parathyroid Hormone on Blood Pressure in Rats," *Endocrinol. Jpn.* 28: 547-549 (1981).

Neer et al., "Effect of Parathyroid Hormone (1-34) On Fractures and Bone Mineral Density in Postmenopausal Women with Osteoporosis," *N. Engl. J. Med.* 344: 1434-1441 (2001).

Neugebauer et al., "Structural Elements of Human Parathyroid Hormone and their Possible Relation to Biological Activities," *Biochemistry* 31: 2056-2063 (1992).

Neugebauer et al., "Solution Structure and Adenylyl Cyclase Stimulating Activities of C-terminal Truncated Human Parathyroid Hormone Analogues," *Biochemistry* 34: 8835-8842 (1995).

Ngo et al., "Chapter 14: Computational Complexity, Protein Structure Prediction, and the Levinthal Paradox," in: *The Protein Folding Problem and Tertiary Structure Prediction* (eds. K.M. Merz et al.), pp. 492-495 (Birkhäuser Verlag, Boston, MA, 1994).

Nielsen et al., "Identification of Prokaryotic and Eukaryotic Signal Peptides and Prediction of their Cleavage Sites," *Prot. Eng.* 10: 1-6 (1997).

Nissenson et al., "Synthetic Peptides Comprising the Amino-Terminal Sequence of a Parathyroid Hormone-Like Protein from Human Malignancies. Binding to Parathyroid Hormone Receptors and Activation of Adenylate Cyclase in Bone Cells and Kidney," *J. Biol. Chem.* 263: 12866-12871 (1988).

Nussbaum et al., "Parathyroid Hormone • Renal Receptor Interactions. Demonstration of Two Receptor-binding Domains," *J. Biol. Chem.* 255: 10183-10187 (1980).

Nutt et al., "Removal of Partial Agonism from Parathyroid Hormone (PTH)-Related Protein-(7-34)NH$_2$ by Substitution of PTH Amino Acids at Positions 10 and 11," *Endocrinology* 127: 491-493 (1990).

Oldenburg et al., "Conformational Studies on Analogs of Recombinant Parathyroid Hormone and their Interactions with Phospholipids," *J. Biol. Chem.* 271: 17582-17591 (1996).

Orkin et al., "Report and Recommendations of the Panel to Assess the NIH Investment in Research on Gene Therapy," available online at http://www.nih.gov/news/panelrep.html, pp. 1-39 (1995).

Orloff et al., "Analysis of PTHRP Binding and Signal Transduction Mechanisms in Benign and Malignant Squamous Cells," *Am. J. Physiol.* 262: E599-E607 (1992).

Orloff et al., "Further Evidence for a Novel Receptor for Amino-Terminal Parathyroid Hormone-Related Protein on Keratinocytes and Squamous Carcinoma Cell Lines," *Endocrinology* 136: 3016-3023 (1995).

Orloff et al., "A Midregion Parathyroid Hormone-Related Peptide Mobilizes Cytosolic Calcium and Stimulates Formation of Inositol Trisphosphate in a Squamous Carcinoma Cell Line," *Endocrinology* 137: 5376-5385 (1996).

Pang et al., "Purification of Unique a Subunits of GTP-Binding Regulatory Proteins (G Proteins) by Affinity Chromatography with Immobilized βγ Subunits," *J. Biol. Chem.* 265: 18707-18712 (1990).

Parsons et al., "Pharmacology of Parathyroid Hormone and Some of its Fragments and Analogues," in: *Calcium-regulating hormones. Proceedings of the Fifth Parathyroid Conference*, Oxford, United Kingdom, Jul. 21-26, 1974 (eds. R.V. Talmage et al.), pp. 33-39 (Am. Elsevier Pub. Co., New York, NY, 1975).

Peggion et al., "Structure-Function Studies of Analogues of Parathyroid Hormone (PTH)-1-34 Containing β-Amino Acid Residues in Positions 11-13," *Biochemistry* 41: 8162-8175 (2002).

Pellegrini et al., "Binding Domain of Human Parathyroid Hormone Receptor: From Conformation to Function," *Biochemistry* 37: 12737-12743 (1998).

Pellegrini et al., "Addressing the Tertiary Structure of Human Parathyroid Hormone-(1-34)," *J. Biol. Chem.* 273: 10420-10427 (1998).

Pettit et al., "The Development of Site-Specific Drug-Delivery Systems for Protein and Peptide Biopharmaceuticals," *Trends Biotechnol.* 16: 343-349 (1998).

Phillips, "The Challenge of Gene Therapy and DNA Delivery," *J. Pharm. Pharmacol.* 53: 1169-1174 (2001).

Pines et al., "Generation and Characterization of Human Kidney Cell Lines Stably Expressing Recombinant Human PTH/PTHrP Receptor: Lack of Interaction with a C-Terminal Human PTH Peptide," *Endocrinology* 135: 1713-1716 (1994).

Pines et al., "Inositol 1-,4-,5-Trisphosphate-Dependent Ca$^{2+}$ Signaling by the Recombinant Human PTH/PTHrP Receptor Stably Expressed in a Human Kidney Cell Line," *Bone* 18: 381-389 (1996).

Plotkin et al., "Dissociation of Bone Formation from Resorption during 2-week Treatment with Human Parathyroid Hormone-Related Peptide-(1-36) in Humans: Potential as an Anabolic Therapy for Osteoporosis," *J. Clin. Endocrinol. Metab.* 83: 2786-2791 (1998).

Potts et al., "Structure Based Design of Parathyroid Hormone Analogs," *J. Endocrinol.* 154 Suppl: S15-S21 (1997).

Potts et al., "Parathyroid Hormone and Parathyroid Hormone-Related Peptide in Calcium Homeostasis, Bone Metabolism, and Bone Development: The Proteins, Their Genes, and Receptors," in: *Metabolic Bone Disease*, 3rd Edition (eds. L.V. Avioli et al.), pp. 51-94 (Acad. Press, San Diego, CA, 1998).

Ray et al., "NMR Solution Structure of the [Ala$^{26}$]Parathyroid-Hormone-Related Protein(1-34) Expressed in Humoral Hypercalcemia of Malignancy," *Eur. J. Biochem.* 211: 205-211 (1993).

Reid et al., "Parathyroid Hormone Acutely Elevates Intracellular Calcium in Osteoblastlike Cells," *Am. J. Physiol.* 253: E45-E51 (1987).

Reidhaar-Olson et al., "Active Variants of Human Parathyroid Hormone (1-34) with Multiple Amino Acid Substitutions," *Mol. Cell. Endocrinol.* 160: 135-147 (2000).

(56) References Cited

OTHER PUBLICATIONS

Rhee et al., "In Vitro and In Vivo Effect of Parathyroid Hormone Analogue (1-14) Containing α-amino-iso-butyric acid residue (Aib)$^{1,3}$," *Yonsei Med. J.* 47:214-222 (2006).

Rixon et al., "Parathyroid Hormone Fragments May Stimulate Bone Growth in Ovariectomized Rats by Activating Adenylyl Cyclase," *J. Bone Miner. Res.* 9: 1179-1189 (1994).

Roe et al., "Parathyroid Hormone 1-34 (hPTH 1-34) and Estrogen Produce Dramatic Bone Density Increases in Postmenopausal Osteoporosis. Results from a Placebo-Controlled Randomized Trial," *J. Bone Miner. Res.* 14: S137, Abstract No. 1019 (1999).

Rölz et al., "Characterization of the Molecular Motions of Constitutively Active G Protein-Coupled Receptors for Parathyroid Hormone," *Biophys. Chem.* 89: 119-128 (2001).

Romano et al., "Latest Developments in Gene Transfer Technology: Achievements, Perspectives, and Controversies over Therapeutic Applications," *Stem Cells* 18: 19-39 (2000).

Rosenblatt et al., "Design and Synthesis of Parathyroid Hormone Analogues of Enhanced Biological Activity," *Endocr. Res. Commun.* 4: 115-133 (1977).

Rosenblatt et al., "Identification of a Receptor-binding Region in Parathyroid Hormone," *Endocrinology* 107: 545-550 (1980).

Rosenblatt, "Parathyroid Hormone: Chemistry and Structure-Activity Relations," *Pathobiol. Annu.* 11: 53-86 (1981).

Rosol et al., "Sequences of the cDNAs Encoding Canine Parathyroid Hormone-Related Protein and Parathyroid Hormone," *Gene* 160: 241-243 (1995).

Rubin et al., "Molecular Cloning and Expression of Receptors for Parathyroid Hormone (PTH) and PTH-Related (PTHrP) Protein in Zebrafish," *Am. Zoologist* 36: 97A, Abstract No. 373 (1996).

Rubin et al., "Parathyroid Hormone (PTH)/PTH-Related (PTHRP) Receptor Cloning and in Situ Hybridization in the Zebrafish, Danio Rerio," *Am. Zoologist* 37: 181A, Abstract No. 651 (1997).

Rubin et al., "Molecular Cloning of a Zebrafish cDNA Encoding a Novel Parathyroid Hormone (PTH)/PTH-Related Protein (PTHrP) Receptor (PPR)," *Bone* 23: S255, Abstract No. T224 (1998).

Rubin et al., "Zebrafish Express the Common Parathyroid Hormone/Parathyroid Hormone-Related Peptide Receptor (PTH1R) and a Novel Receptor (PTH3R) That is Preferentially Activated by Mammalian and Fugufish Parathyroid Hormone-Related Peptide," *J. Biol. Chem.* 274: 28185-28190 (1999).

Sacchetti et al., "Green Fluorescent Protein Variants Fold Differentially in Prokaryotic and Eukaryotic Cells," *J. Cell. Biochem. Suppl.* 36: 117-128 (2001).

Sargent et al., "Membrane Lipid Phase as Catalyst for Peptide-Receptor Interactions," *Proc. Natl. Acad. Sci. USA* 83: 5774-5778 (1986).

Schipani et al., "Identical Complementary Deoxyribonucleic Acids Encode a Human Renal and Bone Parathyroid Hormone (PTH)/PTH-Related Peptide Receptor," *Endocrinology* 132: 2157-2165 (1993).

Schipani et al., "Pseudohypoparathyroidism Type Ib is not Caused by Mutations in the Coding Exons of the Human Parathyroid Hormone (PTH)/PTH-Related Peptide Receptor Gene," *J. Clin. Endocrinol. Metab.* 80: 1611-1621 (1995).

Schipani et al., "A Constitutively Active Mutant PTH-PTHrP Receptor in Jansen-Type Metaphyseal Chondrodysplasia," *Science* 268: 98-100 (1995).

Schneider et al., "Cloning and Functional Expression of a Human Parathyroid Hormone Receptor," *Eur. J. Pharmacol.* 246: 149-155 (1993).

Schneider et al., "A C-Terminally Truncated Human Parathyroid Hormone Receptor is Functional and Activates Multiple G Proteins," *FEBS Lett.* 351: 281-285 (1994).

Segre et al., "Characterization of Parathyroid Hormone Receptors in Canine Renal Cortical Plasma Membranes Using a Radioiodinated Sulfur-Free Hormone Analogue. Correlation of Binding with Adenylate Cyclase Activity," *J. Biol. Chem.* 254: 6980-6986 (1979).

Segre et al., "Receptors for Secretin, Calcitonin, Parathyroid Hormone (PTH)/PTH-Related Peptide, Vasoactive Intestinal Peptide, Glucagonlike Peptide 1, Growth Hormone-Releasing Hormone, and Glucagon Belong to a Newly Discovered G-protein-Linked Receptor Family," *Trends Endocrinol. Metab.* 4: 309-314 (1993).

Seuwen et al., "Heparin-Insensitive Calcium Release from Intracellular Stores Triggered by the Recombinant Human Parathyroid Hormone Receptor," *Br. J. Pharmacol.* 114: 1613-1620 (1995).

Shen et al., "Effects of Combined and Separate Intermittent Administration of Low-Dose Human Parathyroid Hormone Fragment (1-34) and 17β-Estradiol on Bone Histomorphometry in Ovariectomized Rats with Established Osteopenia," *Calcif. Tissue Int.* 50: 214-220 (1992).

Shigeno et al., "Parathyroid Hormone Receptors are Plasma Membrane Glycoproteins with Asparagine-Linked Oligosaccharides," *J. Biol. Chem.* 263: 3872-3878 (1988).

Shimada et al., "Purification and Characterization of a Receptor for Human Parathyroid Hormone and Parathyroid Hormone-Related Peptide," *J. Biol. Chem.* 277: 31774-31780 (2002).

Shimizu et al., "Type-Substitution Analysis of the Amino-Terminal Fragment of Parathyroid Hormone, PTH(1-14): An Approach toward New Low Molecular Weight PTH Agonists," *J. Bone Miner. Res.* 14: S289, Abstract No. F398 (1999).

Shimizu et al., "Autoactivation of Type-1 Parathyroid Hormone Receptors Containing a Tethered Ligand," *J. Biol. Chem.* 275: 19456-19460 (2000).

Shimizu et al., "Minimization of Parathyroid Hormone. Novel Amino-Terminal Parathyroid Hormone Fragments with Enhanced Potency in Activating the Type-1 Parathyroid Hormone Receptor," *J. Biol. Chem.* 275: 21836-21843 (2000).

Shimizu et al., "Enhanced Activity in Parathyroid Hormone-(1-14) and -(1-11): Novel Peptides for Probing Ligand-Receptor Interactions," *Endocrinology* 142: 3068-3074 (2001).

Shimizu et al., "Parathyroid Hormone (PTH)-(1-14) and -(1-11) Analogs Conformationally Constrained by α-Aminoisobutyric Acid Mediate Full Agonist Responses via the Juxtamembrane Region of the PTH-1 Receptor," *J. Biol. Chem.* 276: 49003-49012 (2001).

Shimizu et al., "Residue 19 of the Parathyroid Hormone (PTH) Modulates Ligand Interaction with the Juxtamembrane Region of the PTH-1 Receptor," *Biochemistry* 41: 13224-13233 (2002).

Shimizu et al., "Structurally Varied Conformationally Constrained Amino Acids Substitutions at Positions 1 and 3 of PTH(1-14) Preserve or Enhance P1R Binding Affinity and cAMP-signaling Potency," *J. Bone Miner. Res.* 17: S389 (2002).

Shimizu et al., "Functional Evidence for an Intramolecular Side Chain Interaction between Residues 6 and 10 of Receptor-Bound Parathyroid Hormone Analogues," *Biochemistry* 42: 2282-2290 (2003).

Shimizu et al., "Amino-Terminal Parathyroid Hormone Fragment Analogs Containing α,α-di-alkyl Amino Acids at Positions 1 and 3," *J. Bone Miner. Res.* 19: 2078-2086 (2004).

Shimizu et al., "Novel Parathyroid Hormone (PTH) Antagonists that Bind to the Juxtamembrane Portion of the PTH/PTH-Related Protein Receptor," *J. Biol. Chem.* 280: 1797-1807 (2005).

Shukunami et al., "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," *J. Cell Biol.* 133: 457-468 (1996).

Siegfried et al., "Parathyroid Hormone Stimulates Ecto-5'-Nucleotidase Activity in Renal Epithelial Cells: Role of Protein Kinase-C," *Endocrinology* 136:1267-1275 (1995).

Simon et al., "Diversity of G Proteins in Signal Transduction," *Science* 252: 802-808 (1991).

Skolnick et al., "From Genes to Protein Structure and Function: Novel Applications of Computational Approaches in the Genomic Era," *Trends Biotechnol.* 18: 34-39 (2000).

Slovik et al., "Restoration of Spinal Bone in Osteoporotic Men by Treatment with Human Parathyroid Hormone (1-34) and 1,25-dihydroxyvitamin D," *J. Bone Miner. Res.* 1: 377-381 (1986).

Smith et al., "The Challenges of Genome Sequence Annotation or 'The devil is in the details'," *Nat. Biotechnol.* 15: 1222-1223 (1997).

Strathmann et al., "G Protein Diversity: A Distinct Class of α Subunits is Present in Vertebrates and Invertebrates," *Proc. Natl. Acad. Sci. USA* 87: 9113-9117 (1990).

(56) References Cited

OTHER PUBLICATIONS

Strojek et al., "The Use of Transgenic Animal Techniques for Livestock Improvement," in: *Genetic Engineering: Principles and Methods*, vol. 10 (eds. J.K. Setlow et al.), pp. 221-246 (Plenum Press, New York, NY, 1988).
Stroop et al., "Chimeric Human Calcitonin and Glucagon Receptors Reveal Two Dissociable Calcitonin Interaction Sites," *Biochemistry* 34: 1050-1057 (1995).
Sunyaev et al., "From Analysis of Protein Structrual Alignments Toward a Novel Approach to Align Protein Sequences," *Proteins* 54: 569-582 (2004).
Suva et al., "A Parathyroid Hormone-Related Protein Implicated in Malignant Hypercalcemia: Cloning and Expression," *Science* 237: 893-896 (1987).
Szabo, "In Situ Hybridization," in: *Human Chromosomes: Manual of Basic Techniques* (eds. R.S. Verma et al.), pp. 152-165 (Pergamon Press, New York, NY,1989).
Takasu et al., "The 69-84 Amino Acid Region of the Parathyroid Hormone Molecule is Essential for the Interaction of the Hormone with the Binding Sites with Carboxyl-terminal Specificity," *Endocrinology* 137: 5537-5543 (1996).
Takasu et al., "Human PTH/PTHrP Receptors and Type-2 PTH Receptors Show Discordant Selectivity for Human PTH Analogs with Amino-Terminal Modifications," *Bone* 23:S255, Abstract No. T223 (1998).
Takasu et al., "Phospholipase C Activation via the Human PTH/PTHrP Receptor Requires an Intact Amino-Terminus of Human PTH," *Bone* 23: S447, Abstract No. F148 (1998).
Takasu et al., "Type-1 Parathyroid Hormone (PTH)/PTH-Related Peptide (PTHrP) Receptors Activate Phospholipase C in Response to Carboxyl-truncated Analogs of PTH(1-34)," *Endocrinology* 139: 4293-4299 (1998).
Takasu et al., "Amino Terminal Modifications of Human Parathyroid Hormone (PTH) Selectively Alter Phospholipase C Signaling via the Type 1 PTH Receptor: Implications for Design for Signal-Specific PTH Ligands," *Biochemistry* 38: 13453-13460 (1999).
Takasu et al., "Dual Signaling and Ligand Selectivity of the Human PTH/PTHrP Receptor," *J. Bone Miner. Res.* 14: 11-20 (1999).
Tamura et al., "Parathyroid Hormone 1-34, but not 3-34 or 7-34, Transiently Translocates Protein Kinase C in Cultured Renal (OK) Cells," *Biochem. Biophys. Res. Commun.* 159: 1352-1358 (1989).
Tan et al., "Peptide Agonist Docking in the N-Terminal Ectodomain of a Class II G Protein-Coupled Receptor, the VPAC1 Receptor. Photoaffinity, NMR, and Molecular Modeling," *J. Biol. Chem.* 281: 12792-12798 (2006).
Treanor et al., "Characterization of a Multicomponent Receptor for GDNF," *Nature* 382: 80-83 (1996).
Tregear et al., "Bovine Parathyroid Hormone: Minimum Chain Length of Synthetic Peptide Required for Biological Activity," *Endocrinology* 93: 1349-1353 (1973).
Tregear et al., "Synthetic Analogues of Residues 1-34 of Human Parathyroid Hormone: Influence of Residue No. 1 on Biological Potency in Vitro," *Endocr. Res. Commun.* 2: 561-570 (1975).
Tsomaia et al., "Cooperative Interaction of Arginine-19 and the N-Terminal Signaling Domain in the Affinity and Potency of Parathyroid Hormone," *Biochemistry* 43: 3459-3470 (2004).
Tsomaia et al., "Toward Parathyroid Hormone Minimization: Conformational Studies of Cyclic PTH(1-14) Analogues," *Biochemistry* 43: 690-699 (2004).
Turner et al., "A Putative Selectivity Filter in the G-Protein-Coupled Receptors for Parathyroid Hormone and Secretin," *J. Biol. Chem.* 271: 9205-9208 (1996).
Turner et al., "Single Mutations Allow the PTH2 Receptor to Respond to PTHrP," *J. Bone Miner. Res.* 12: S133, Abstract No. 121 (1997).
Turner et al., "Transmembrane Residues Together with the Amino Terminus Limit the Response of the Parathyroid Hormone (PTH) 2 Receptor to PTH-Related Peptide," *J. Biol. Chem.* 273: 3830-3837 (1998).
Ullrich et al., "Signal Transduction by Receptors with Tyrosine Kinase Activity," *Cell* 61: 203-212 (1990).
Unson et al., "Characterization of Deletion and Truncation Mutants of the Rat Glucagon Receptor. Seven Transmembrane Segments are Necessary for Receptor Transport to the Plasma Membrane and Glucagon Binding," *J. Biol. Chem.* 270: 27720-27727 (1995).
Ureña et al., "Regulation of Parathyroid Hormone (PTH)/PTH-Related Peptide Receptor Messenger Ribonucleic Acid by Glucocorticoids and PTH in ROS 17/2.8 and OK Cells," *Endocrinology* 134: 451-456 (1994).
Usdin et al., "Identification and Functional Expression of a Receptor Selectively Recognizing Parathyroid Hormone, the PTH2 Receptor," *J. Biol. Chem.* 270: 15455-15458 (1995).
Verma et al. "Gene Therapy—Promises, Problems and Prospects," *Nature* 389: 239-242 (1997).
Voet et al., "3. Chemical Evolution," in: *Biochemistry* (eds. D. Voet et al.), pp. 126-128 and 228-234 (Wiley, New York, NY, 1990).
Vogt et al., "An Assessment of Amino Acid Exchange Matrices in Aligning Protein Sequences: The Twilight Zone Revisited," *J. Mol. Biol.* 249: 816-831 (1995).
Wall, "Transgenic Livestock: Progress and Prospects for the Future," *Theriogenology* 45: 57-68 (1996).
Wang et al., "Rapid Analysis of Gene Expression (RAGE) Facilitates Universal Expression Profiling," *Nucleic Acids Res.* 27: 4609-4618 (1999).
Wells, "Additivity of Mutational Effects in Proteins," *Biochemistry* 29: 8509-8517 (1990).
Wells, "Hormone Mimicry," *Science* 273: 449-450 (1996).
Whitfield et al., "Restoration of Severely Depleted Femoral Trabecular Bone in Ovariectomized Rats by Parathyroid Hormone-(1-34)," *Calcif. Tissue Int.* 56: 227-231 (1995).
Whitfield et al., "Small Bone-Building Fragments of Parathyroid Hormone: New Therapeutic Agents for Osteoporosis," *Trends Pharmacol. Sci.* 16: 382-386 (1995).
Whitfield et al., "Stimulation of the Growth of Femoral Trabecular Bone in Ovariectomized Rats by the Novel Parathyroid Hormone Fragment, hPTH-(1-31)$NH_2$(Ostabolin)," *Calcif. Tissue Int.* 58: 81-87 (1996).
Whitfield et al., "Comparison of the Ability of Recombinant Human Parathyroid Hormone, rhPTH-(1-84), and hPTH-(1-31)$NH_2$ to Stimulate Femoral Trabecular Bone Growth in Ovariectomized Rats," *Calcif. Tissue Int.* 60: 26-29 (1997).
Wigley et al., "Site-Specific Transgene Insertion: An Approach," *Reprod. Fertil. Dev.* 6: 585-588 (1994).
Wittelsberger et al., "The Mid-Region of Parathyroid Hormone (1-34) Serves as a Functional Docking Domain in Receptor Activation," *Biochemistry* 45: 2027-2034 (2006).
Wrighton et al., "Small Peptides as Potent Mimetics of the Protein Hormone Erythropoietin," *Science* 273: 458-463 (1996).
Wu et al., "Structural and Physiologic Characterization of the Mid-region Secretory Species of Parathyroid Hormone-Related Protein," *J. Biol. Chem.* 271: 24371-24381 (1996).
Yamaguchi et al., "Parathyroid Hormone-Activated Calcium Channels in an Osteoblast-Like Clonal Osteosarcoma Cell Line: cAMP-Dependent and cAMP-Independent Calcium Channels," *J. Biol. Chem.* 262: 7711-7718 (1987).
Yamamoto et al., "Characterization and Agonist-Induced Down-Regulation of Parathyroid Hormone Receptors in Clonal Rat Osteosarcoma Cells," *Endocrinology* 122:1208-1217 (1988).
Yamamoto et al., "Parathyroid Hormone-Related Peptide-(1-34) [PTHrP-(1-34)] Induces Vasopressin Release from the Rat Supraoptic Nucleus In Vitro Through a Novel Receptor Distinct from a Type I or Type II PTH/PTHrP Receptor," *Endocrinology* 138: 2066-2072 (1997).
Yamamoto et al., "Centrally Administered Parathyroid Hormone (PTH)-Related Protein(1-34) but not PTH(1-34) Stimulates Arginine-Vasopressin Secretion and its Messenger Ribonucleic Acid Expression in Supraoptic Nucleus of the Conscious Rats," *Endocrinology* 139: 383-388 (1998). (Printed with erroneous vol. No. 138).

(56) References Cited

OTHER PUBLICATIONS

Yan et al., "Two-Amino Acid Molecular Switch in an Epithelial Morphogen that Regulates Binding to Two Distinct Receptors," *Science* 290: 523-527 (2000).

Yoshiko et al., "Effects of a Synthetic N-terminal Fragment of Stanniocalcin on the Metabolism of Mammalian Bone In Vitro," *Biochim. Biophys. Acta* 1311: 143-149 (1996).

Zhou et al., "Direct Mapping of an Agonist-Binding Domain within the Parathyroid Hormone/Parathyroid Hormone-Related Protein Receptor by Photoaffinity Crosslinking," *Proc. Natl. Acad. Sci. USA* 94: 3644-3649 (1997).

International Search Report for PCT/US2011/036222, mailed Oct. 21, 2011 (3 pages).

International Preliminary Report on Patentability for PCT/US2011/036222, issued Nov. 13, 2012 (8 pages).

* cited by examiner

PARATHYROID HORMONE ANALOGS AND USES THEREOF

STATEMENT AS TO FEDERALLY FUNDED RESEARCH

This invention was made with United States Government support under grant DK-11794 awarded by the National Institutes for Health. The Government has certain rights to this invention.

BACKGROUND OF THE INVENTION

In general, the invention relates to parathyroid hormone (PTH) analogs, particularly those having long-acting agonist activity at the PTH receptor. These analogs can be used to treat diseases where long-acting activity is desirable, such as hypoparathyroidism.

PTH(1-34) (SEQ ID NO:10) is an effective therapeutic in treatment of osteoporosis and conditions of PTH deficiency, namely hypoparathyroidism. Hypoparathyroidism is a lifelong disease characterized by an inadequate production of parathyroid hormone (PTH) by the parathyroid glands. Because PTH is critical for regulation of calcium and phosphate levels, loss of PTH reduces calcium levels in blood and bones and increases phosphate levels (hypocalcemia and hyperphosphatemia). Hypocalcemia leads to symptoms such as neuromuscular irritability, including paresthesias, muscle twitching, laryngeal spasms (which can lead to inability to speak and to alert health providers to the underlying medical condition, which has led to delayed or incorrect treatment), and possibly tetany and seizures. It is the only endocrine disorder in which the missing hormone (namely PTH) is not yet available as therapy.

PTH(1-34) (SEQ ID NO:10) has been identified as a safe and effective alternative to calcitriol therapy for hypoparathyroidism and is able to maintain normal serum calcium levels without hypercalciuria (Winer et al., J Clin Endocrinol Metab 88:4214-4220, 2003). Nonetheless, the polypeptide requires injection at least twice daily, and the need in this disease for a long-acting PTH(1-34) (SEQ ID NO:10) analog has therefore been recognized (Winer et al., supra).

Thus, there exists a need for additional PTH receptor agonists, particularly those having long-acting activity at the PTH receptor.

SUMMARY OF THE INVENTION

The present invention relates to the development of PTH and PTHrP analogs. The exemplary polypeptides described herein, SP-PTH-AAK (SEQ ID NO:4) and Aib-SP-PTH-AAK (SEQ ID NO:5), have long-acting activity at the PTH receptor both in vitro and in vivo and exhibit high solubility in neutral aqueous solution. The polypeptides of the invention are therefore suitable for treatment of disease in which long-acting activity is desired, including hypoparathyroidism.

The invention accordingly features a polypeptide (e.g., isolated), or pharmaceutically acceptable salt thereof, including the amino acid sequence of formula (I):

(I) (SEQ ID NO: 1)
$X_{01}$-Val-$X_{03}$-Glu-Ile-Gln-Leu-$X_{08}$-His-$X_{10}$-$X_{11}$-$X_{12}$-$X_{13}$-

$X_{14}$-$X_{15}$-$X_{16}$-$X_{17}$-$X_{18}$-Arg-Arg-Arg-$X_{22}$-Phe-Leu-$X_{25}$-$X_{26}$-

Leu-Ile-Ala-Glu-Ile-His-Thr-Ala-Glu-Ile where $X_{01}$ is Ser, Ala, or Aib; $X_{03}$ is Ser, Ala, or Aib; $X_{08}$ is Met, Leu, or Nle; $X_{10}$ is Asn, Ala, Val, Asp, Ile, Glu, or Gln; $X_{11}$ is Leu, Ala, Val, Met, Lys, Arg, Har, or Trp; $X_{12}$ is Gly, Ala, His, or Arg; $X_{13}$ is Lys, Ala, Leu, Gln, Arg, His, or Trp; $X_{14}$ is His, Leu, Arg, Phe, Trp, or Ser; $X_{15}$ is Ile or Leu; $X_{16}$ is Gln or Asn; $X_{17}$ is Asp or Ser; $X_{18}$ is Ala, Leu, Met, Glu, Ser, or Phe; $X_{22}$ is Ala, Phe, Glu, Ser, Leu, Asn, Trp, or Lys; $X_{25}$ is His, Arg, Leu, Trp, or Lys; and $X_{26}$ is Lys, His, Ala, Ser, Asn, or Arg; or a fragment thereof including amino acids 1-28, 1-29, 1-30, 1-31, 1-32, 1-33, 1-34, or 1-35 of formula (I), with the proviso that at least one of $X_{18}$ is not Leu or Met, $X_{22}$ is not Phe, and $X_{26}$ is not His.

In certain embodiments, the polypeptide includes formula (II):

(II) (SEQ ID NO: 2)
$X_{01}$-Val-$X_{03}$-Glu-Ile-Gln-Leu-$X_{08}$-His-$X_{10}$-$X_{11}$-$X_{12}$-Lys- $X_{14}$-$X_{15}$-$X_{16}$-$X_{17}$-$X_{18}$-Arg-Arg-Arg-$X_{22}$-Phe-Leu-His-$X_{26}$-

Leu-Ile-Ala-Glu-Ile-His-Thr-Ala-Glu-Ile where $X_{01}$ is Ser, Ala, or Aib; $X_{03}$ is Ser, Ala, or Aib; $X_{08}$ is Met, Leu, or Nle; $X_{10}$ is Asn, Gln, or Asp; $X_{11}$ is Leu, Arg, Har, or Lys; $X_{12}$ is Gly or Ala; $X_{14}$ is His, Trp, or Ser; $X_{15}$ is Ile or Leu; $X_{16}$ is Gln or Asn; $X_{17}$ is Asp or Ser; $X_{18}$ is Ala or Leu; $X_{22}$ is Ala or Phe; and $X_{26}$ is Lys or His; or a fragment thereof including amino acids 1-28, 1-29, 1-30, 1-31, 1-32, 1-33, 1-34, or 1-35 of formula (II).

In other embodiments, the polypeptide includes formula (III):

(III) (SEQ ID NO: 3)
$X_{01}$-Val-$X_{03}$-Glu-Ile-Gln-Leu-$X_{08}$-His-$X_{10}$-$X_{11}$-$X_{12}$-Lys- $X_{14}$-Ile-$X_{16}$-$X_{17}$-$X_{18}$-Arg-Arg-Arg-$X_{22}$-Phe-Leu-His-$X_{26}$-

Leu-Ile-Ala-Glu-Ile-His-Thr-Ala-Glu-Ile where $X_{01}$ is Ser, Ala, or Aib; $X_{03}$ is Ser, Ala, or Aib; $X_{08}$ is Met, Leu, or Nle; $X_{10}$ is Asn or Gln; $X_{11}$ is Leu, Arg, or Har; $X_{12}$ is Gly or Ala; $X_{14}$ is His or Trp; $X_{16}$ is Gln or Asn; $X_{17}$ is Asp or Ser; $X_{18}$ is Ala or Leu; $X_{22}$ is Ala or Phe; and $X_{26}$ is Lys or His; or a fragment thereof including amino acids 1-28, 1-29, 1-30, 1-31, 1-32, 1-33, 1-34, or 1-35 of formula (III).

In particular embodiments of any of the above polypeptides, $X_{01}$ and $X_{03}$ are Ala; $X_{10}$ is Gln; $X_{11}$ is Arg; $X_{12}$ is Ala; and $X_{14}$ is Trp. In other embodiments, $X_{01}$ is Ala; $X_{03}$ is Aib; $X_{10}$ is Gln; $X_{11}$ is Har; $X_{12}$ is Ala; and $X_{14}$ is Trp. In any of the above polypeptides, $X_{18}$ may be Ala; $X_{22}$ may be Ala; and/or $X_{26}$ may be Lys.

In certain embodiments, the polypeptide is substantially identical (e.g., at least 90% or 95% identical) to a polypeptide described above (e.g., where $X_{18}$ and $X_{22}$ are Ala and where $X_{26}$ is Lys). In certain embodiments, the polypeptide exhibits greater solubility in neutral aqueous solution (e.g., phosphate-buffered saline (PBS) at pH 7.4) as compared to SP-PTH (e.g., is at least 40%, 50%, 60%, 70%, 80%, 90%, or 95% as soluble in neutral aqueous solution as compared to in acidic solution (e.g., pH 1, 2, 3, 4 such as 10 mM acetic acid (pH 2.9)). In certain embodiments, the polypeptide is biologically active (e.g., a PTH receptor agonist). In certain embodiments, the polypeptide binds to the $R^0$ state of the human PTH-1 receptor with an affinity greater than that of hPTH(1-34). In other embodiments, the polypeptide is fewer than 200, 150, 100, 75, 50, 40, 39, 38, or 37 amino acids in length. The polypeptide may be amidated at its C-terminus.

In a particular embodiment, the polypeptide includes or is the amino acid sequence:

```
                                       (SEQ ID NO: 4)
Ala-Val-Ala-Glu-Ile-Gln-Leu-Met-His-Gln-Arg-Ala-

Lys-Trp-Ile-Gln-Asp-Ala-Arg-Arg-Arg-Ala-Phe-Leu-

His-Lys-Leu-Ile-Ala-Glu-Ile-His-Thr-Ala-Glu-Ile,
``` or a fragment thereof including amino acids 1-28, 1-29, 1-30, 1-31, 1-32, 1-33, 1-34, or 1-35 of said sequence. In another embodiment, the polypeptide includes or is the amino acid sequence:

```
                                       (SEQ ID NO: 5)
Ala-Val-Aib-Glu-Ile-Gln-Leu-Met-His-Gln-Har-Ala-

Lys-Trp-Ile-Gln-Asp-Ala-Arg-Arg-Arg-Ala-Phe-Leu-

His-Lys-Leu-Ile-Ala-Glu-Ile-His-Thr-Ala-Glu-Ile,
``` or a fragment thereof including amino acids 1-28, 1-29, 1-30, 1-31, 1-32, 1-33, 1-34, or 1-35 of said sequence. In other embodiments, the peptide includes or is an amino acid sequence is selected from the group consisting of:

```
                                       (SEQ ID NO: 6)
Ala-Val-Ala-Glu-Ile-Gln-Leu-Nle-His-Gln-Arg-Ala-

Lys-Trp-Ile-Gln-Asp-Ala-Arg-Arg-Arg-Ala-Phe-Leu-

His-Lys-Leu-Ile-Ala-Glu-Ile-His-Thr-Ala-Glu-Ile;

(SEQ ID NO: 7)
Ala-Val-Ala-Glu-Ile-Gln-Leu-Leu-His-Gln-Arg-Ala-

Lys-Trp-Ile-Gln-Asp-Ala-Arg-Arg-Arg-Ala-Phe-Leu-

His-Lys-Leu-Ile-Ala-Glu-Ile-His-Thr-Ala-Glu-Ile;

(SEQ ID NO: 8)
Ala-Val-Aib-Glu-Ile-Gln-Leu-Nle-His-Gln-Har-Ala-

Lys-Trp-Ile-Gln-Asp-Ala-Arg-Arg-Arg-Ala-Phe-Leu-

His-Lys-Leu-Ile-Ala-Glu-Ile-His-Thr-Ala-Glu-Ile;
and
                                       (SEQ ID NO: 9)
Ala-Val-Aib-Glu-Ile-Gln-Leu-Leu-His-Gln-Har-Ala- Lys-Trp-Ile-Gln-Asp-Ala-Arg-Arg-Arg-Ala-Phe-Leu- His-Lys-Leu-Ile-Ala-Glu-Ile-His-Thr-Ala-Glu-Ile,
``` or a fragment thereof including amino acids 1-28, 1-29, 1-30, 1-31, 1-32, 1-33, 1-34, or 1-35 of said sequence.

Any of the polypeptides described above may be amidated at their C-terminus.

The invention also features a pharmaceutical composition that includes a polypeptide of the invention (e.g., any polypeptide described above or herein) and a pharmaceutically acceptable carrier.

In certain embodiments, the polypeptide of the invention is synthesized by solid-phase synthesis or is produced recombinantly.

The invention also features a method for treating a subject having a disease selected, for example, from the group consisting of hypoparathyroidism, hyperphosphatemia, osteoporosis, fracture repair, osteomalacia, arthritis, and thrombocytopenia. The method includes administering a polypeptide of the invention or a pharmaceutical composition including a polypeptide of the invention to the subject in an amount sufficient to treat the disease. The polypeptide or pharmaceutical composition may be administered, for example, subcutaneously, intravenously, intranasally, transpulmonarily, transdermally, and orally.

The invention also features a nucleic acid including a sequence encoding a polypeptide of the invention. The nucleic acid may be operably linked to a promoter. The nucleic acid may be part of a vector. The invention also features a cell including the vector and a method of making a polypeptide by growing the cell under conditions where the encoded polypeptide is expressed.

By "subject" is meant either a human or non-human animal (e.g., a mammal).

By "treating" is meant ameliorating at least one symptom of a condition or disease in a subject having the condition or disease (e.g., a subject diagnosed with hypoparathyroidism), as compared with an equivalent untreated control. Such reduction in the symptom (e.g., a reduction in blood calcium levels or increase in serum phosphate levels) is at least 5%, 10%, 20%, 40%, 50%, 60%, 80%, 90%, 95%, or 100%, as measured by any standard technique.

By a "purified polypeptide" or "isolated polypeptide" is meant a polypeptide that has been separated from other components. Typically, the polypeptide is substantially pure when it is at least 30%, by weight, free from other components. In certain embodiments, the preparation is at least 50%, 60%, 75%, 85%, 90%, 95%, 96%, 97%, 98%, or 99% by weight, free from other components. A purified polypeptide may be obtained, for example, by extraction from a natural source; by expression of a recombinant polynucleotide encoding such a polypeptide; or by chemically synthesizing the polypeptide. Purity can be measured by any appropriate method, for example, column chromatography, polyacrylamide gel electrophoresis, or by HPLC analysis.

By "biologically active" is meant that the compound or composition (e.g., a polypeptide described herein) has at least one biologically significant effect upon administration to a cell or animal (e.g., a human or non-human mammal). Biological activities of PTH, PTHrP, and analogs thereof (e.g., those described herein) include, without limitation, receptor binding, cAMP or $IP_3$ production, protein kinase A, protein kinase C, phospholipase C, phospholipase D, and phospholipase $A_2$ activation, changes (e.g., increases or decreases) in intracellular, plasma, or urinary calcium or phosphate levels, and changes in bone metabolism or catabolism in vivo or in vitro. A biologically active polypeptide of the invention (e.g., any polypeptide described herein), for example, may exhibit increases (e.g., at least 5%, 10%, 25%, 50%, 100%, 500%, 1000%, 10,000%) or decreases (e.g., 95%, 90%, 75%, 50%, 25%, 10%, 5%, 1%, 0.1%, 0.01%, or 0.001%) in any biological activity as compared to an appropriate control (e.g., a wild-type polypeptide or a phenocopy thereof such as PTH(1-34) (SEQ ID NO:10) or PTHrP(1-36) (SEQ ID NO:14)).

By "substantially identical" is meant a nucleic acid or amino acid sequence that, when optimally aligned, for example, using the methods described below, share at least 60%, 65%, 70%, 75%, 80%, 85%, 90%, 95%, 96%, 97%, 98%, 99% or 100% sequence identity with a second nucleic acid or amino acid sequence, e.g., a PTH or PTHrP sequence or fragment thereof. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith et al., J Mol Biol 147:195-7, 1981); "Best Fit" (Smith and Waterman, Advances in Applied Mathematics, 482-489, 1981) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul et al., J Mol Biol 215: 403-10, 1990), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 6 or 8 amino acids, preferably 9, 10, 11, 12, 13, 14, 15, 16, 17, 18, 19, 20, 21, 22, 23, 24, 25, 26, 27, 28, 29, 30, 31, 32, 33, 34, 35, 36, 40, 50, 60, 70, 80, 90, 100, 125, 150, 200, 250, 300, 350, 400, or 500 amino acids or more up to the entire length of the protein. For nucleic acids, the length of comparison sequences will generally be at least 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 125, 150, 200, 250, 300, 350, 400, 450, 500, 550, 600, 650, 700, 800, 900, 1000, 1100, 1200, or at least 1500 nucleotides or more up to the entire length of the nucleic acid molecule. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "neutral pH" is meant a pH of about 6-9 (e.g., 6.5-8.0). Particular neutral pH values include 6.5, 6.6, 6.8, 7.0, 7.2, 7.4, 7.6, 7.8, and 8.0.

Other features and advantages of the invention will be apparent from the following Detailed Description, the drawings, and the claims.

BRIEF DESCRIPTION OF THE DRAWINGS

FIG. 7A shows cAMP generation in pmol/well, and FIG. 7B shows these results normalized to the maximal cAMP stimulation for each ligand.

FIGS. 12A and 12B show results using 0.25 nmol/kg of SP-PTH (SEQ ID NO:11) or SP-PTH-AAK (SEQ ID NO:4), or vehicle control injected intravenously. FIG. 12C shows serum calcium concentrations following a 40-fold increased dose (10 nmol/kg) of PTH(1-34) (SEQ ID NO:10) injected subcutaneously.

FIG. 15A shows serum calcium levels, and FIGS. 15B and 15C show serum inorganic phosphate levels. FIG. 15D shows serum creatinine levels. FIGS. 15E and 15G show urine calcium levels, and FIGS. 15F and 15H shown urine phosphate levels.

DETAILED DESCRIPTION

Figure 1A:
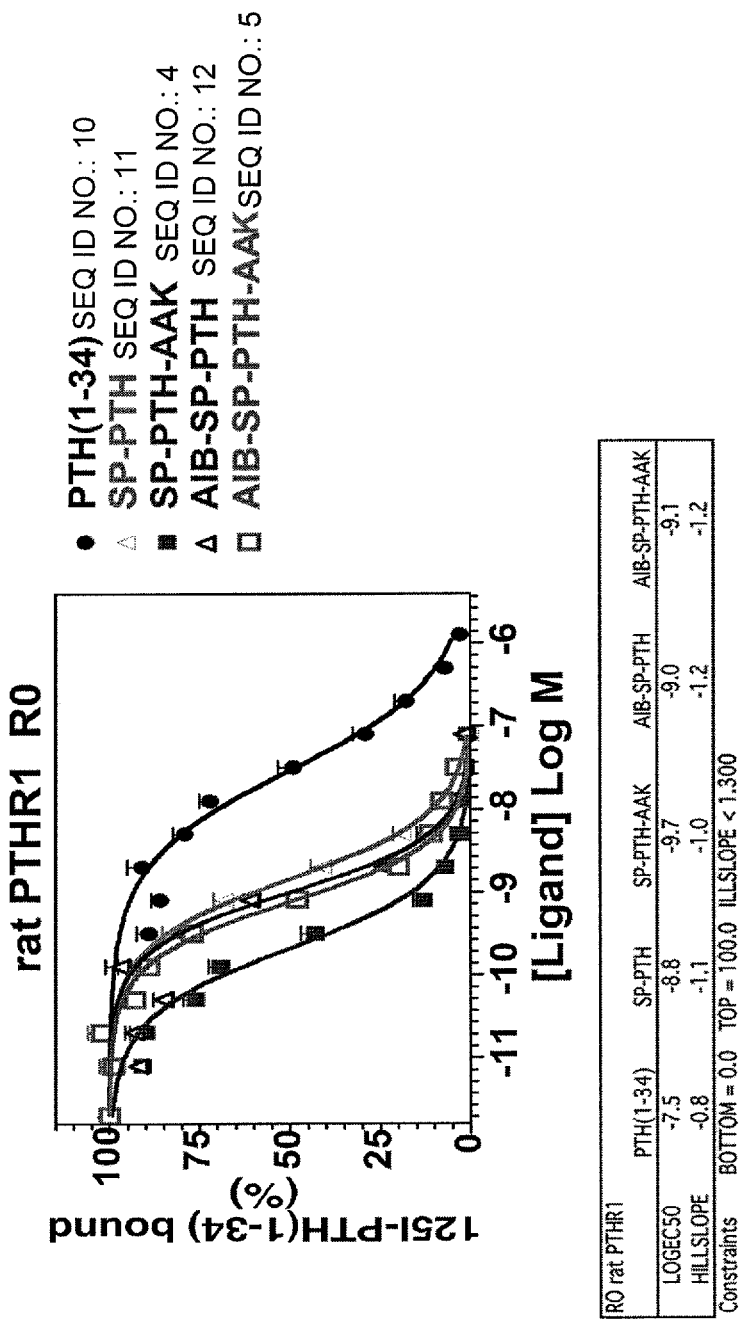
FIGS. 1A and 1B are graphs showing binding affinities of PTH analogs for the rat PTHR1 conformations in $R^0$ (FIG. 1A) and RG (FIG. 1B). As shown, SP-PTH-AAK (SEQ ID NO:4) exhibited the strongest binding to both the $R^0$ and RG forms of the receptor. PTH(1-34) (SEQ ID NO:10) exhibited the weakest binding to the $R^0$ form of the receptor. Curve fit parameters are shown below each graph.

The present invention relates to new parathyroid hormone (PTH) analogs having prolonged activity at the PTH receptor. These analogs are exemplified by SP-PTH-AAK (SEQ ID NO:4) ([Ala$^{1,3,12,18,22}$,Gln$^{10}$,Arg$^{11}$,Trp$^{14}$,Lys$^{26}$]PTH(1-14)/PTHrP(15-36)) and Aib-SP-PTH-AAK (SEQ ID NO:5) ([Ala$^{1,12,18,22}$,Aib$^3$,Gln$^{10}$,homoArg$^{11}$,Trp$^{14}$,Lys$^{26}$]PTH(1-14)/PTHrP(15-36)). As described below, these polypeptides bind with higher affinity to the non-G protein coupled, R$^0$ conformation of the PTH-1 receptor (PTHR1) in vitro than PTH(1-34) (SEQ ID NO:10) and other reference polypeptides. Accordingly, these polypeptides induce prolonged cAMP signaling responses in cultured cells. These polypeptides also exhibited prolonged increases in blood ionized calcium levels in laboratory test animals (mice, rats, and monkeys) as compared to PTH(1-34) (SEQ ID NO:10) or other test analogs. Because of their confirmed long-acting properties in vivo, the analogs have utility as treatments for conditions such as hypoparathyroidism.

The exemplary polypeptides, SP-PTH-AAK (SEQ ID NO:4) and Aib-SP-PTH-AAK (SEQ ID NO:5), include an N-terminal portion based on the human PTH(1-14) sequence and a C-terminal portion based on the human PTHrP sequence (see Table 1 below), with both the N- and C-terminal portions containing affinity-enhancing amino-acid substitutions. These polypeptides exhibit surprisingly high binding affinities and cAMP signaling potencies in vitro, as well as enhanced functional effects in vivo, as illustrated in the Examples below. Finally, these polypeptides exhibited high solubility, comparable to the wild-type PTH(1-34) (SEQ ID NO:10) polypeptide, as described below. Based on these properties, these polypeptides can be used in any application where prolonged activity at the PTH receptor is desired, e.g., for the treatment of hypoparathyroidism.

R$^0$ vs. RG Binding of PTH Agonists

As described in PCT Publication WO 2009/017809, a novel "R$^0$" state of the PTH receptor, in which the receptor is not bound to its G-protein but is capable of agonist binding was identified. Previously it was believed that two forms of a G-protein-coupled receptor could be distinguished: a form (RG) that is bound to a G-protein and a form (R) that is not bound to a G-protein. GPCR signaling requires that the G-protein be directly activated by the receptor, i.e., the RG state must form, and this RG formation can be induced by binding of an agonist ligand. Binding of an agonist ligand induces or stabilizes the RG state, and reciprocally, the RG state stabilizes the high affinity binding of an agonist. Upon binding GTP, or, a non-hydrolyzable GTP analog, such as GTPγS, a receptor-coupled G protein will dissociate from the receptor, causing the receptor to revert to a low affinity state. It is now recognized that some GPCRs, like the PTHR, can form a novel state)(R$^0$ that can bind certain agonist ligands with high affinity even in the presence of GTPγS, and hence, even when the receptor is presumably not bound by a G protein. Based on this discovery of the R$^0$ state, PCT Publication WO 2009/017809 describes that ligands which bind with high affinity to the R$^0$ state, in addition to the RG state, have a longer activity half-life than ligands that bind to R$^0$ with lower affinity. This prolonged activity does not depend on the bioavailability or the pharmacokinetics of the ligand in vivo. Correspondingly, agonists with a short duration of action have a lower affinity for the R$^0$ form of the receptor.

As described in the Examples below, SP-PTH-AAK (SEQ ID NO:4) and Aib-SP-PTH-AAK (SEQ ID NO:5) exhibit substantially greater binding to the R$^0$ form of the PTH receptor as compared to hPTH(1-34) (SEQ ID NO:10) in vitro, and exhibit long-acting activity both in vitro and in vivo. The polypeptides of the invention are therefore suitable as long-acting PTH agonists.

Making Polypeptides of the Invention

The polypeptides of the invention (e.g., SP-PTH-AAK (SEQ ID NO:4) and Aib-SP-PTH-AAK (SEQ ID NO:5)) are amenable to production by solution- or solid-phase peptide synthesis and by in-situ synthesis using combination chemistry. The solid phase peptide synthesis technique, in particular, has been successfully applied in the production of human PTH and can be used for the production of these compounds (for guidance, see Kimura et al., supra and Fairwell et al., Biochem. 22:2691, 1983). Success with producing human PTH on a relatively large scale has been reported in Goud et al., J Bone Min Res 6:781, 1991. The synthetic peptide synthesis approach generally entails the use of automated synthesizers and appropriate resin as solid phase, to which is attached the C-terminal amino acid of the desired polypeptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," $2^{nd}$ Edition, Pierce Chemical Company, Rockford, Ill. (1984).

Polypeptides of the invention can also be made recombinantly by any method known in the art. Prokaryotic (e.g., bacterial) and eukaryotic (e.g., yeast and mammalian) expression systems can also be used to produce polypeptides of the invention, particularly where the polypeptide includes only amino acids coded for the genome (e.g., not Aib or Har).

Polypeptide Modifications

Any of the polypeptides described herein (e.g., SP-PTH-AAK (SEQ ID NO:4) and Aib-SP-PTH-AAK (SEQ ID NO:5)) may contain one or more modifications such as N-terminal or C-terminal modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as aiginylation, and ubiquitination. See, for instance, Proteins-Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Methods Enzymol 182:626 646 (1990) and Rattan et al., Ann NY Acad Sci 663A& 62 (1992).

Any of the polypeptides of the invention may further include a heterologous sequence (a fusion partner), thus forming a fusion protein. The fusion protein may include a fusion partner such as a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence). In other embodiments the fusion partner may be a tag, such as c-myc, poly histidine, or FLAG. Each fusion partner may contain one or more domains, e.g., a preprotrypsin signal sequence and FLAG tag. In other cases, the fusion partner is an Fc protein (e.g., mouse Fc or human Fc).

Methods for Treatment of Disease

Any disease associated with PTH dysfunction or with calcium or phosphate imbalances, can be treated with the polypeptides described herein (e.g., SP-PTH-AAK (SEQ ID NO:4) and Aib-SP-PTH-AAK (SEQ ID NO:5)). The polypeptides may be used to treat hypoparathyroidism, hyperphosphatemia, osteoporosis, fracture repair, osteomalacia, arthritis, or thrombocytopenia, or may be used to increase stem cell mobilization in a subject. Any mode of administration (e.g., oral, intravenous, intramuscular, ophthalmic, topical, dermal, subcutaneous, and rectal) can be used in the treatment methods of the invention. A physician will determine appropriate dosing for the patient being treated, which will depend in part on the age and size of the patient, the severity of the disease or condition, and the particular disease or condition being treated.

Formulation of Pharmaceutical Compositions

The administration of any polypeptide described herein (e.g., SP-PTH-AAK (SEQ ID NO:4) and Aib-SP-PTH-AAK (SEQ ID NO:5)) may be by any suitable means that results in a concentration of the compound that treats the subject and disease condition. The polypeptide may be contained in any appropriate amount in any suitable carrier substance, and is generally present in an amount of 1-95% by weight of the total weight of the composition. The composition may be provided in a dosage form that is suitable for the oral, parenteral (e.g., intravenously or intramuscularly), rectal, cutaneous, nasal, vaginal, inhalant, skin (patch), ocular, or intracranial administration route. Thus, the composition may be in the form of, e.g., tablets, ampules, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, $20^{th}$ edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Pharmaceutical compositions may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the compound to a particular target cell type. Administration of the compound in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, molecular complexes, microspheres, nanoparticles, patches, and liposomes.

Parenteral Compositions

The composition containing polypeptides described herein (e.g., SP-PTH-AAK (SEQ ID NO:4) and Aib-SP-PTH-AAK (SEQ ID NO:5)) may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The following examples are intended to illustrate rather than limit the invention.

Example 1

Polypeptide Synthesis

Exemplary peptides [Ala$^{1,12}$,Aib$^3$,Gln$^{10}$,Har$^{11}$,Trp$^{14}$]PTH(1-14)/PTHrP(15-36) (Super-potent Aib-PTH: Aib-SP-PTH) (SEQ ID NO:12) and [Ala$^{1,12,18,22}$,Aib$^3$,Gln$^{10}$,Har$^{11}$,Trp$^{14}$,Lys$^{26}$]PTH(1-14)/PTHrP(15-36) (Super-potent Aib-AAK PTH: Aib-SP-PTH-AAK) (SEQ ID NO:5) were synthesized by the Massachusetts General Hospital Biopolymer Core facility. Aib and Har represent α-aminoisobutyric acid and homoarginine, respectively.

Exemplary peptides [Ala$^{1,3,12}$,Gln$^{10}$,Arg$^{11}$,Trp$^{14}$]PTH(1-14)/PTHrP(15-36) (Super-potent PTH: SP-PTH) (SEQ ID NO:11) and [Ala$^{1,3,12,18,22}$,Gln$^{10}$,Arg$^{11}$,Trp$^{14}$,Lys$^{26}$]PTH(1-14)/PTHrP(15-36) (SP-PTH-AAK) (SEQ ID NO:4) were synthesized by Sigma Aldrich (Hokkaido, Japan) and American Peptide Company, Inc. (Calif., USA). All polypeptides were dissolved in 10 mM acetic acid and stored at −80° C. Polypeptide concentrations were determined using the PACE method (Pace et al., Protein Science 4:2411-23, 1995) or by amino acid analysis.

Each of these polypeptides is shown in Table 1 below.

TABLE 1

Polypeptides

| MGH # | Short name | Chemical name | M.W. | Sequence |
|---|---|---|---|---|
| 1219 | PTH(1-34) | hPTH(1-34)OH | 4117 | SVSEIQLMHNLGKHLNSMERVEWLRKKLQDVHNF.OH (SEQ ID NO: 10) |
| 1161, 1646 | SP-PTH | Mc-PTH(1-14)/rP(15-36)OH | 4392 | AVAEIQLMHQRAKWIQDLRRRFFLHHLIAEIHTAEI.OH (SEQ ID NO: 11) |
| 1650 | SP-PTH-AAK | Mc-PTH(1-14)/AAK-rP(15-36)OH | 4265 | AVAEIQLMHQRAKWIQDARRRAFLHKLIAEIHTAEI.OH (SEQ ID NO: 4) |
| 1450, 1705 | Aib-SP-PTH | M-PTH(1-14)/rP(15-36)NH2 | 4421 | AVAibEIQLMHQHarAKWIQDLRRRFFLHHLIAEIHTAEI.NH2 (SEQ ID NO: 12) |
| 1439, 1704 | Aib-SP-PTH-AAK | M-PTH(1-14)AAK-/rP(15-36)NH2 | 4294 | AVAibEIQLMHQHarAKWIQDARRRAFLHKLIAEIHTAEI.NH2 (SEQ ID NO: 5) |
| 1577 | M-PTH(1-34) | M-PTH(1-34).NH2 | 4261 | AVAibEIQLMHQHarAKWLNSMRRVEWLRKKLQDVHNF.NH2 (SEQ ID NO: 13) |
| 1366, 1423 | PTHrP(1-36) | hPTHrP(1-36)OH | 4260 | AVSEHQLLHDKGKSIQDLRRRFFLHHLIAEIHTAEI.OH (SEQ ID NO: 14) |
| 1457 | PTH(3-34) | [Nle8, 18, Y34] bPTH(3-34)NH2 | 3912 | SEIQFNleHNLGKHLSSnleERVEWLRKKLQDVHNY.NH2 (SEQ ID NO: 15) |

TABLE 1-continued

Polypeptides

| MGH # | Short name | Chemical name | M.W. | Sequence |
|---|---|---|---|---|
| | Nle8-SP-PTH-AAK | Nle8, Mc-PTH(1-14)/AAK-rP(15-36)NH2 | 4265 | AVAEIQLNleHQRAKWIQDARRRAFLHKLIAEIHTAEI.NH2 (SEQ ID NO: 6) |
| | L8-SP-PTH-AAK | L8, Mc-PTH(1-14)/AAK-rP(15-36)NH2 | 4265 | AVAEIQLLHQRAKWIQDARRRAFLHKLIAEIHTAEI.NH2 (SEQ ID NO: 7) |
| | Nle8-Aib-SP-PTH-AAK | Nle8, M-PTH(1-14)AAK-/rP(15-36)NH2 | 4294 | AVAibEIQLNleHQHarAKWIQDARRRAFLHKLIAEIHTAEI.NH2 (SEQ ID NO: 8) |
| | L8-Aib-SP-PTH-AAK | L8, M-PTH(1-14)AAK-/rP(15-36)NH2 | 4294 | AVAibEIQLLHQHarAKWIQDARRRAFLHKLIAEIHTAEI.NH2 (SEQ ID NO: 9) |

Mc residues: $Ala^{1,3,12}$, $Gln^{10}$, $Arg^{11,19}$, $Trp^{14}$
M residues: $Ala^{1,12}$, $Aib^3$, $Gln^{10}$, $homoArg^{11}$, $Trp^{14}$, $Arg^{19}$ Example 2

Characterization—R⁰/RG Binding and cAMP Potency

Binding of PTH(1-34) (SEQ ID NO:10), SP-PTH (SEQ ID NO:11), SP-PTH-AAK (SEQ ID NO:4), Aib-SP-PTH (SEQ ID NO:12), and Aib-SP-PTH-AAK (SEQ ID NO:5) to the R⁰ and RG forms of the PTH-1 receptor was measured using a method as described in PCT Publication WO 2009/017809 or a similar method. Briefly, the R⁰ form of the receptor can be favored by addition of the non-hydrolyzable nucleotide analog GTPγS. The RG form can be favored, for example, by co-transfection of cells with a negative dominant $G\alpha_s$ subunit. Binding is measured based on displacement of a radioactive tracer ligand ($^{125}$I-PTH(1-34)). As shown in FIG. 1A, the four tested polypeptides exhibited about 1-2 orders of magnitude stronger binding to the R⁰ form of the rat PTH receptor as compared to PTH(1-34) (SEQ ID NO:10). In particular SP-PTH-AAK (SEQ ID NO:4) exhibited a greater than two orders of magnitude increase in binding (log $EC_{50}$ of −9.7 vs. −7.5 for PTH(1-34) (SEQ ID NO:10)). Data are means of four experiments, each performed in duplicate. Curves were fit to the data using Graph-Pad Prism 4.0. The inset in each figure shows the fit parameters.

Figure 1B:
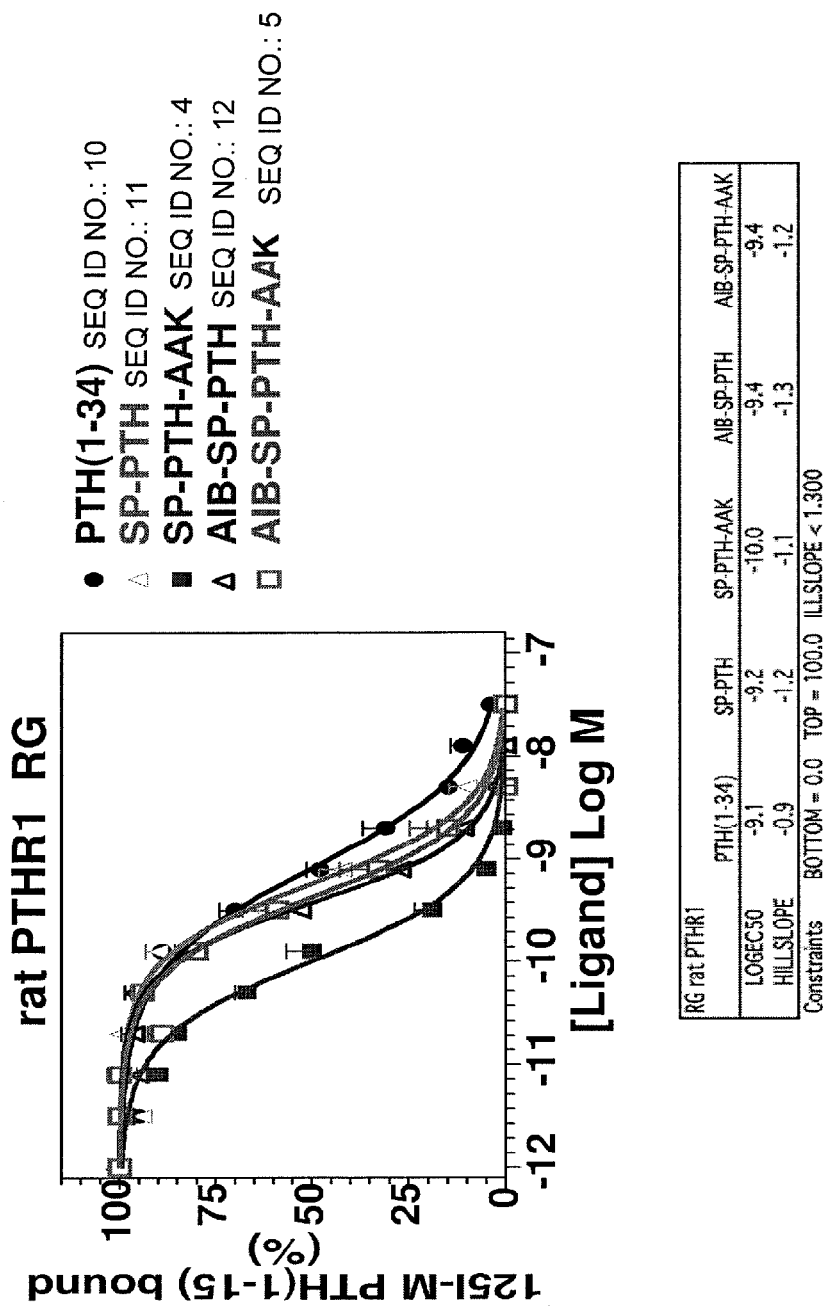
Figure 2:
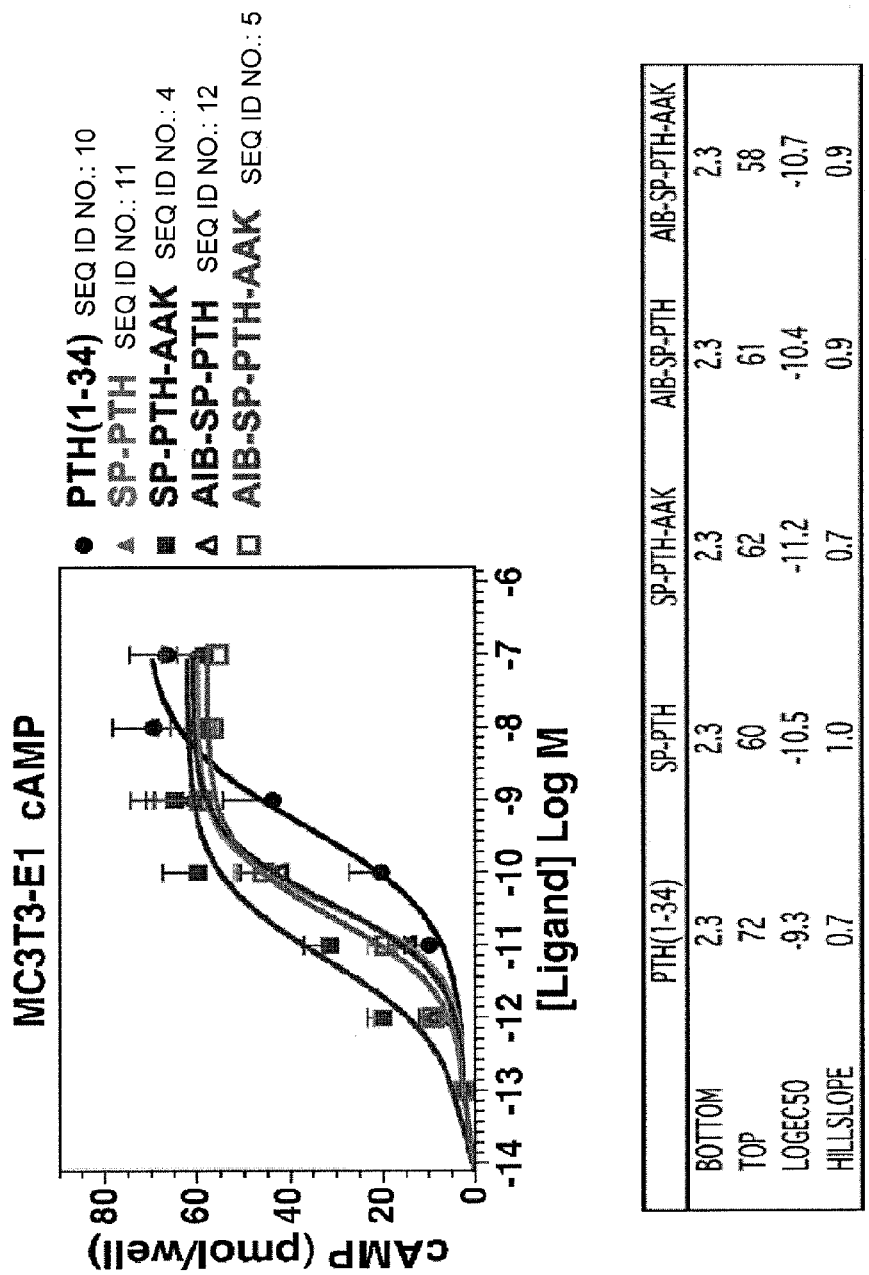
FIG. 2 is a graph showing cAMP responses to PTH(1-34) (SEQ ID NO:10), SP-PTH (SEQ ID NO:11), SP-PTH-AAK (SEQ ID NO:4), Aib-SP-PTH (SEQ ID NO:12), and Aib-SP-PTH-AAK (SEQ ID NO:5) in MC3T3-E1 cells. Curve fit parameters are shown below each graph.
Figure 3:
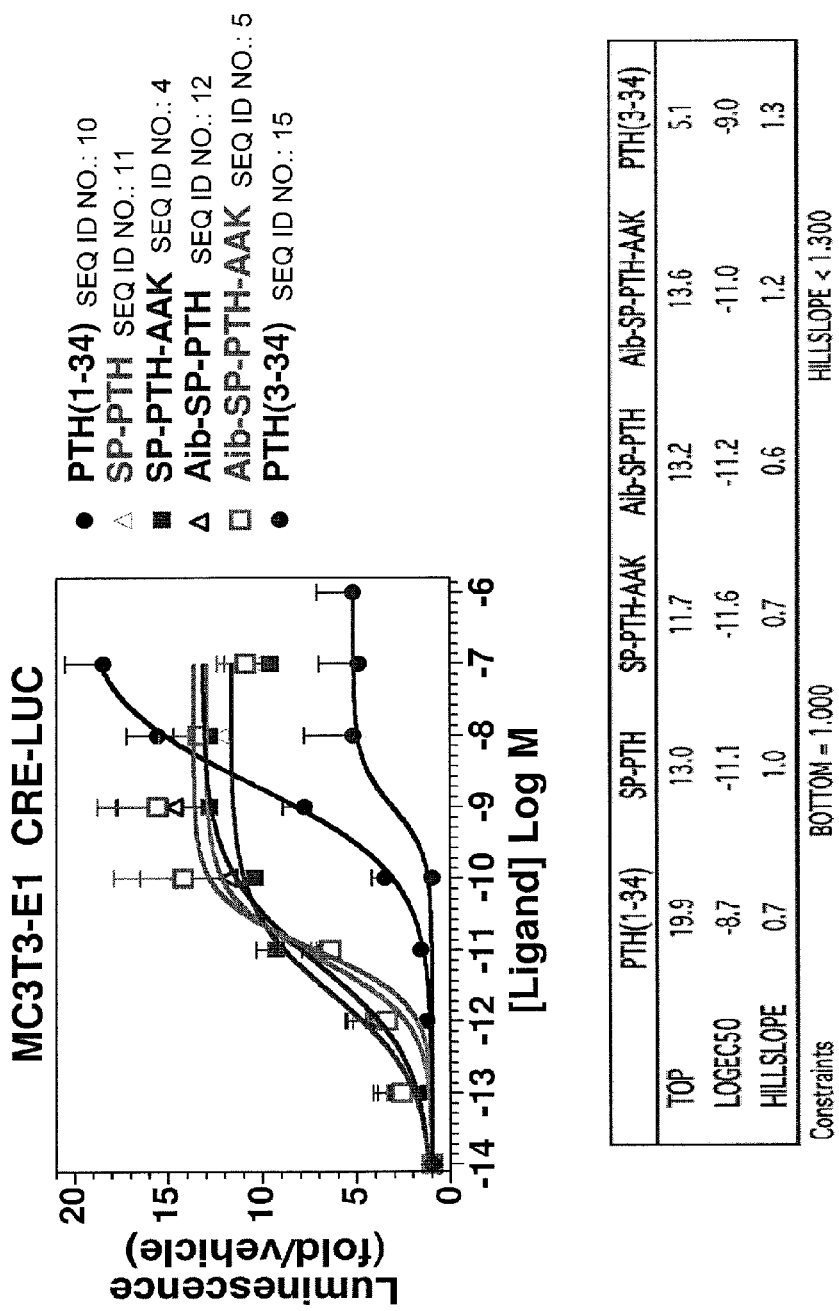
FIG. 3 is a graph showing luminescence in MC3T3-E1 cells transfected with a cAMP-response element-luciferase gene construct following treatment with PTH(1-34) (SEQ ID NO:10), SP-PTH (SEQ ID NO:11), SP-PTH-AAK (SEQ ID NO:4), Aib-SP-PTH (SEQ ID NO:12), Aib-SP-PTH-AAK (SEQ ID NO:5), or PTH(3-34) (SEQ ID NO:15). Curve fit parameters are shown below the graph.

RG binding at the rat PTH receptor was also increased in SP-PTH-AAK (SEQ ID NO:4) and Aib-SP-PTH-AAK (SEQ ID NO:5) as compared to hPTH(1-34) (SEQ ID NO:10) (FIG. 1B).

cAMP stimulating activity of these polypeptides was also assessed, using two different methods: a radioimmunoassay (RIA; FIG. 2) and a cAMP responsive element fused to a luciferase gene (FIG. 3). Briefly, the RIA cAMP assays were performed in intact MC3T3-E1 cells, a mouse pre-osteoblastic cell line, in 96-well plates, as described by Okazaki et al. (Proc Natl Acad Sci USA 105:16525-30, 2008). Cells were treated with the indicated ligand at varying concentrations (−12 to −6 log M) for 30 minutes at room temperature in the presence of IBMX, after which the buffer was removed, and the reactions were terminated by addition of 50 mM HCl. The cAMP contents of the HCl lysates were then determined by RIA. Data are means of six experiments, each performed in duplicate. Curves were fit to the data using Graph-Pad Prism 4.0. The inset shows the fit parameters for each curve.

The cAMP-response-element-luciferase response was measured as follows. MC3T3-E1 cells were transfected in 96-well plates with plasmid DNA encoding a luciferase gene fused to a cAMP-Response Element (CRE) promoter, a plasmid construct designed to assess signaling via the cAMP/PKA pathway. At 48 hours after transfection, the cells were incubated at 37° C. for four hours in media containing either vehicle (−14 log M on plot abscissa) or varying concentrations (−13 to −6 log M) of the indicated ligand. Luciferase activity, as luminescence, was then measured using the Promega Steady-Glo reagent and a Perkin-Elmer Co. Envision plate reader. Data are means of three experiments, each performed in duplicate. The raw basal value obtained in vehicle-treated wells was 9434±1303 counts/second. Curves were fit to the data using Graph-Pad Prism 4.0. The inset in the Figure shows the fit parameters.

Figure 4A:
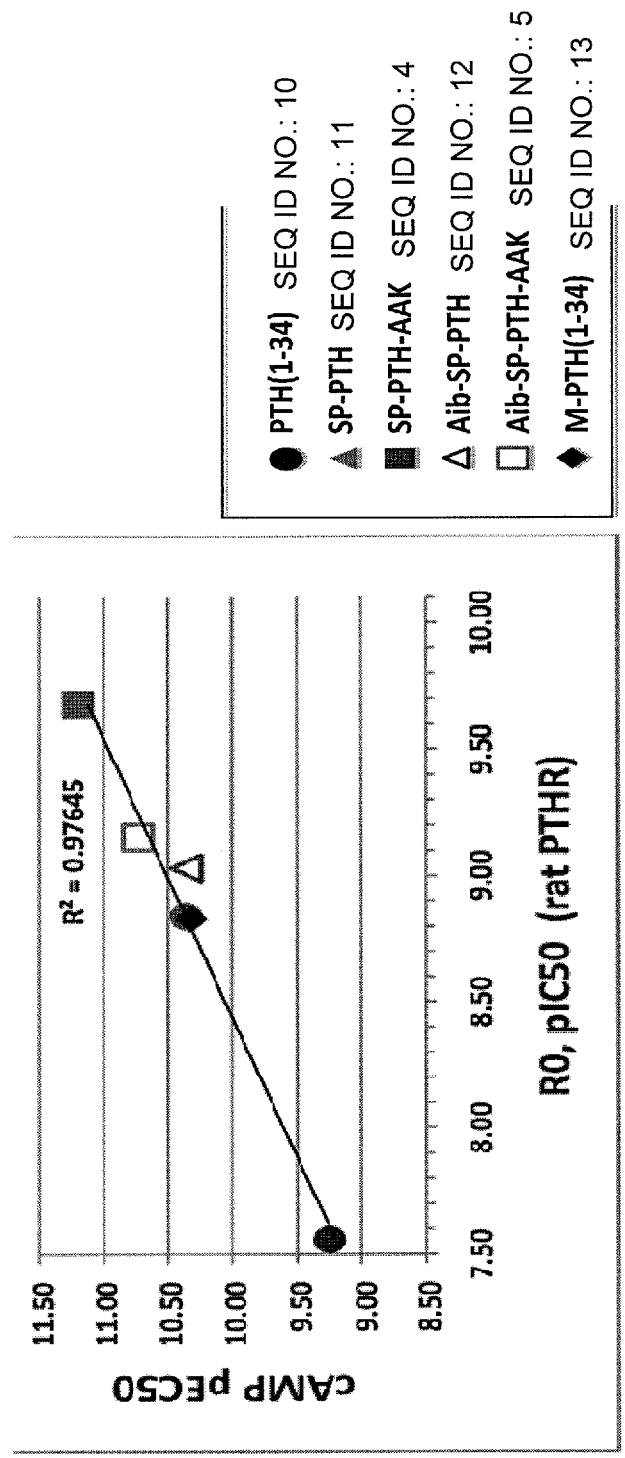
FIGS. 4A and 4B are graphs showing correlation between cAMP stimulation and either $R^0$ (FIG. 4A) or RG (FIG. 4B) binding.
Figure 4B:
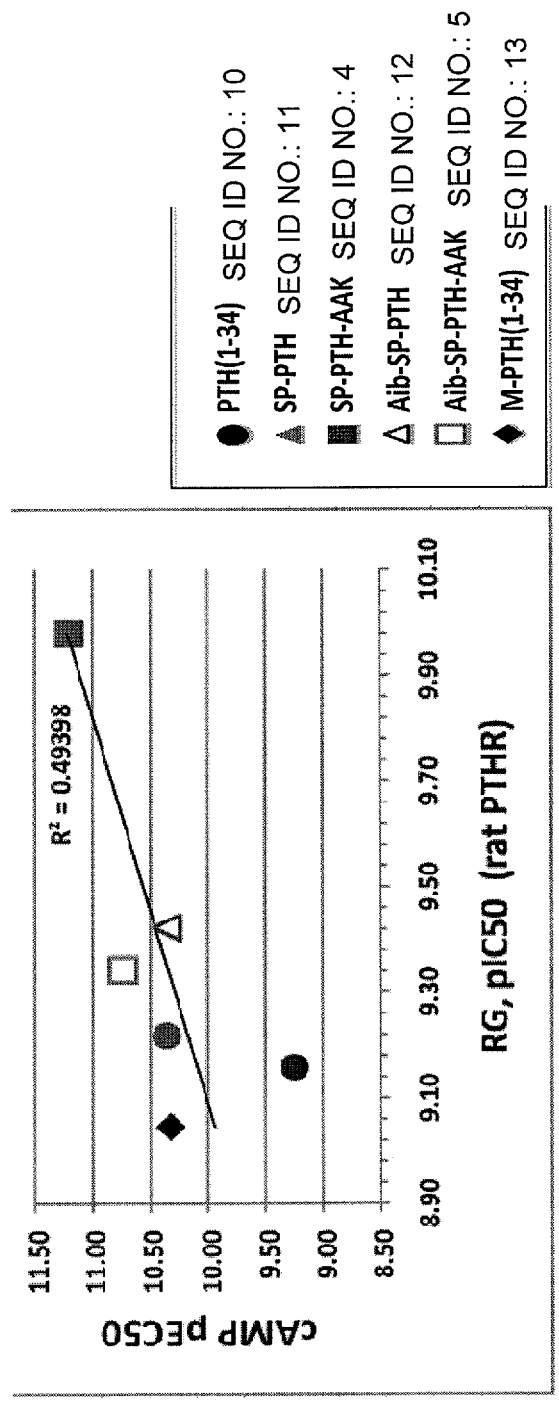

Correlation between cAMP potency and either R⁰ (FIG. 4A) or RG (FIG. 4B) binding was also calculated. A strong correlation between R⁰ binding and cAMP potency was observed. A lower correlation was observed between RG binding and cAMP potency.

Figure 5A:
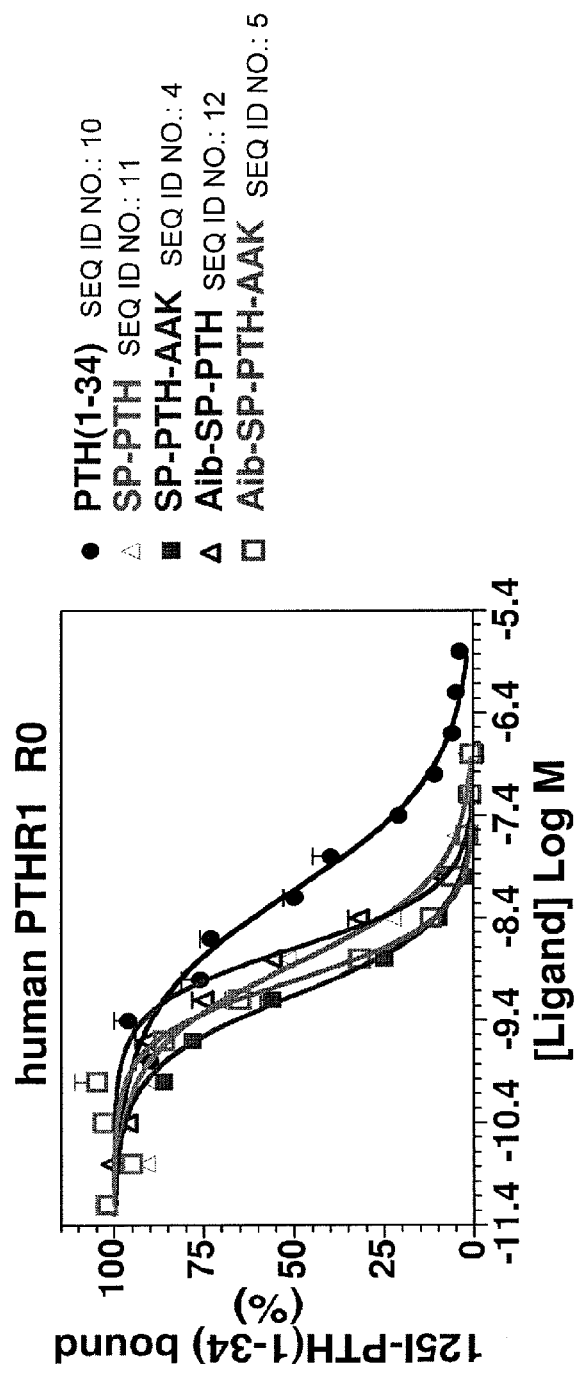
FIGS. 5A and 5B are graphs showing binding affinity of PTH(1-34) (SEQ ID NO:10), SP-PTH (SEQ ID NO:11), SP-PTH-AAK (SEQ ID NO:4), Aib-SP-PTH (SEQ ID NO:12), and Aib-SP-PTH-AAK (SEQ ID NO:5) to the $R^0$ (FIG. 5A) and RG (FIG. 5B) forms of the human PTH-1 receptor. Curve fit parameters are shown below each graph.
Figure 5B:
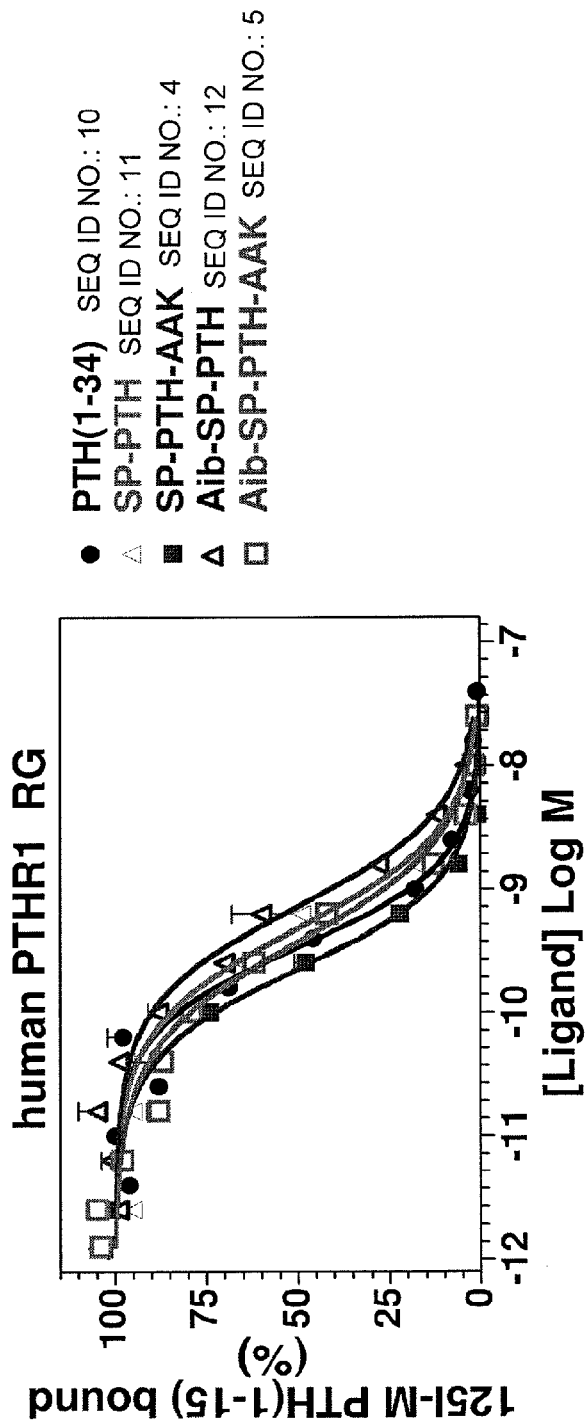
Figure 6:
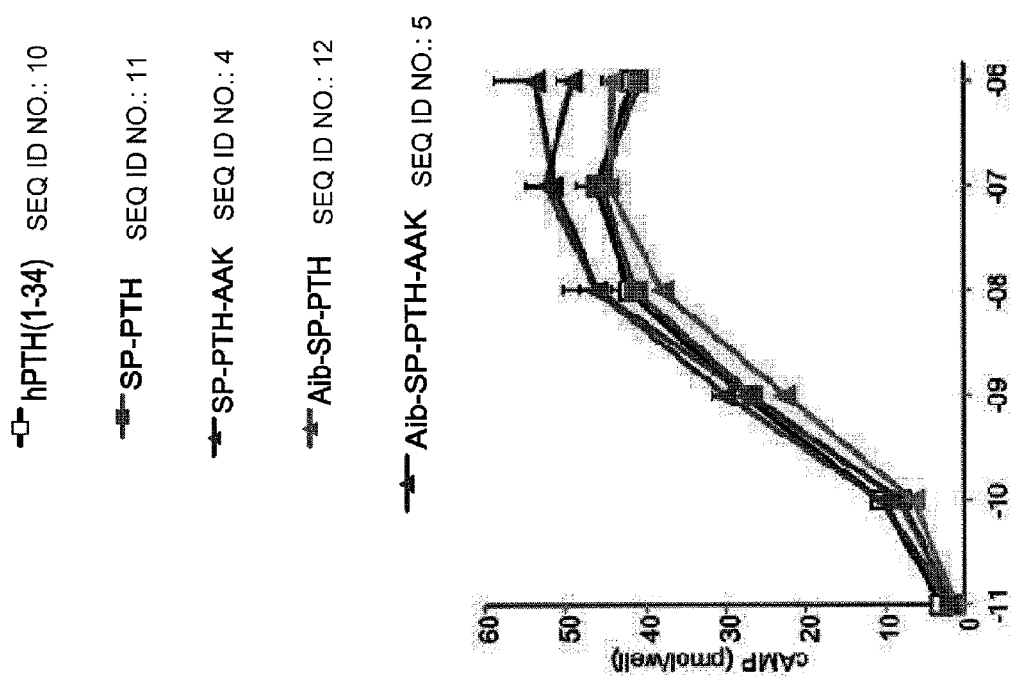
FIG. 6 is a graph showing cAMP stimulation of PTH(1-34) (SEQ ID NO:10), SP-PTH (SEQ ID NO:11), SP-PTH-AAK (SEQ ID NO:4), Aib-SP-PTH (SEQ ID NO:12), and Aib-SP-PTH-AAK (SEQ ID NO:5) at the human PTH-1 receptor as expressed on HKRK-B7 cells.

The R⁰ and RG binding experiments were repeated with the human PTH receptor (FIGS. 5A and 5B). Here, competition binding assays for the R⁰ and RG PTHR1 conformation were performed in membranes prepared from transfected COS-7 cells, as described by Dean et al., Mol Endocrinol 22:156-66, 2008. Data are means of three experiments, each performed in duplicate. Curves were fit to the data using Graph-Pad Prism 4.0. The inset shows the fit parameters. As with the rat receptors, the SP-PTH (SEQ ID NO:11), SP-PTH-AAK (SEQ ID NO:4), Aib-SP-PTH (SEQ ID NO:12), and Aib-SP-PTH-AAK (SEQ ID NO:5) polypeptides exhibited enhanced R⁰ binding as compared to PTH(1-34) (SEQ ID NO:10).

cAMP potency assays were also measured using the human receptor (FIG. 6). Here, HKRK-B7 cells, which are derived from LLC-PCK1 cells and are stably transfected with the human PTHR1, were incubated for 30 minutes in buffer containing either vehicle (−11 log M on plot abscissa), or varying concentrations (−10 to −6 log M) of the indicated ligand, and cAMP content in the cells was measured by RIA. SP-PTH-AAK (SEQ ID NO:4), Aib-SP-PTH-AAK (SEQ ID NO:5), SP-PTH (SEQ ID NO:11), and Aib-SP-PTH (SEQ ID NO:12) exhibited cAMP potencies similar to PTH(1-34) (SEQ ID NO:10). A summary of the data is provided in Table 2.

TABLE 2

Summary of receptor binding and cAMP activation data

| | Binding | | | | | | cAMP MC3T3-E1 cells | | |
|---|---|---|---|---|---|---|---|---|---|
| | human PTHR1 $IC_{50}$ (Log M) nM | | | rat PTHR1 $IC_{50}$ (Log M) nM | | | $EC_{50}$ (Log M) pM | $E_{max}$ (pmole/well) | |
| peptide | R0 | RG | n | R0 | RG | n | | | n |
| PTH(1-34) | −8.17 ± 0.12 / 6.7 | −9.48 ± 0.05 / 0.33 | 3 | −7.56 ± 0.11 / 28 | −9.16 ± 0.06 / 0.70 | 4 | −9.2 ± 0.3 / 563 | 70.1 ± 12.2 | 6 |
| SP-PTH | −8.86 ± 0.06 / 1.4 | −9.32 ± 0.11 / 0.48 | 3 | −8.84 ± 0.05 / 1.4 | −9.22 ± 0.12 / 0.61 | 4 | −10.4 ± 0.1 / 44 | 60.6 ± 12.4 | 6 |
| SP-PTH-AAK | −9.17 ± 0.04 / 0.68 | −9.65 ± 0.06 / 0.22 | 3 | −9.68 ± 0.09 / 0.21 | −9.98 ± 0.11 / 0.70 | 4 | −11.2 ± 0.2 / 6.3 | 62.3 ± 13.6 | 6 |
| AIB-SP-PTH | −8.74 ± 0.03 / 1.8 | −9.16 ± 0.12 / 0.69 | 3 | −9.03 ± 0.04 / 0.93 | −9.42 ± 0.11 / 0.38 | 4 | −10.4 ± 0.1 / 44 | 62.1 ± 13.3 | 6 |
| AIB-SP-PTH-AAK | −9.03 ± 0.04 / 0.94 | −9.43 ± 0.04 / 0.37 | 3 | −9.15 ± 0.03 / 0.70 | −9.34 ± 0.20 / 0.45 | 4 | −10.7 ± 0.1 / 18 | 57.9 ± 13.9 | 6 |
| M-PTH(1-34) | −9.02 ± 0.09 / 0.95 | −9.34 ± 0.04 / 0.45 | 3 | −8.83 ± 0.04 / 1.5 | −9.05 ± 0.15 / 0.90 | 4 | −10.3 ± 0.1 / 48 | 56.3 ± 13.4 | 6 |
| PTHrP(1-36) | −8.04 ± 0.02 / 9.1 | −9.84 ± 0.03 / 0.14 | 3 | n.t. | | | n.t. | | |

Peptide SEQ ID NOs from top to bottom: SEQ ID NO:10, 11, 4, 12, 5, 13, and 14.

Example 3 cAMP Response Following Ligand Wash-Out

The ability of SP-PTH-AAK (SEQ ID NO:4), Aib-PTH-AAK (SEQ ID NO:5), SP-PTH (SEQ ID NO:11), and Aib-SP-PTH (SEQ ID NO:12) to stimulate cAMP activity following washing out of the ligand was also tested. cAMP wash-out response assays were performed in MC3T3-E1 cells in 96-well plates as described by Okazaki et al., Proc Natl Acad Sci USA 105:16525-30, 2008. Cells were treated at room temperature with vehicle or the indicated ligand (100 nM) for five minutes; for each ligand duplicate wells were used to obtain the initial (maximum cAMP values); in these wells, cells were co-incubated with ligand and IBMX. After five minutes of initial treatment, the buffer was removed, and, for the initial wells, the reactions were terminated by addition of 50 mM HCl. In the other wells, the cells were rinsed three times with buffer, and incubated in buffer for varying times, as indicated on the abscissa; after which the buffer was replaced by a buffer containing IBMX, and the cells were incubated for another five minutes. After that, the buffer was removed and the reactions were terminated by addition of 50 mM HCl. The cAMP contents of the HCl lysates were then determined by RIA.

Figure 7A:
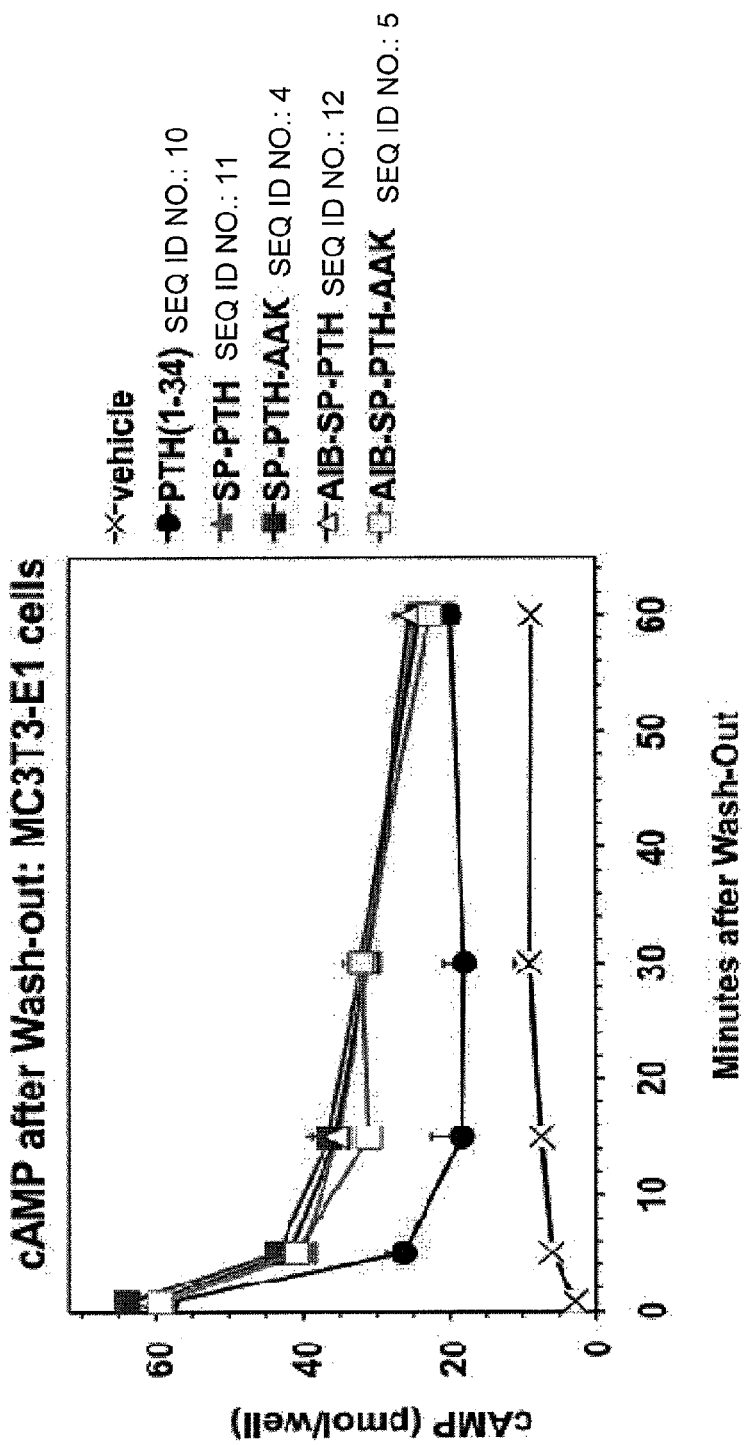
FIGS. 7A and 7B are graphs showing cAMP stimulation following ligand washout.
Figure 7B:
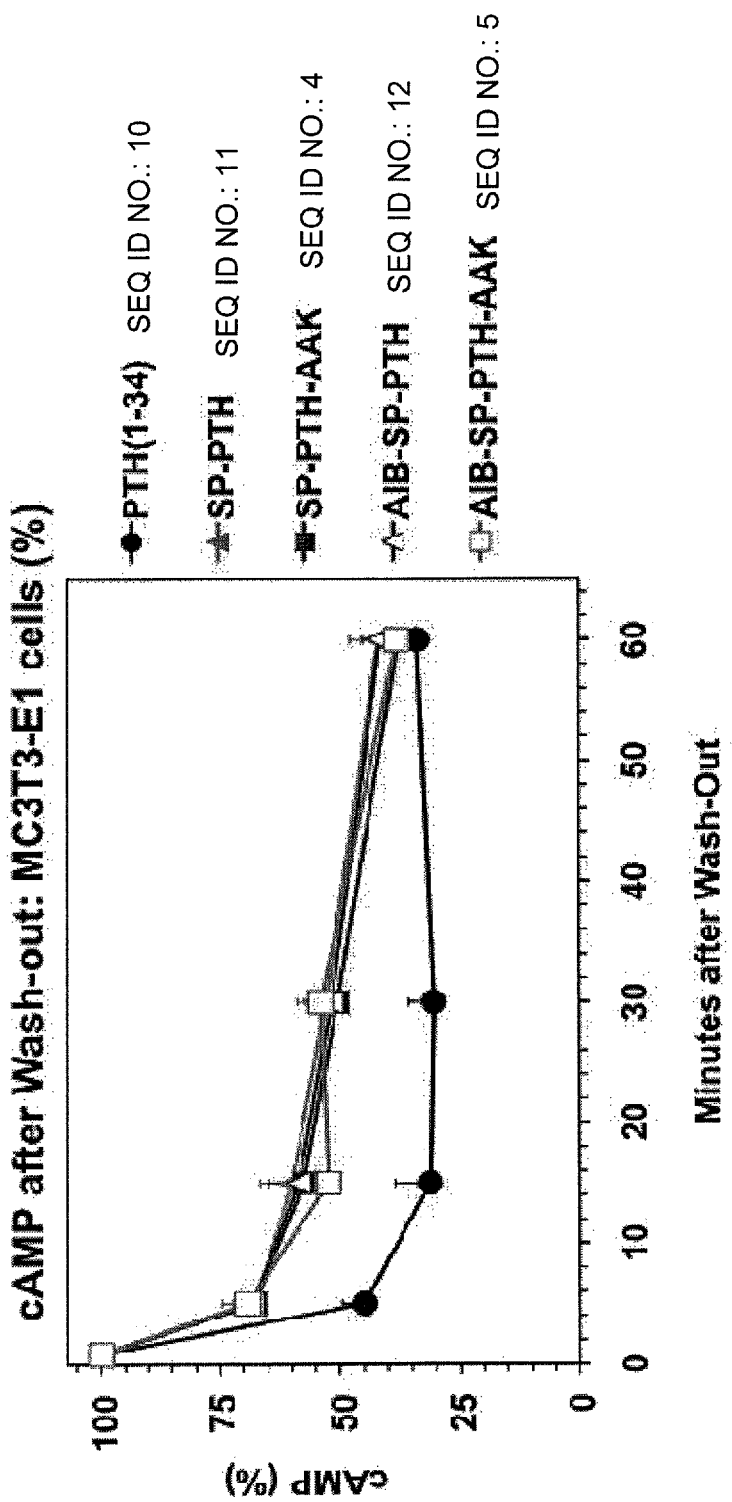

As shown in FIGS. 7A and 7B, the SP-PTH (SEQ ID NO:11), SP-PTH-AAK (SEQ ID NO:4), Aib-SP-PTH (SEQ ID NO:12), and Aib-SP-PTH-AAK (SEQ ID NO:5) maintained cAMP-stimulating activity for longer periods of time than PTH(1-34) (SEQ ID NO:10), thus indicating that these polypeptides have long-acting agonist activity.

Example 4

Studies in Mice

Figure 8A:
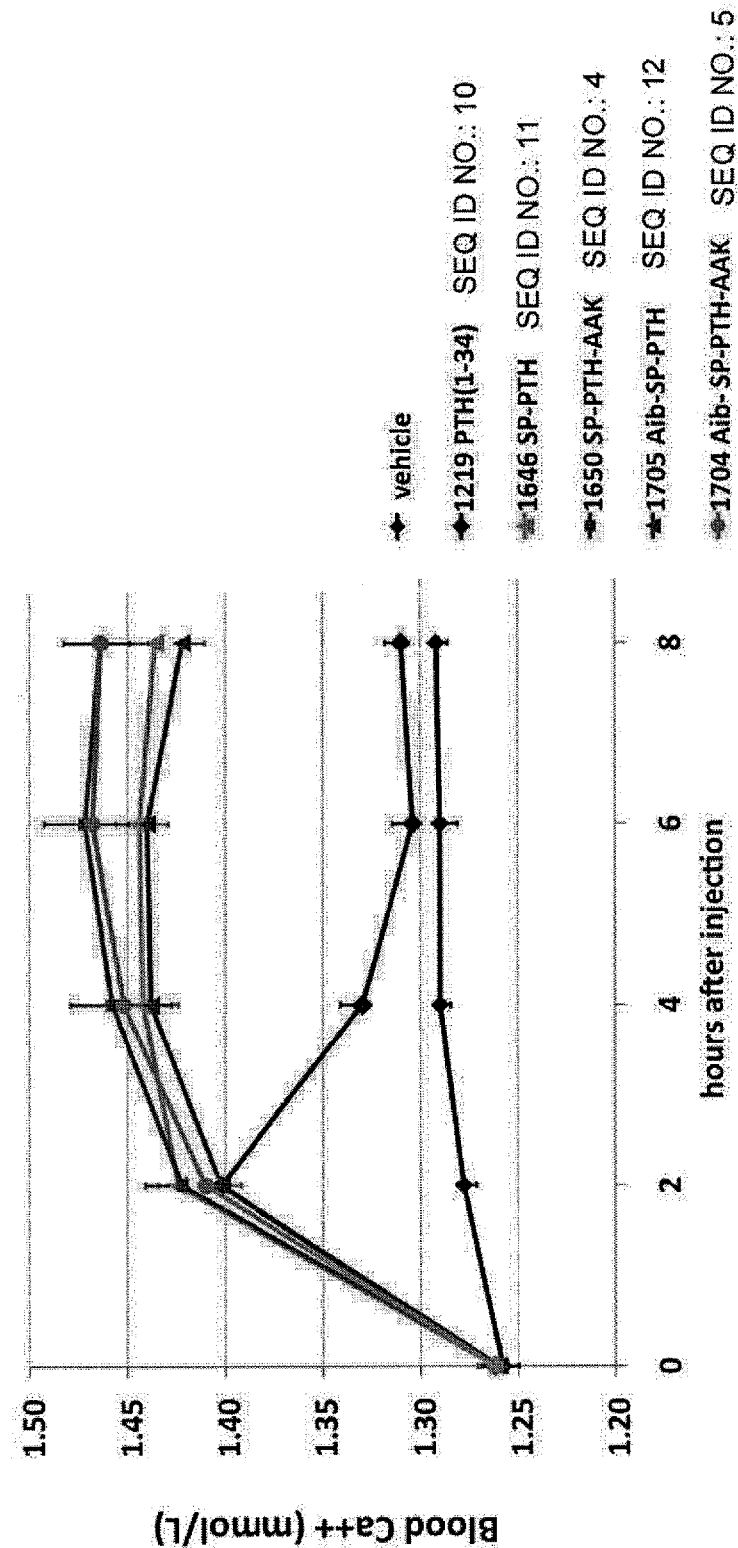
FIGS. 8A-8E are graphs showing blood calcium levels in mice receiving subcutaneous injections of vehicle, or at 5 nmol/kg PTH(1-34) (SEQ ID NO:10), SP-PTH (SEQ ID NO:11), SP-PTH-AAK (SEQ ID NO:4), Aib-SP-PTH (SEQ ID NO:12), or Aib-SP-PTH-AAK (SEQ ID NO:5) for 0-8 hours (FIG. 8A) or 0-30 hours (FIG. 8B). Similar results are shown for the peptides at 10 nmol/kg injected subcutaneously in FIG. 8C (0-24 hours) and FIG. 8D (0-54 hours). Results from a similar experiment under fasting conditions are also shown (FIG. 8E).
Figure 8B:
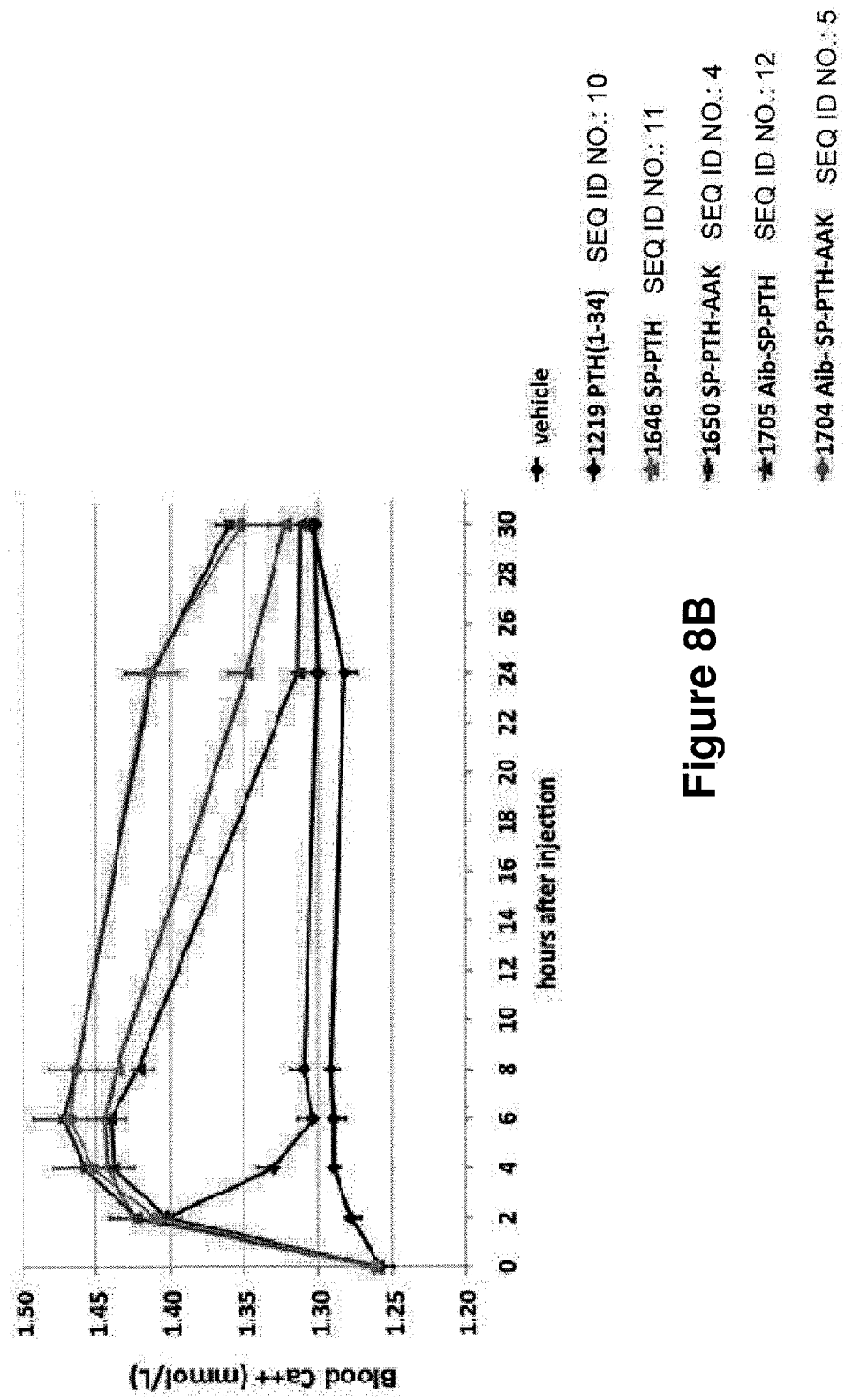
Figure 8C:
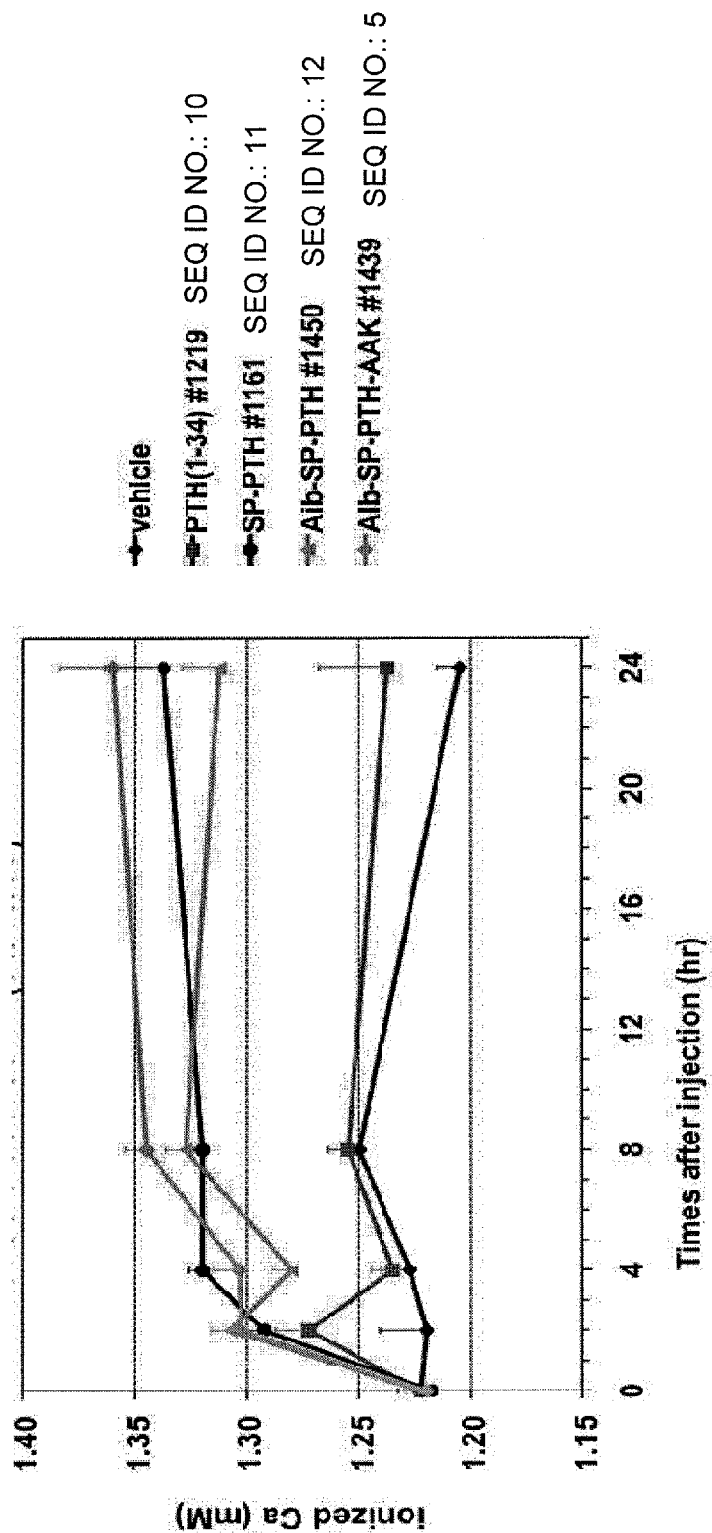
Figure 8D:
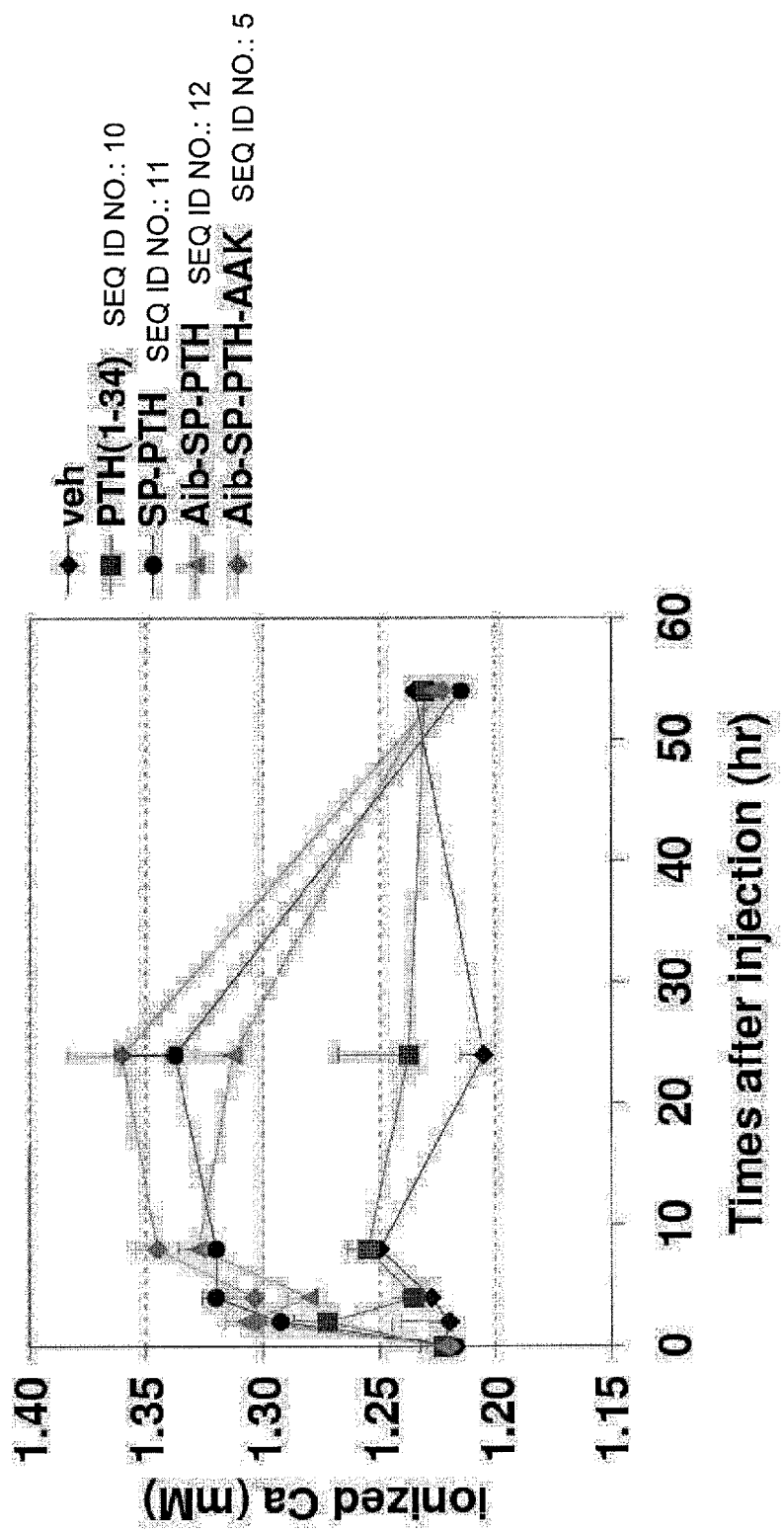
Figure 8E:
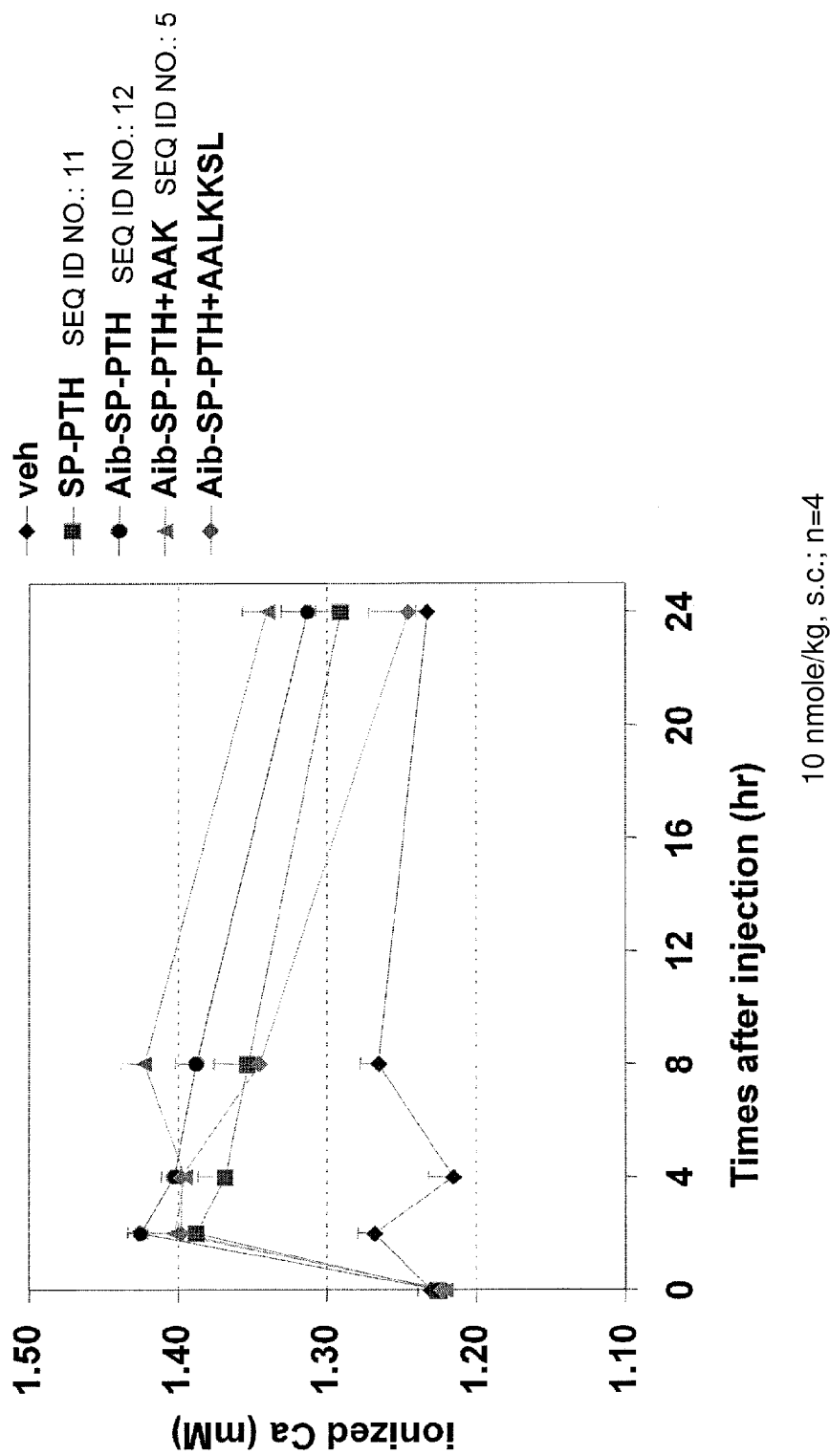

Blood $Ca^{++}$ responses in mice were also assayed. Mice (C57 BL/6) were injected subcutaneously with either vehicle or the indicated ligand to give a final dose of 5 nmol/kg body weight, and blood was withdrawn via the tail at times after injection and assessed for $Ca^{++}$ concentration using a Bayer Rapid Lab model 348 blood analyzer. As shown, all polypeptides, including PTH(1-34) exhibited similar calcium levels two hours following administration (FIG. 8A). At later time points (4, 6, 8, and 24 hours), however, blood calcium levels were increased in mice receiving SP-PTH (SEQ ID NO:11), SP-PTH-AAK (SEQ ID NO:4), Aib-SP-PTH (SEQ ID NO:12), or Aib-SP-PTH-AAK (SEQ ID NO:5) as compared to mice receiving either PTH(1-34) or a vehicle (FIGS. 8A and 8B). A similar experiment using 10 nmol/kg by intravenous injection was also conducted with similar results (FIGS. 8C and 8D). A similar experiment conducted under fasting conditions was also performed, as shown in FIG. 8E).

Example 5

Studies in Rats

The effects of polypeptides on rats having undergone thyroparathyroidectomy (TPTX) was also tested. Here, five-week-old male Crl:CD(SD) rats were obtained from Charles River Laboratories Japan, Inc. (Kanagawa, Japan) and acclimated for 1 week under standard laboratory conditions at 20-26° C. and 35-75% humidity. The rats were fed free access to tap water and standard rodent chow (CE-2) containing 1.1% calcium, 1.0% phosphate, and 250 IU/100 g of vitamin $D_3$ (Clea Japan, Inc., Shizuoka, Japan).

Thyroparathyroidectomy (TPTX) was performed on six-week-old rats. TPTX rats were selected (<1.0 mM) by serum ionized calcium (iCa) from tail vein bleeding at 24 hours after the operation. TPTX rats were divided into six groups of five or six animals by iCa at 72 hours after the operation. TPTX-vehicle group intravenously received the vehicle (10 mM acetic acid solution) at a dose of 1 ml/kg body weight from tail vein. SP-PTH (SEQ ID NO:11), SP-PTH-AAK (SEQ ID NO:4), Aib-SP-PTH (SEQ ID NO:12), and Aib- SP-PTH-AAK (SEQ ID NO:5) were each intravenously injected into the TPTX rats at doses of 1.25 nmol/kg.

Figure 9:
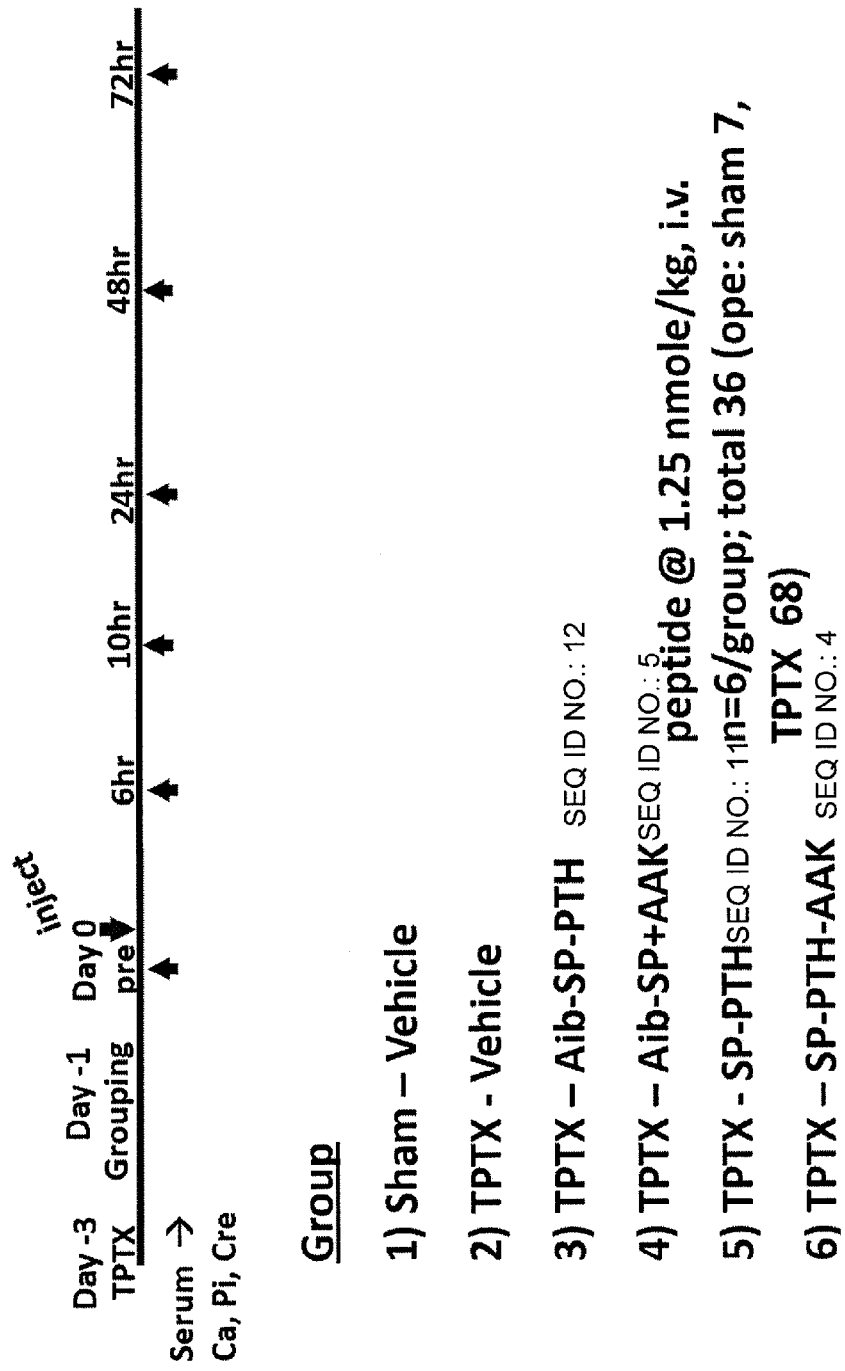
FIG. 9 is a schematic diagram showing the experimental protocol used in measuring blood calcium, serum phosphate levels, and calcium-to-creatinine ratio in urine from TPTX rats.

To measure serum calcium and phosphate, rats were anesthetized using Ketamine, and blood was obtained from neck vein at various times (e.g., at 6, 8, 24, 48, and 72 hours) after each injection (FIG. 9). Serum calcium and phosphorus were determined by an autoanalyzer (736-20 Model Hitachi, Tokyo, Japan).

Figure 10A:
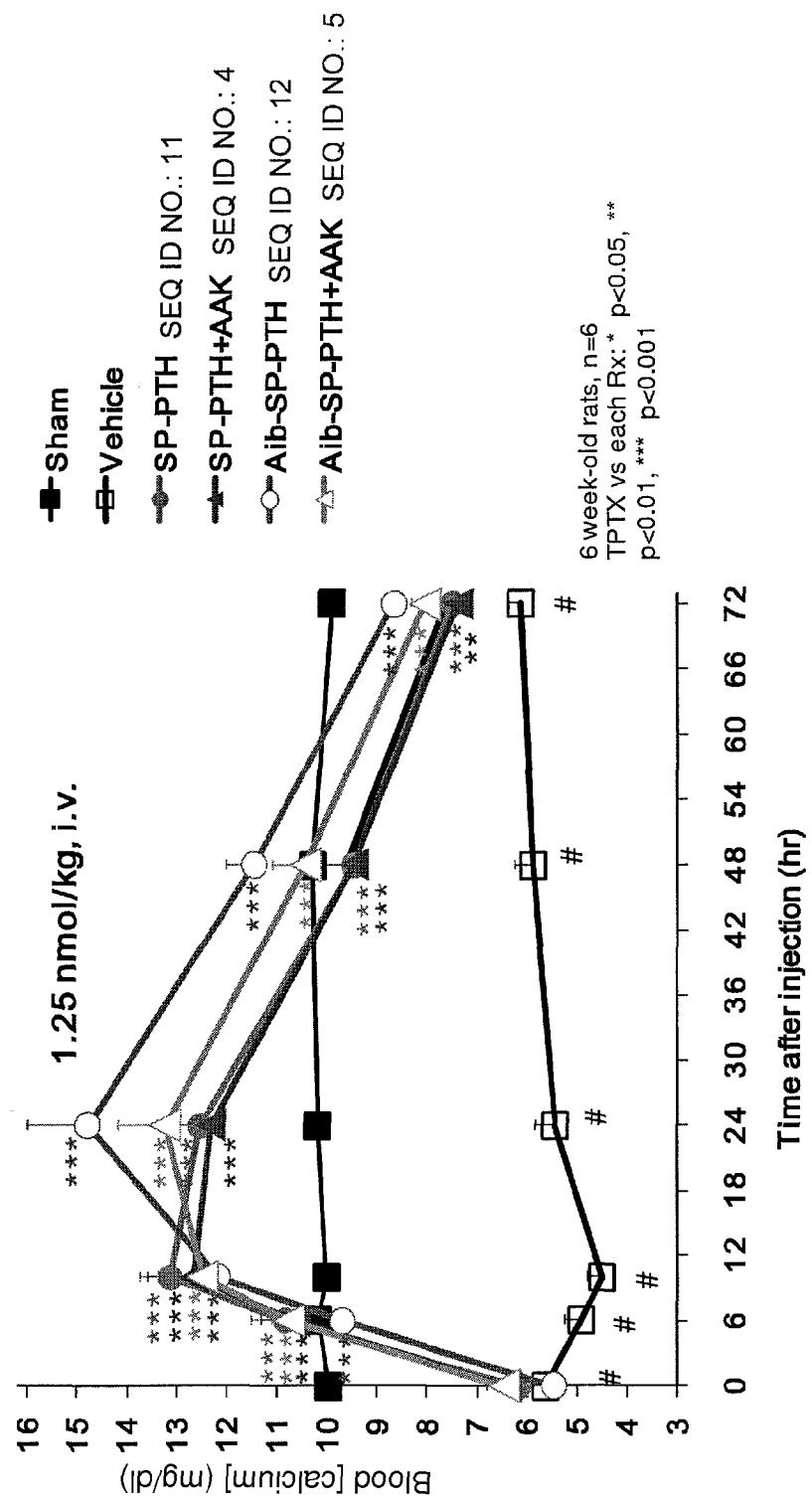
FIGS. 10A-10E are graphs showing blood calcium (FIG. 10A) and serum inorganic phosphate (FIG. 10B) responses in TPTX rats administered a vehicle, SP-PTH (SEQ ID NO:11), SP-PTH-AAK (SEQ ID NO:4), Aib-SP-PTH (SEQ ID NO:12), or Aib-SP-PTH-AAK (SEQ ID NO:5). Sham operated rats are shown as a control. A similar experiment comparing SP-PTH at 1.25 and 5 nmol/kg to PTH(1-34) (SEQ ID NO:10) at 1.25, 5, and 20 nmol/kg is also provided (FIG. 10C). Pharmacokinetic profiles in normal rats injected intravenously with 10 nmol/kg PTH(1-34) (SEQ ID NO:10) or SP-PTH (SEQ ID NO:11) are also shown (FIG. 10D). Pharmacokinetic profiles in TPTX rats injected intravenously with 24.3 nmol/kg hPTH(1-34) (SEQ ID NO:10), hPTH(1-84), or SP-PTH-AAK (SEQ ID NO:4) are also shown (FIG. 10E).
Figure 10B:
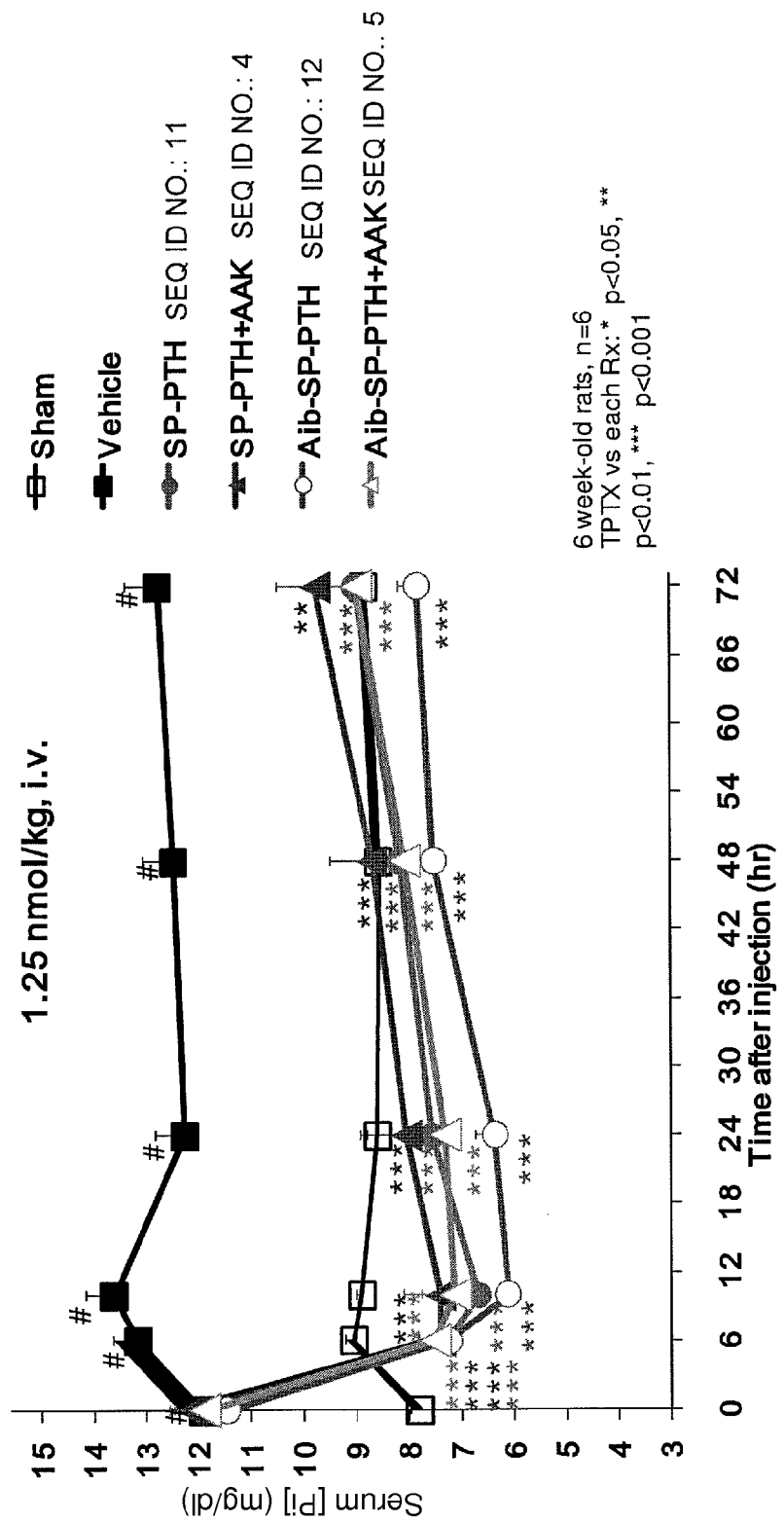
Figure 10C:
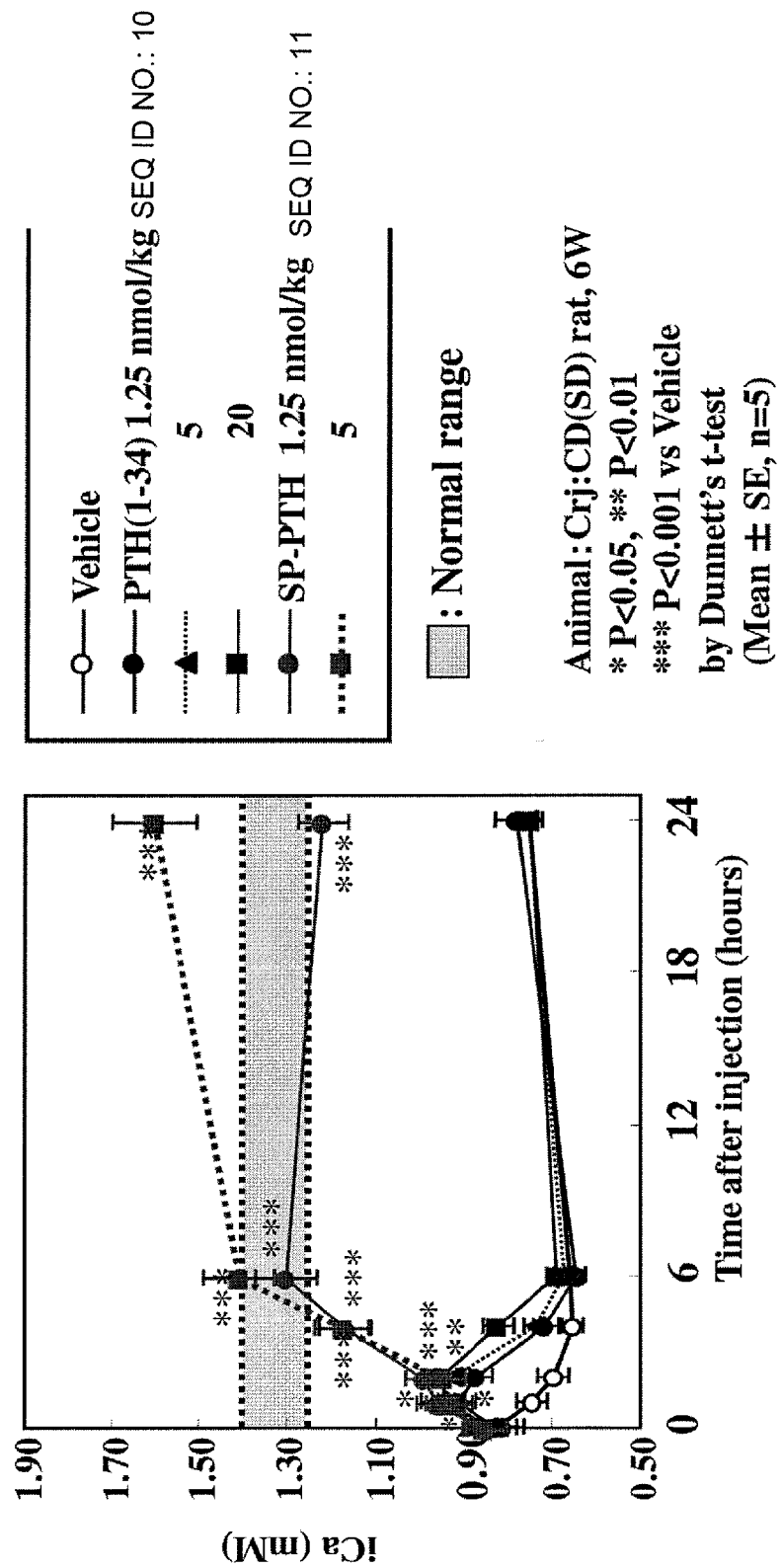
Figure 10D:
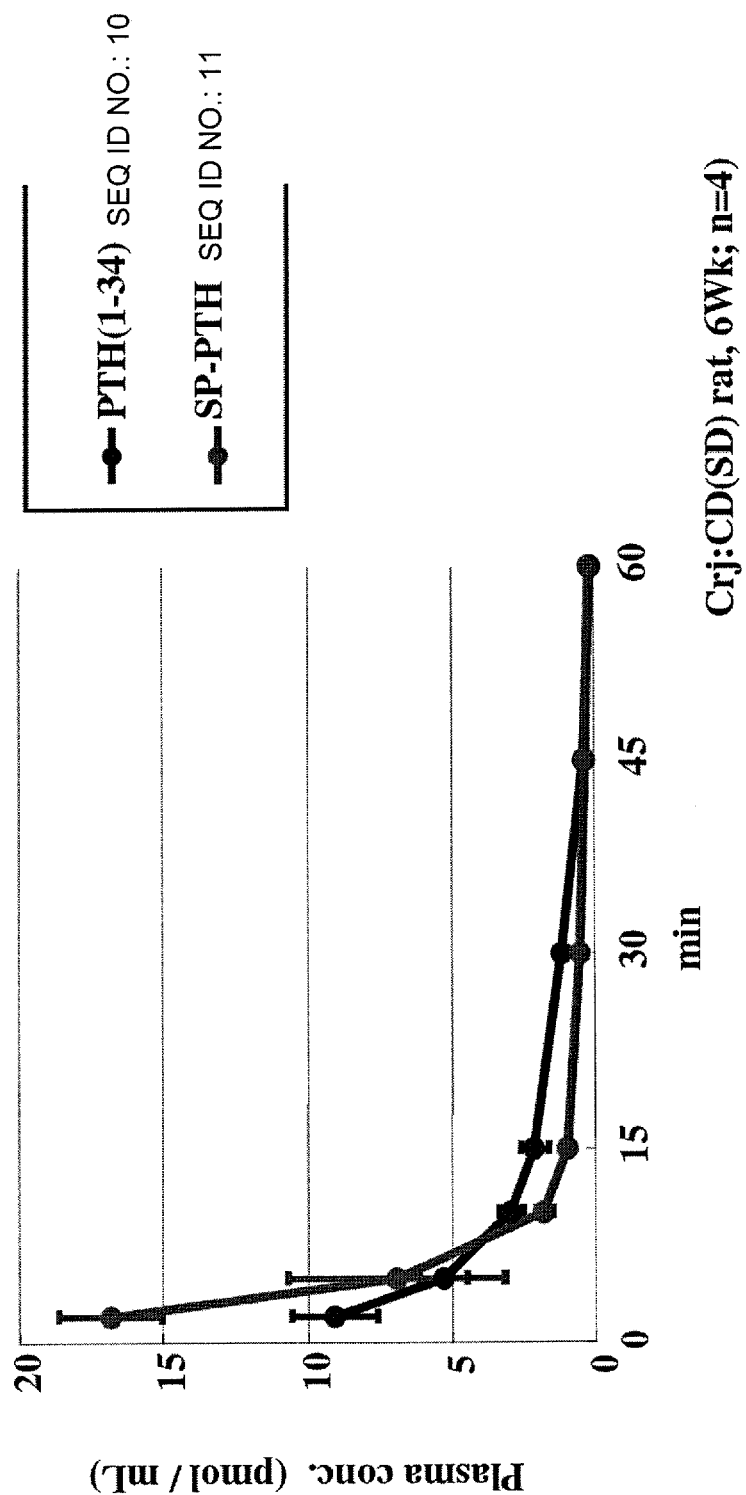
Figure 10E:
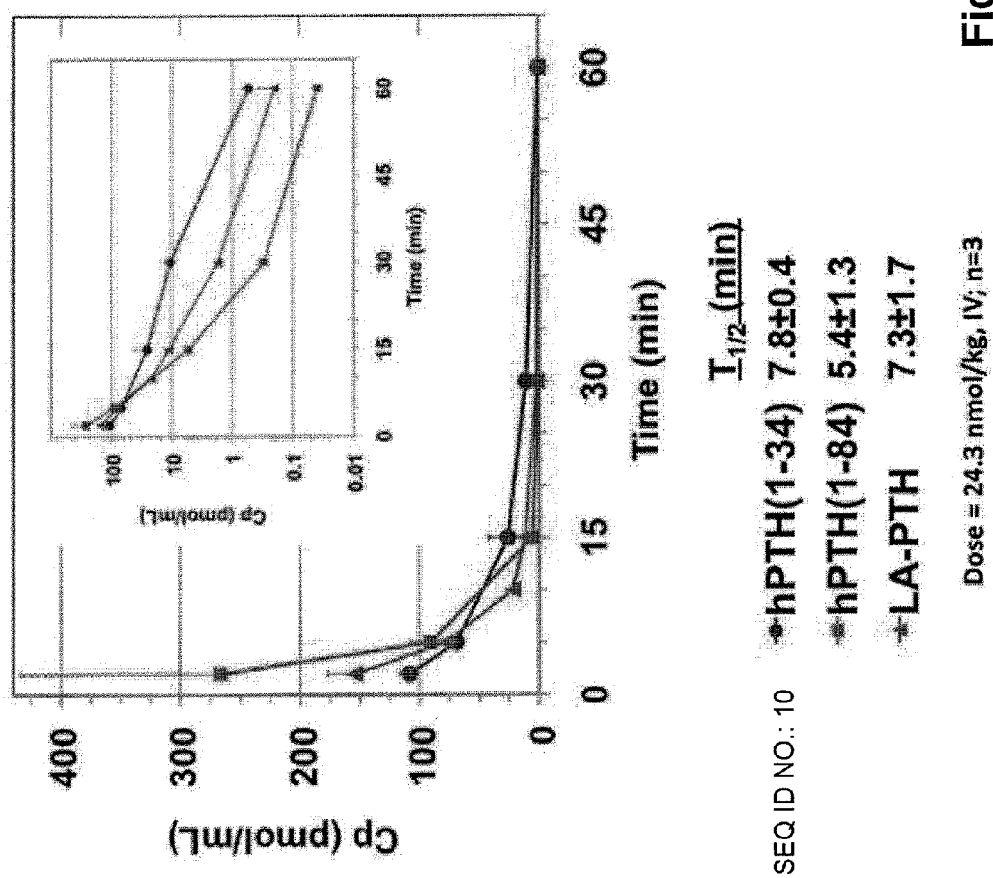
Figure 12A:
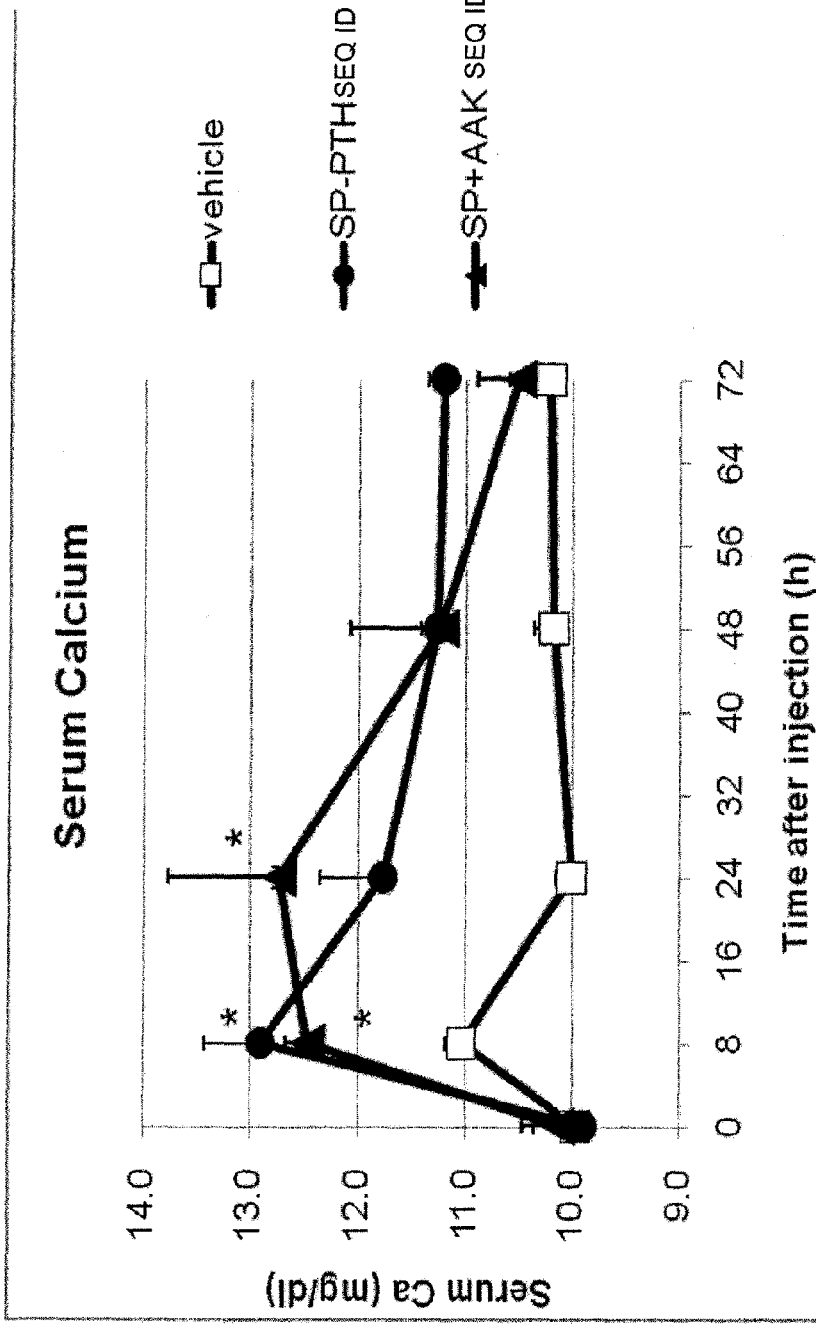
FIGS. 12A-12C are graphs showing serum calcium (FIGS. 12A and 12C) and serum phosphate (FIG. 12B) in cynomolgus monkeys receiving an injection of vehicle, SP-PTH (SEQ ID NO:11), SP-PTH-AAK (SEQ ID NO:4), or PTH(1-34) (SEQ ID NO:10) (* $P<0.05$, vs. vehicle; ** $P<0.01$ vs. vehicle).
Figure 12B:
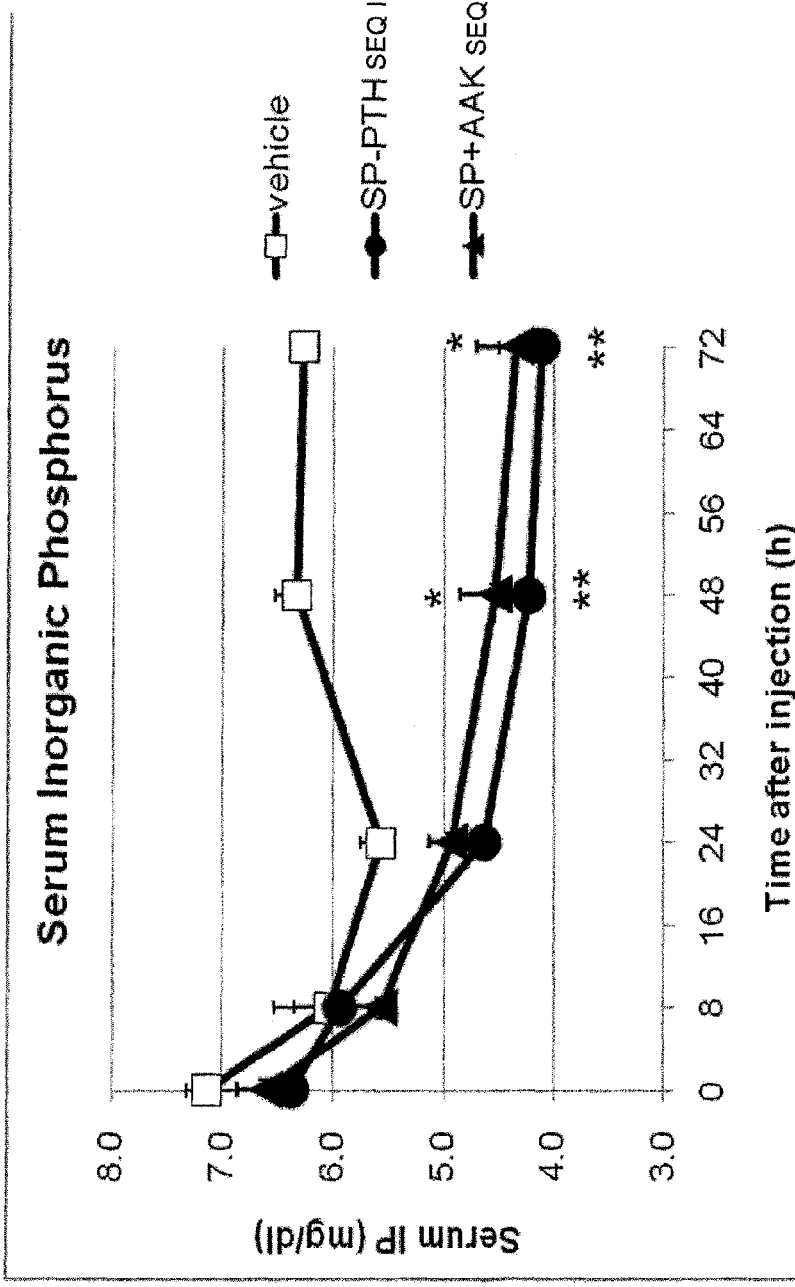
Figure 13A:
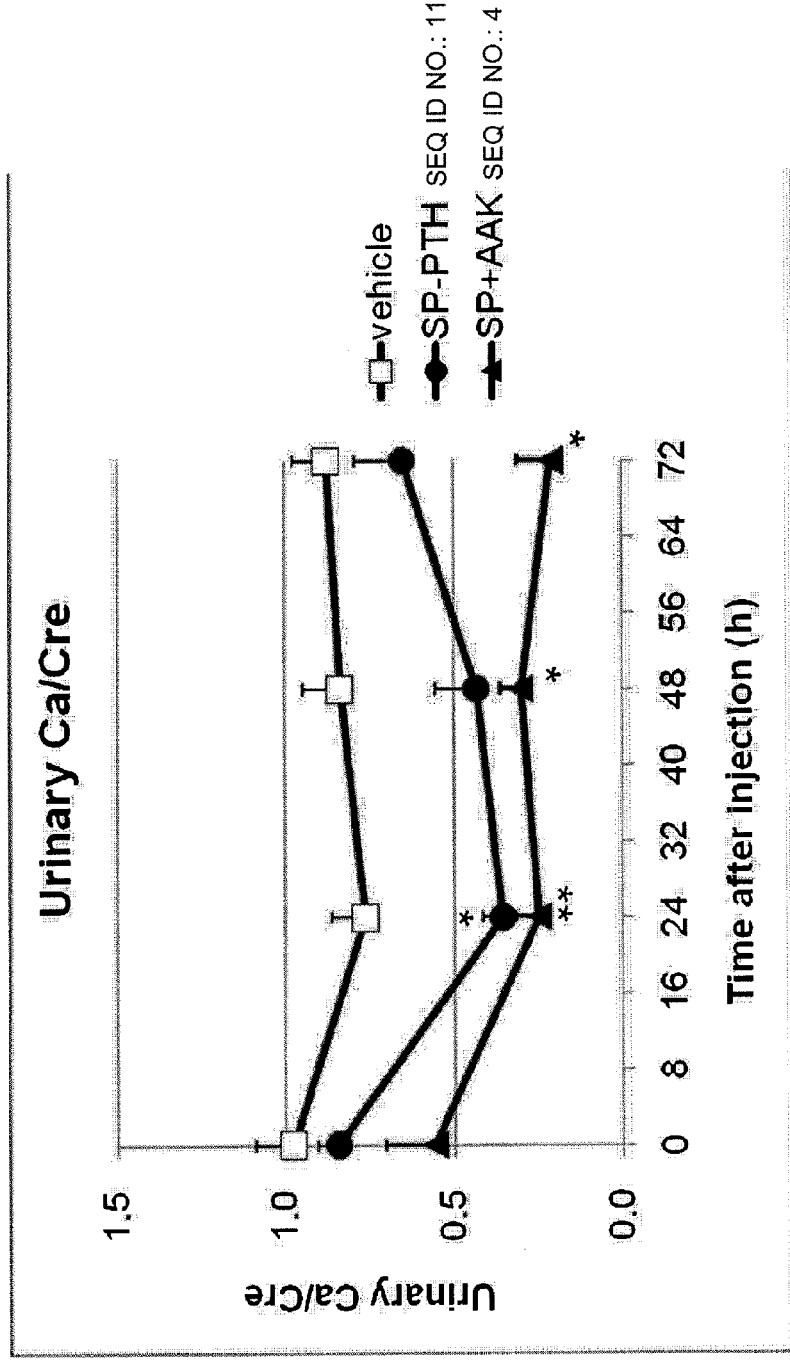
FIGS. 13A and 13B are graphs showing urinary calcium (FIG. 13A) and urinary phosphate (FIG. 13B) creatinine ratios in cynomolgus monkeys receiving an intravenous injection of vehicle, SP-PTH (SEQ ID NO:11), or SP-PTH-AAK (SEQ ID NO:4) (* P<0.05, vs. vehicle; ** P<0.01 vs. vehicle).
Figure 13B:
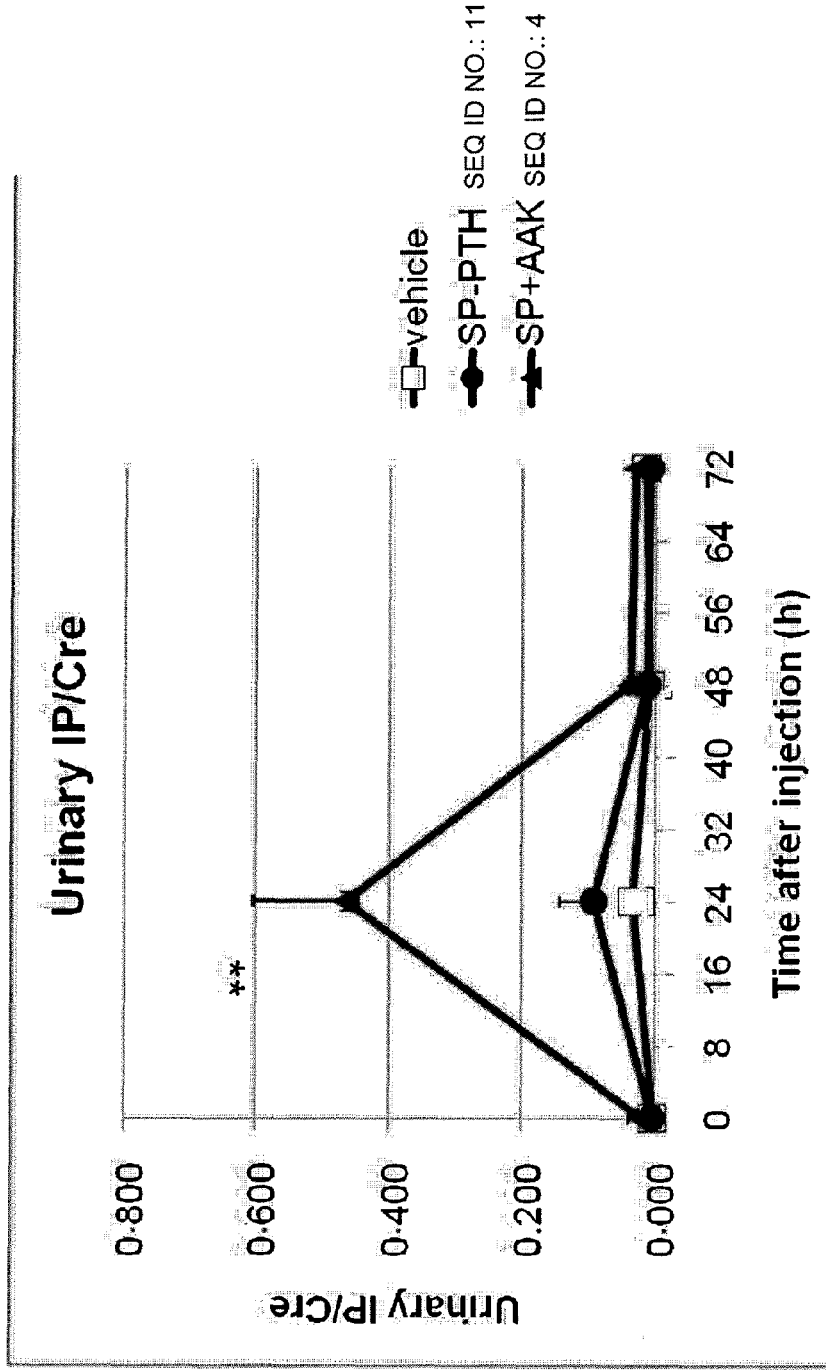

As shown in FIGS. 10A and 10B, serum calcium levels were increased for a prolonged period upon i.v. administration of the polypeptides and serum phosphate levels were reduced. For comparison, a similar experiment comparing SP-PTH at 1.25 and 5 nmol/kg to PTH(1-34) (SEQ ID NO:10) at 1.25, 5, and 20 nmol/kg is also provided (FIG. 10C). These differences did not appear to be mediated by changes in pharmacokinetcs, as PTH(1-34) (SEQ ID NO:10) and SP-PTH (SEQ ID NO:11) exhibited similar profiles in normal rats (FIG. 10D) and in TPTX rats (FIG. 10E). The properties of these peptides in TPTX rats are shown in Table 3.

subcutaneously at a 40-fold higher dose than the experiments of FIGS. 12A and 12B. Urinary calcium/creatinine ratio was decreased in mice receiving either of polypeptide as compared to a vehicle (FIG. 13A). Urinary phosphate/creatinine ratio was also measured, as shown in FIG. 13B.

Figure 14:
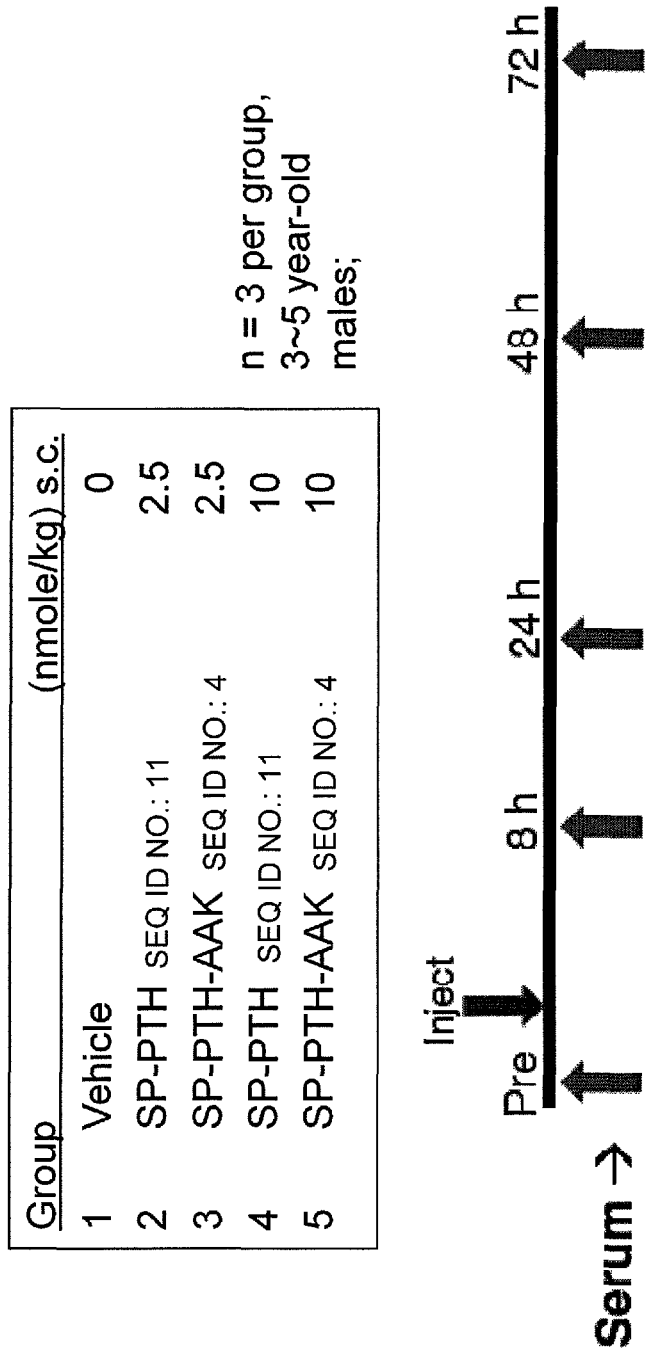
FIG. 14 is a schematic diagram showing the experimental protocol used in measuring serum calcium and serum phosphate levels in cynomolgus monkeys receiving vehicle or either 2.5 nmol/kg or 10 nmol/kg of SP-PTH (SEQ ID NO:11) or SP-PTH-AAK (SEQ ID NO:4).
Figure 15A:
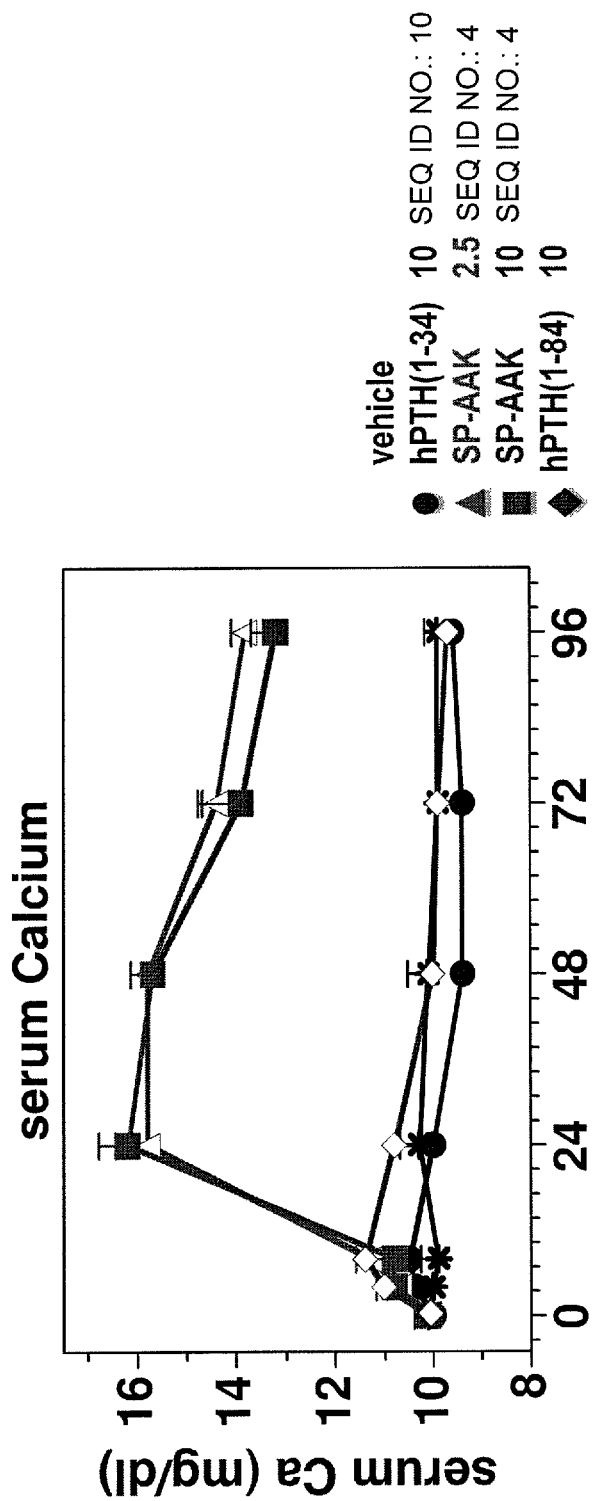
FIGS. 15A-15H are graphs showing serum and urine calcium and phosphate levels and serum creatinine levels in cynomolgus monkeys receiving vehicle, 2.5 nmol/kg or 10 nmol/kg of SP-PTH-AAK (SEQ ID NO:4), 10 nmol/kg of PTH(1-34) (SEQ ID NO:10), or 10 nmol/kg of PTH(1-84).
Figure 15B:
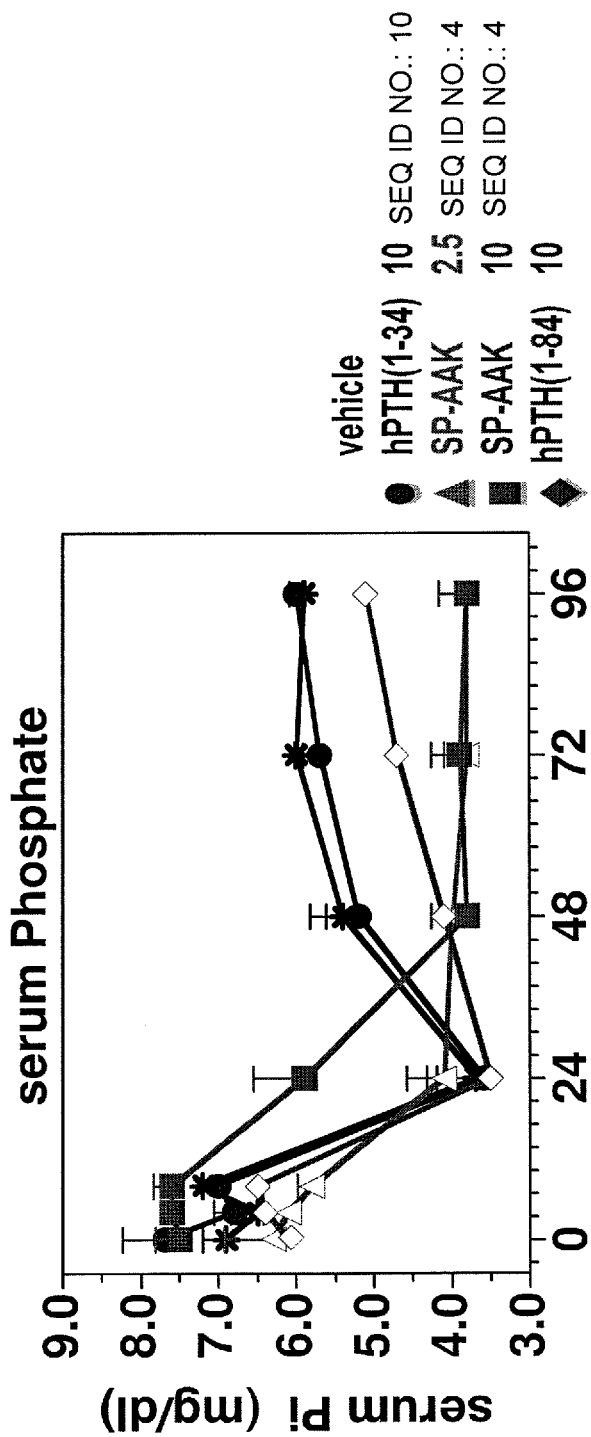
Figure 15C:
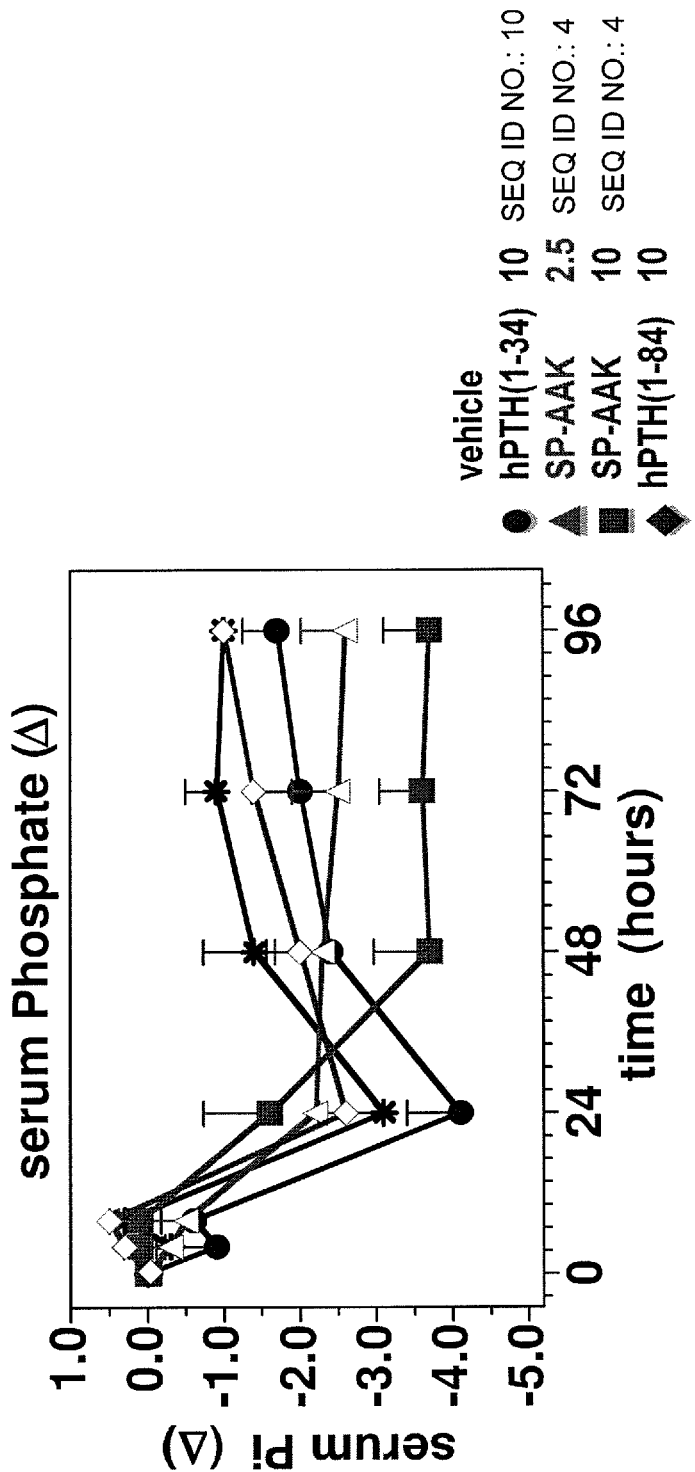
Figure 15D:
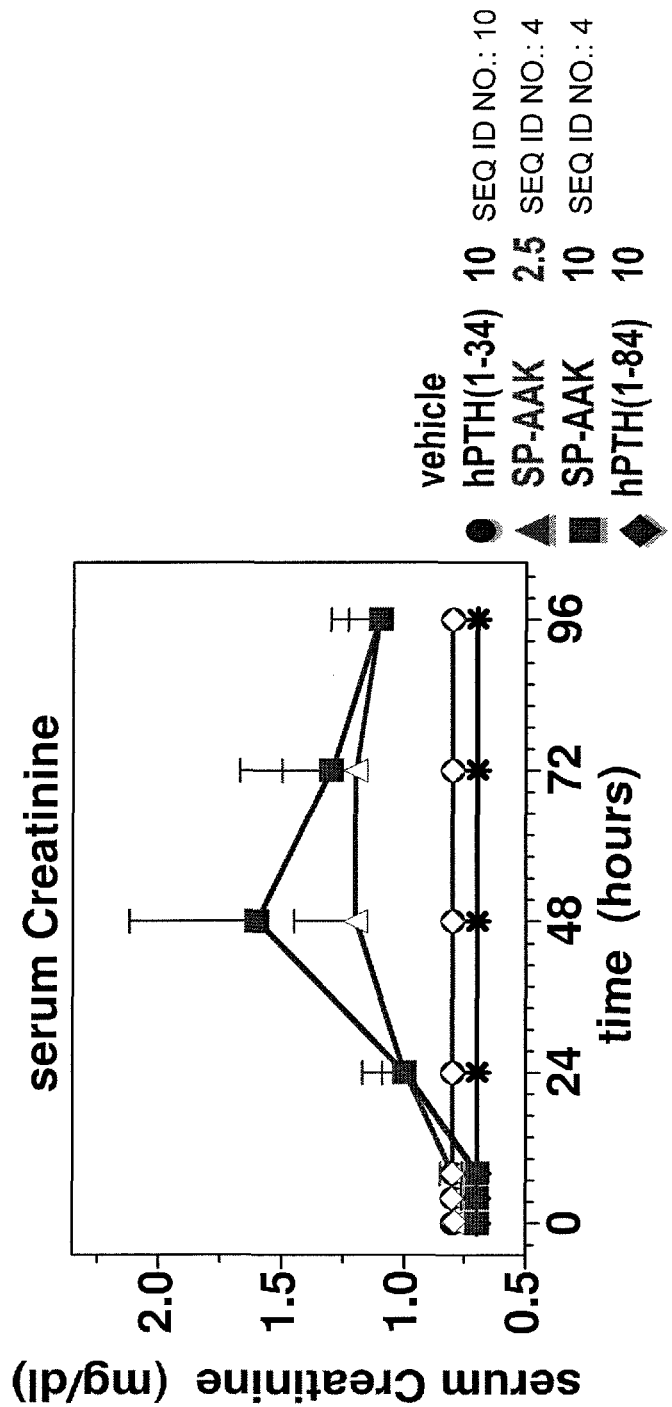
Figure 15E:
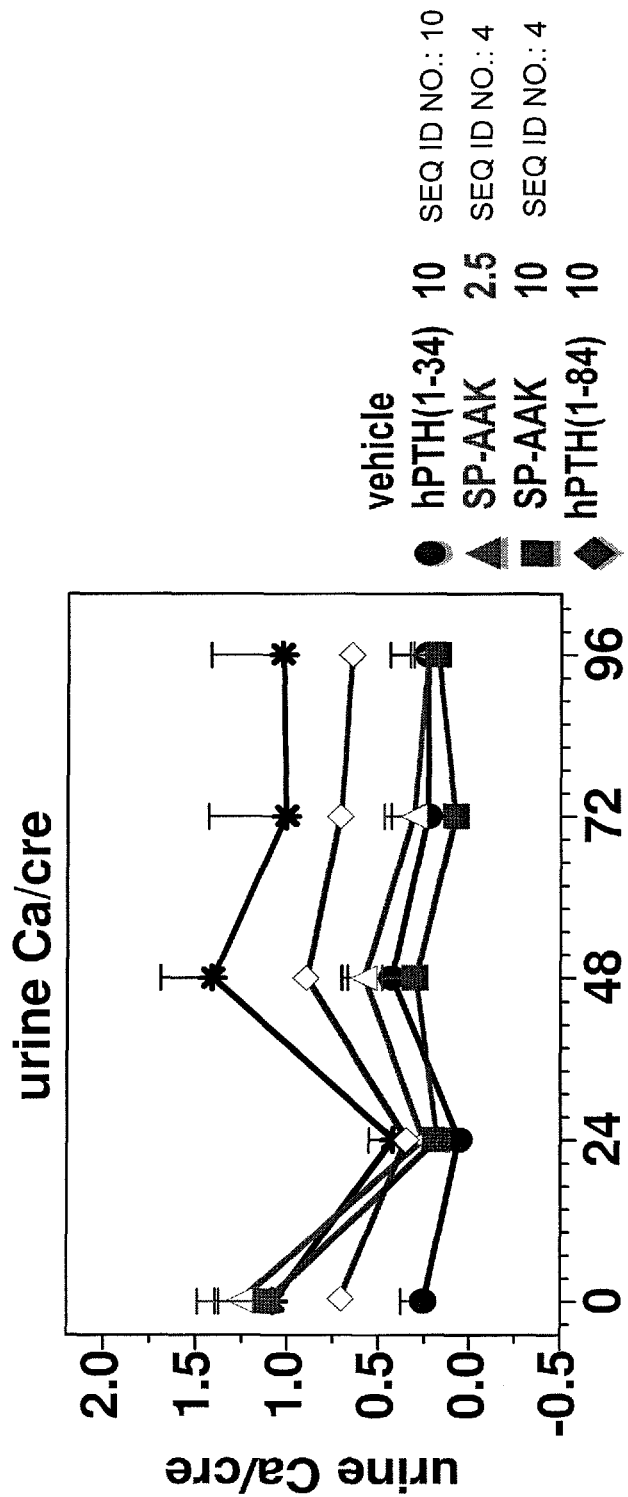
Figure 15F:
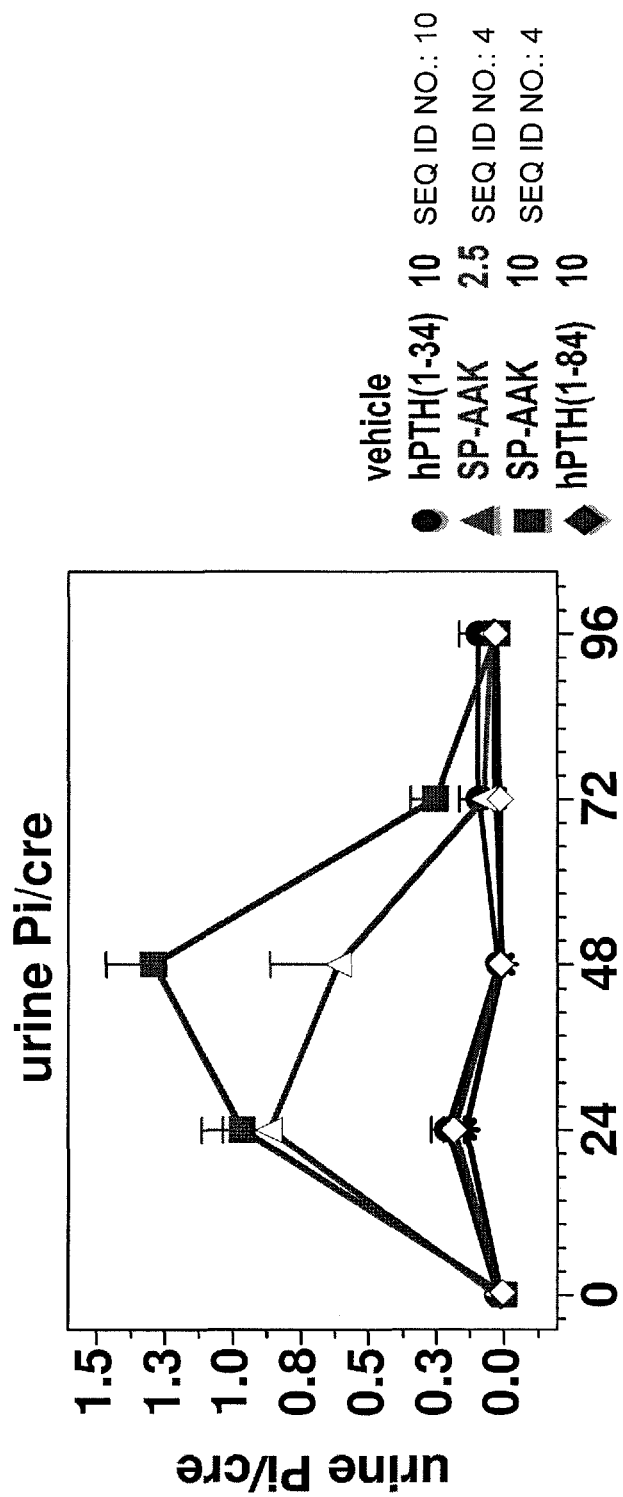

Similar experiments were performed using subcutaneous injection of the polypeptides using two different doses (2.5 nmol/kg or 10 nmol/kg; FIG. 14). From these experiments, increases in serum calcium were observed in a dose dependent manner with both SP-PTH (SEQ ID NO:11) and SP-PTH-AAK (SEQ ID NO:4) (FIG. 15A). Reductions in serum inorganic phosphate were also observed (FIGS. 15B and 15C). FIG. 15D shows increases in serum creatinine levels. Urine calcium and phosphate data were also collected. These data are from the same experiment shown in FIGS. 15A-15D. Urine was collected in 24-hour intervals prior to injection (T=0) and at times thereafter and assessed for Ca (FIGS. 15E and 15G), Pi (FIGS. 15F and 15H) and creatinine; [Ca] and [PI] are expressed as ratios to [creati-

TABLE 3

Peptide pharmacokinetics.

| | | $t_{1/2}$ min | AUClast min * pmol/mL | AUCinf min * pmol/mL | CL mL/min/kg | Vss ml/kg | MRT min |
|---|---|---|---|---|---|---|---|
| SP-PTH + AAK | mean | 7.27 | 1124 | 1131 | 21.6 | 126 | 5.83 |
| (SEQ ID NO: 5) | SD | 1.74 | 93.1 | 90.8 | 1.66 | 20.5 | 0.675 |
| hPTH (1-34) | mean | 7.78 | 1308 | 1315 | 18.5 | 211 | 11.4 |
| (SEQ ID NO: 10) | SD | 0.412 | 45.9 | 45.5 | 0.642 | 16.3 | 0.672 |
| hPTH (1-84) | mean | 5.44 | 1663 | 1663 | 17.2 | 66.2 | 3.58 |
| | SD | 1.30 | 898 | 898 | 7.12 | 38.9 | 1.09 |

Example 6

Hypercalcemic Assay in Cynomolgus Monkeys

Figure 11A:
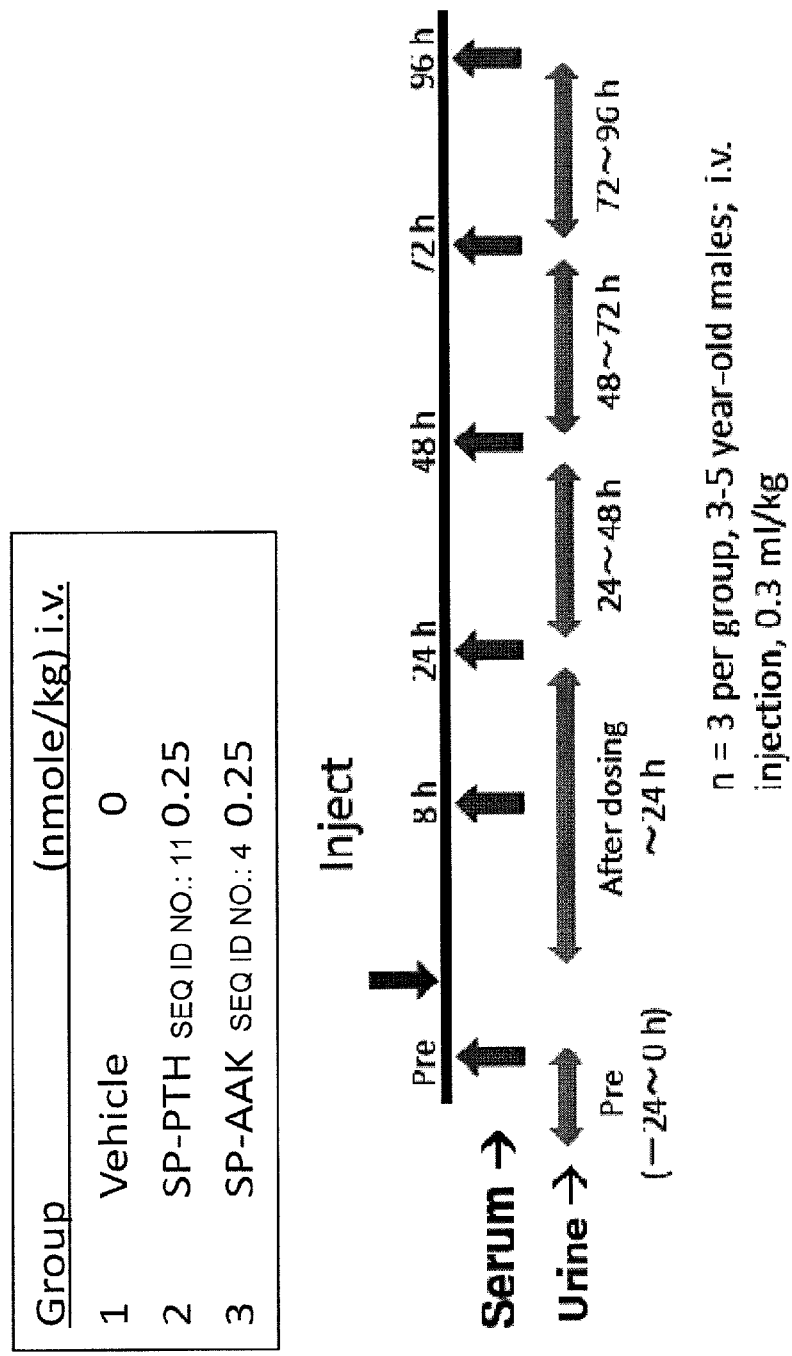
FIG. 11A is a schematic diagram showing the experimental protocol used in measuring serum and urinary calcium and phosphate levels in cynomolgus monkeys receiving an intravenous injection of SP-PTH (SEQ ID NO:11) or SP-PTH-AAK (SEQ ID NO:4).
Figure 11B:
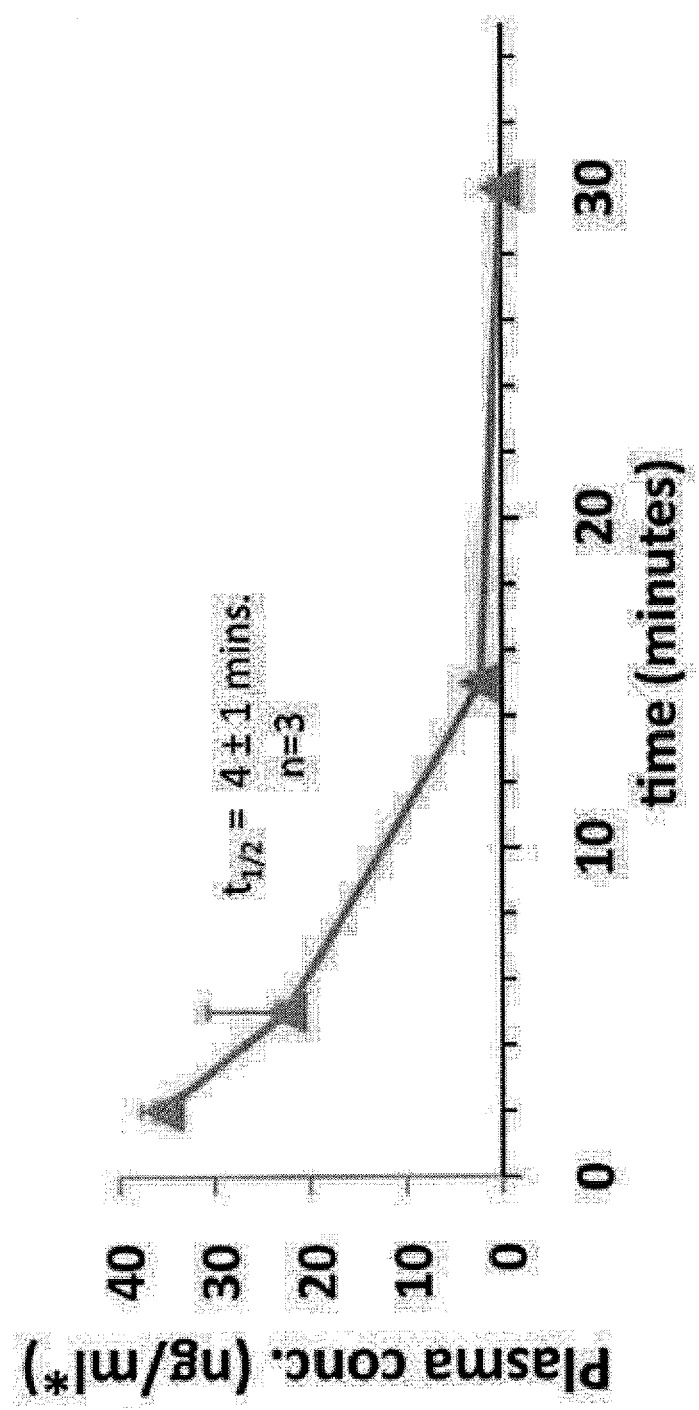
FIG. 11B is a graph showing plasma concentration of SP-PTH (SEQ ID NO:11) in monkey following intravenous injection of 1 nmol/kg.

The effects of the SP-PTH (SEQ ID NO:11) and SP-PTH-AAK (SEQ ID NO:4) ("SP-AAK") on serum and urinary calcium and phosphate levels were tested in cynomolgus monkeys. Briefly, three- or four-year-old, male cynomolgus monkeys (HAMRI Co., Ltd., Ibaraki, Japan) were measured for their body weight. Blood was collected into tubes. Monkeys received intravenous or subcutaneous administration of each polypeptide at a dose of 0.3 ml/kg. Polypeptide concentrations in stock solution were adjusted by dilution with 25 mmol/L phosphate-citrate buffer/100 mmol/L NaCl/0.05% Tween 80 (pH.5.0) (PC-buffer). All polypeptides were allowed to stand on ice immediately before administration. Polypeptides were administered to groups of three monkeys each respectively. At 1, 2, 4, and 8 hours after administration, blood was collected by saphenous vein to monitor the time course of calcium and phosphorus levels (FIG. 11A). SP-PTH (SEQ ID NO:11) was observed to have a plasma half-life of about 4 minutes (FIG. 11B).

Figure 12C:
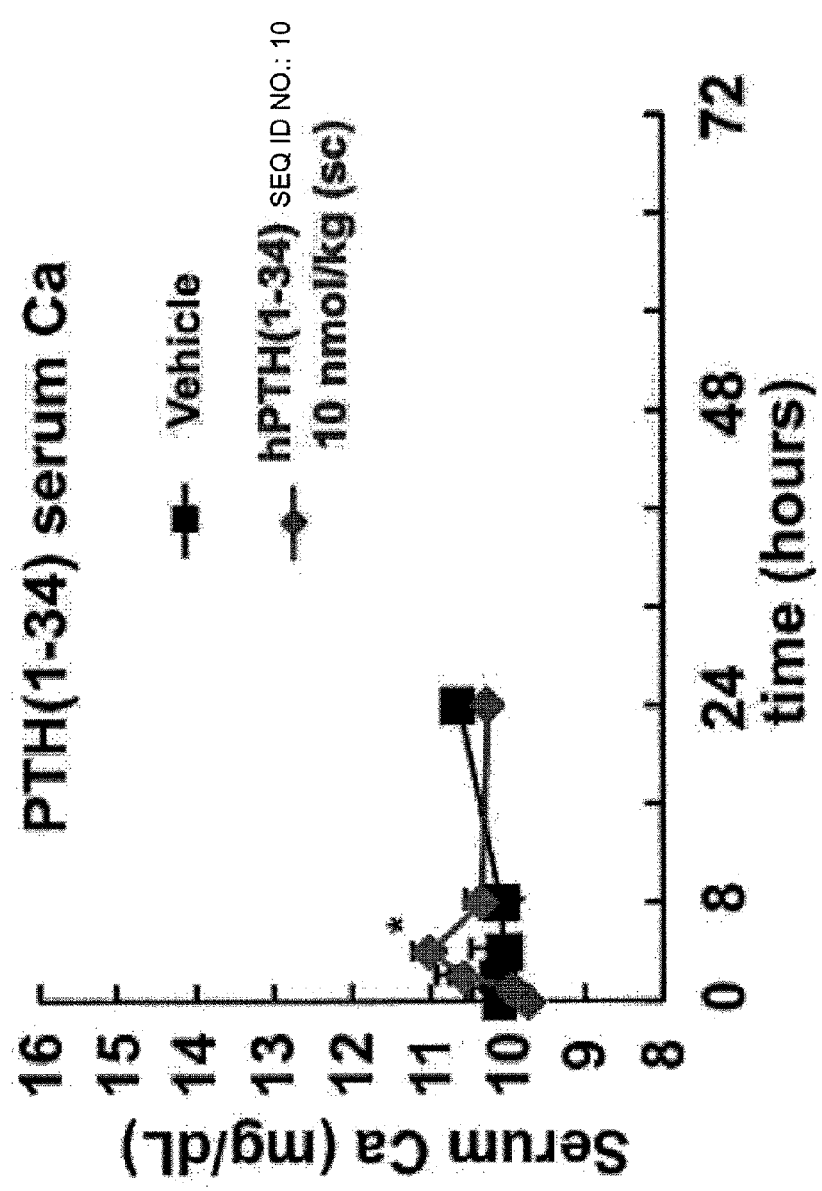
Figure 15G:
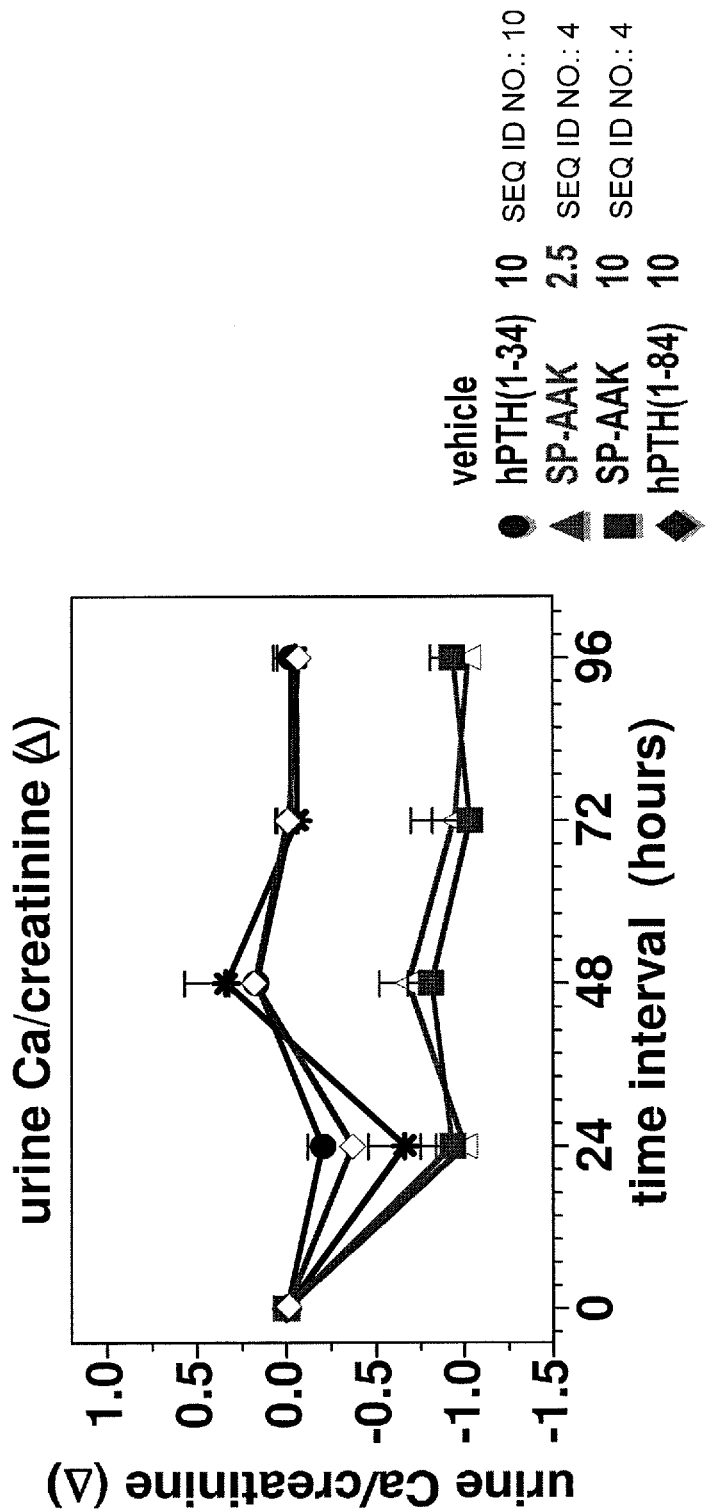
Figure 15H:
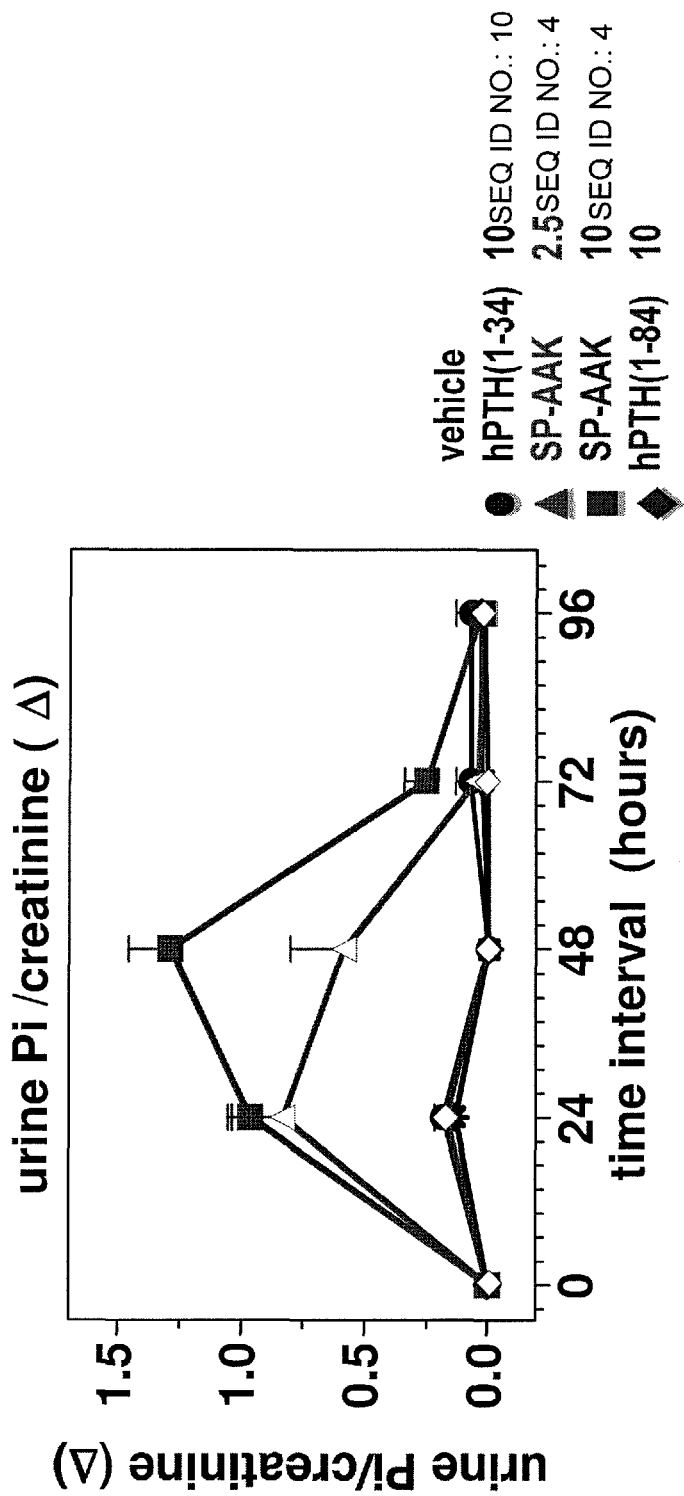

As shown in FIGS. 12A and 12B, injection of SP-PTH (SEQ ID NO:11) or SP-PTH-AAK (SEQ ID NO:4) increased serum calcium (FIG. 12A) for a substantial period of time following injection. Serum phosphate was similarly decreased (FIG. 12B). FIG. 12C shows, for comparison, the brief calcemic effect of PTH(1-34) (SEQ ID NO:10) give nine]. FIGS. 15G and 15H present the change from the pre-injection values. Data are means±s.e.m.; n=3/group.

Example 7

Solubility

The relative solubilities of SP-PTH-AAK (SEQ ID NO:4) and SP-PTH (SEQ ID NO:11) in different buffers were assessed in an in vitro precipitation assay. For each polypeptide, two vials, each containing 50 µg of lyophilized polypeptide powder, were prepared; one vial was reconstituted in 50 µl of PBS at pH 7.4; the other vial was reconstituted in 50 µl of 10 mM acetic acid (pH 2.9) to give final concentrations of 1.0 mg/ml or 1.5 mg/ml. After one hour at room temperature, the vials were centrifuged at 15,000×g for 2 minutes. The supernatant was removed and the protein content assayed using the Pierce BCA assay (Thermo Fischer Scientific, Rockford, Ill.). For each polypeptide, the content of the PBS sample was expressed as percent of the content of the corresponding acetic acid sample.

Figure 16A:
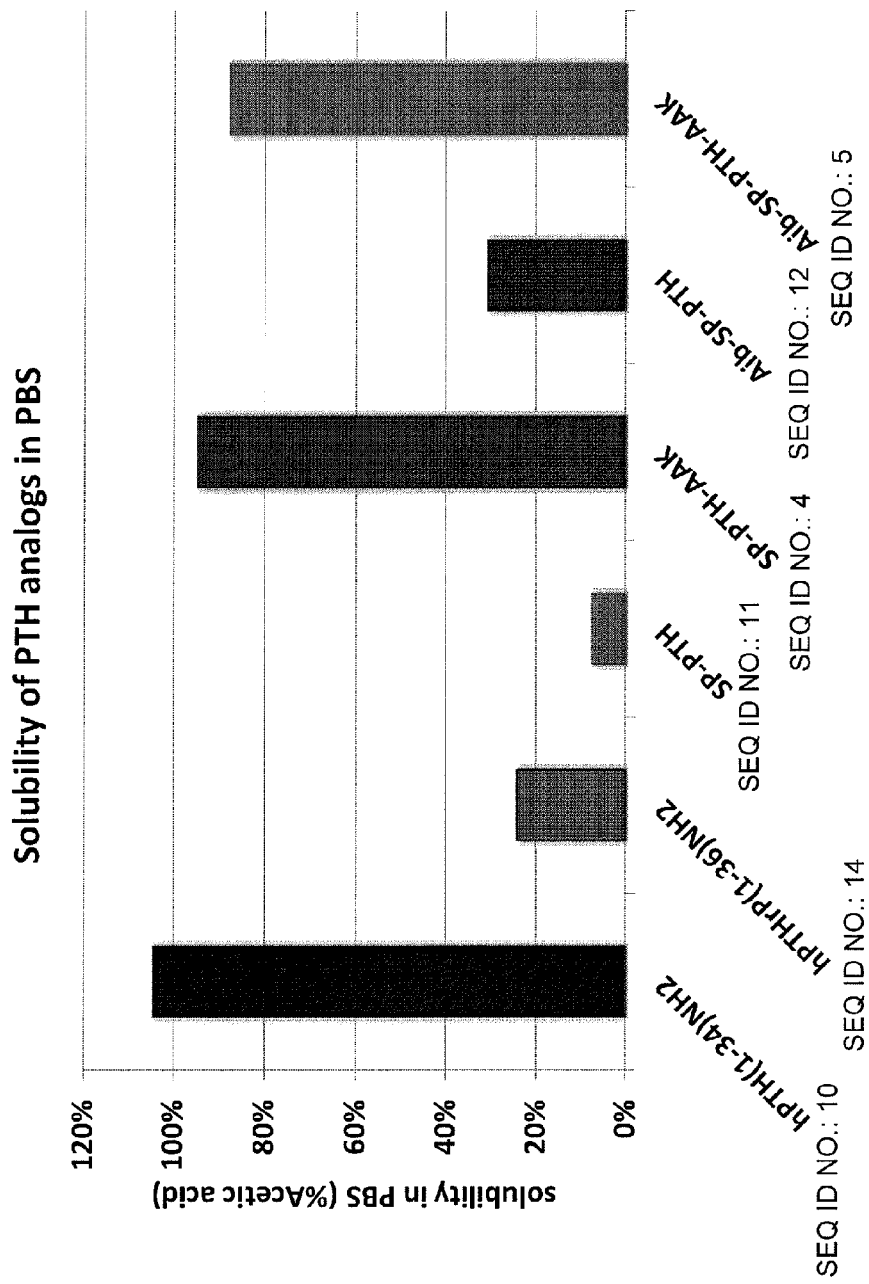
FIGS. 16A and 16B are graphs showing solubility of polypeptides in PBS solution at pH 7.4.
Figure 16B:
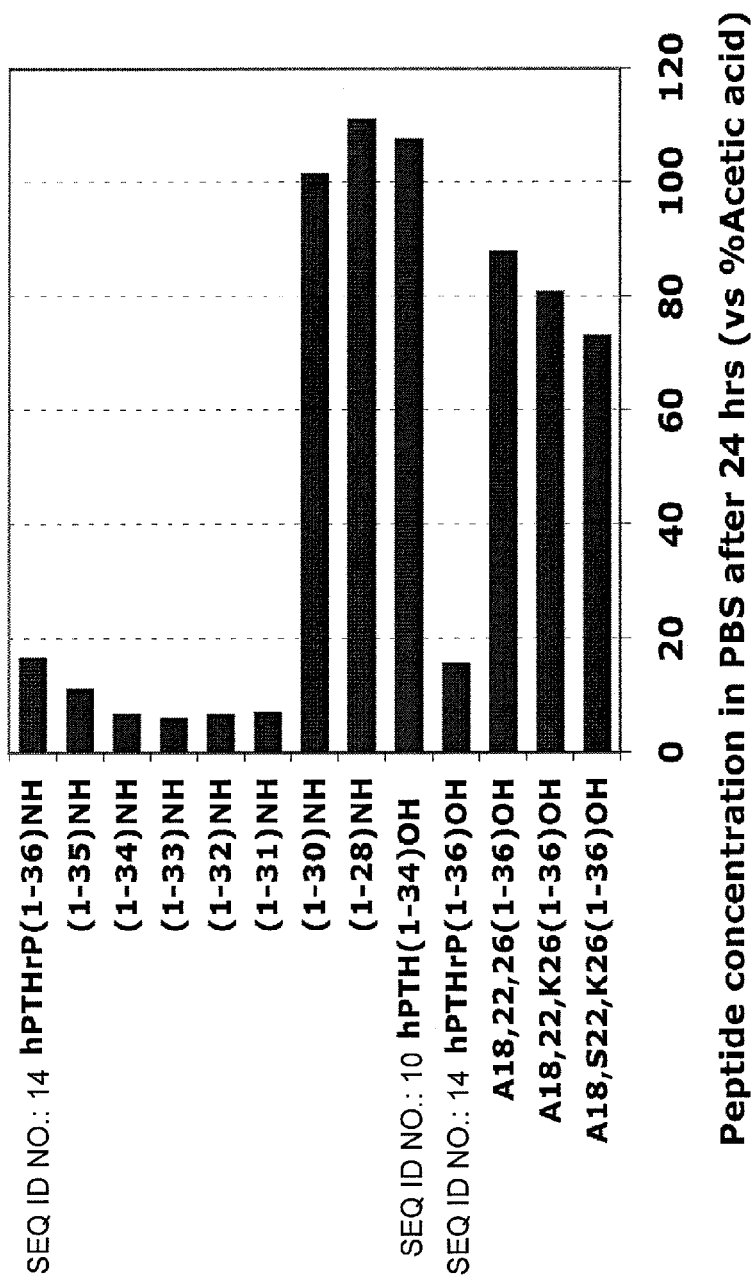
Figure 16C:
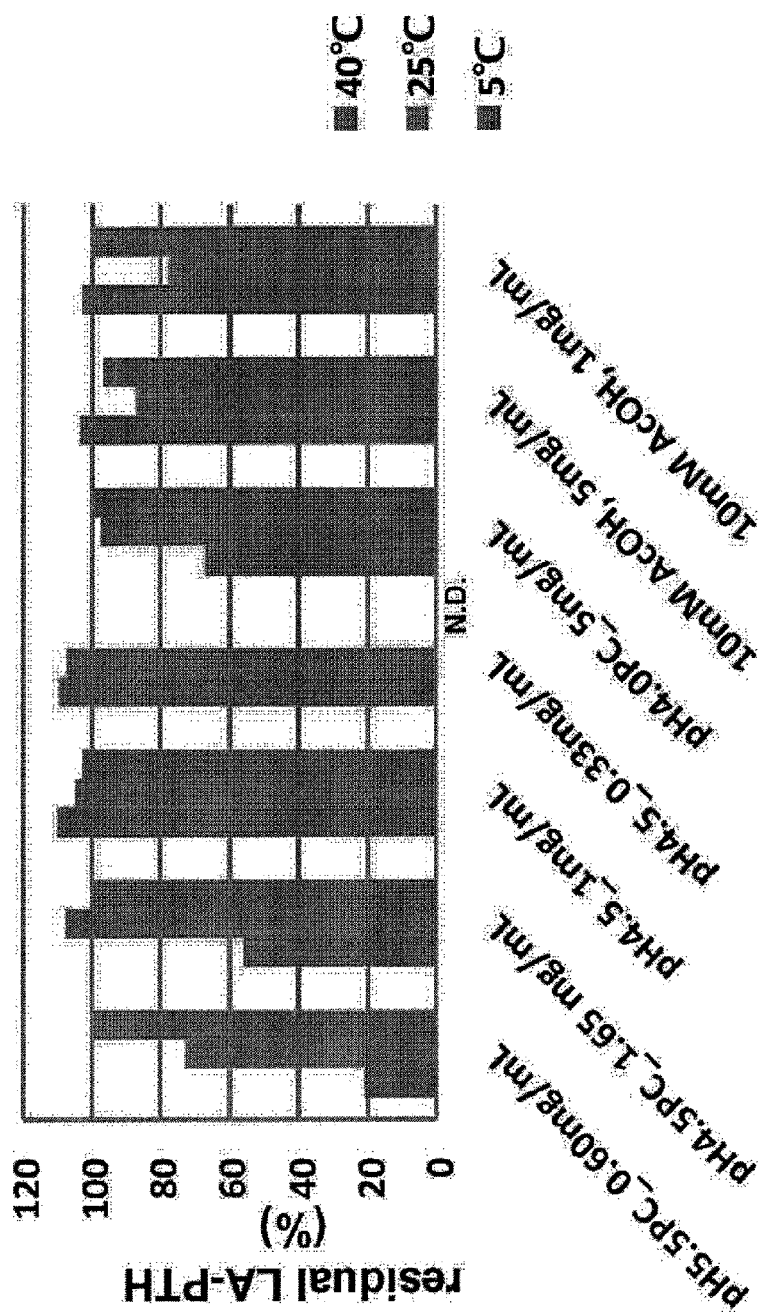
FIG. 16C shows stability of SP-PTH-AAK (SEQ ID NO:4) in phosphate-citrate buffers and in 10 mM acetic acid at 5, 25, and 40° C. The amount of intact SP-PTH-AAK (SEQ ID NO:4) peptide remaining in the sample, as compared to the starting sample, was measured by rPHPLC.

As shown in FIG. 16A, the SP-PTH-AAK (SEQ ID NO:4) and SP-Aib-PTH-AAK (SEQ ID NO:5) polypeptides exhibited solubility similar to hPTH(1-34)NH$_2$ (SEQ ID NO:10). Solubility testing of hPTHrP, fragments, and analogs is shown in FIG. 16B. Stability testing of SP-PTH-AAK (SEQ ID NO:4) was also performed. SP-PTH-AAK (SEQ ID NO:4) was stored at different peptide concentrations in 50 mM phosphate-citrate (PC) buffer (pH 4.0, 4.5, and 5.5) and 10 mM acetic acid at 5, 25, and 40° C. for 4 weeks. Analysis of intact peptide by reverse-phase HPLC revealed near full stability at 25° C. for 4 weeks (FIG. 16C). At 40° C., a degraded product, likely a methionine-oxide derivative, was detected on the HPLC chromatograms as shoulder of the main peak.

Example 8

Effect at Phosphorylation-Deficient (PD) PTH Receptors

The activity of SP-PTH-AAK (SEQ ID NO:4) was tested in "knock-in" mice that express a PD PTH receptor in place of the wild-type PTH receptor (Bounoutas et al., Endocrinology 147: 4674, 2006). As explained by Bounoutas, the PD receptors exhibit deficient internalization, which can lead to prolonged cAMP signaling.

Figure 17A:
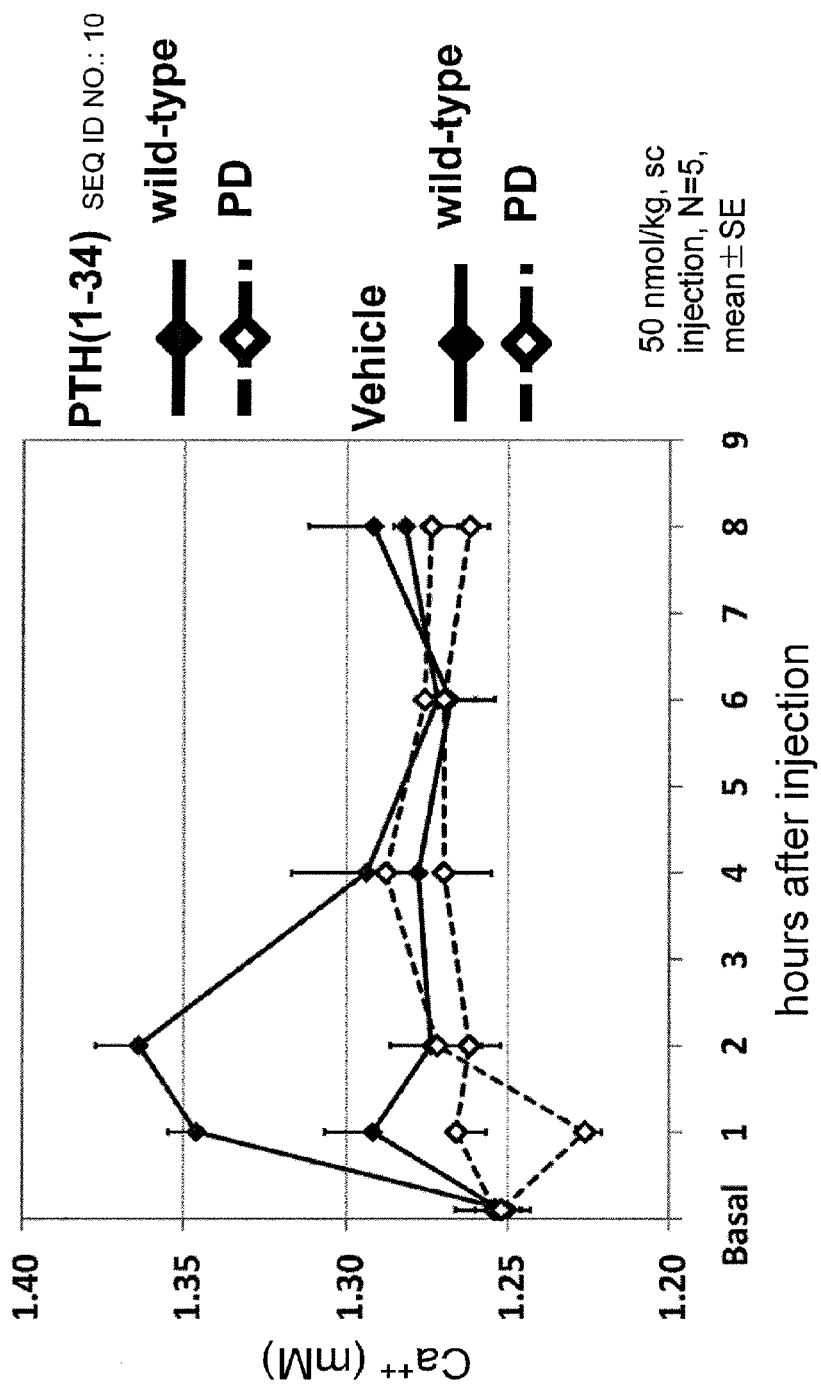
FIGS. 17A and 17B are graphs showing the effect of PTH(1-34) (SEQ ID NO:10) (FIG. 17A) and M-PTH(1-28) (FIG. 17B) on blood calcium levels in mice that express either the wild-type or phosphorylation-deficient (PD) PTH receptor.
Figure 17B:
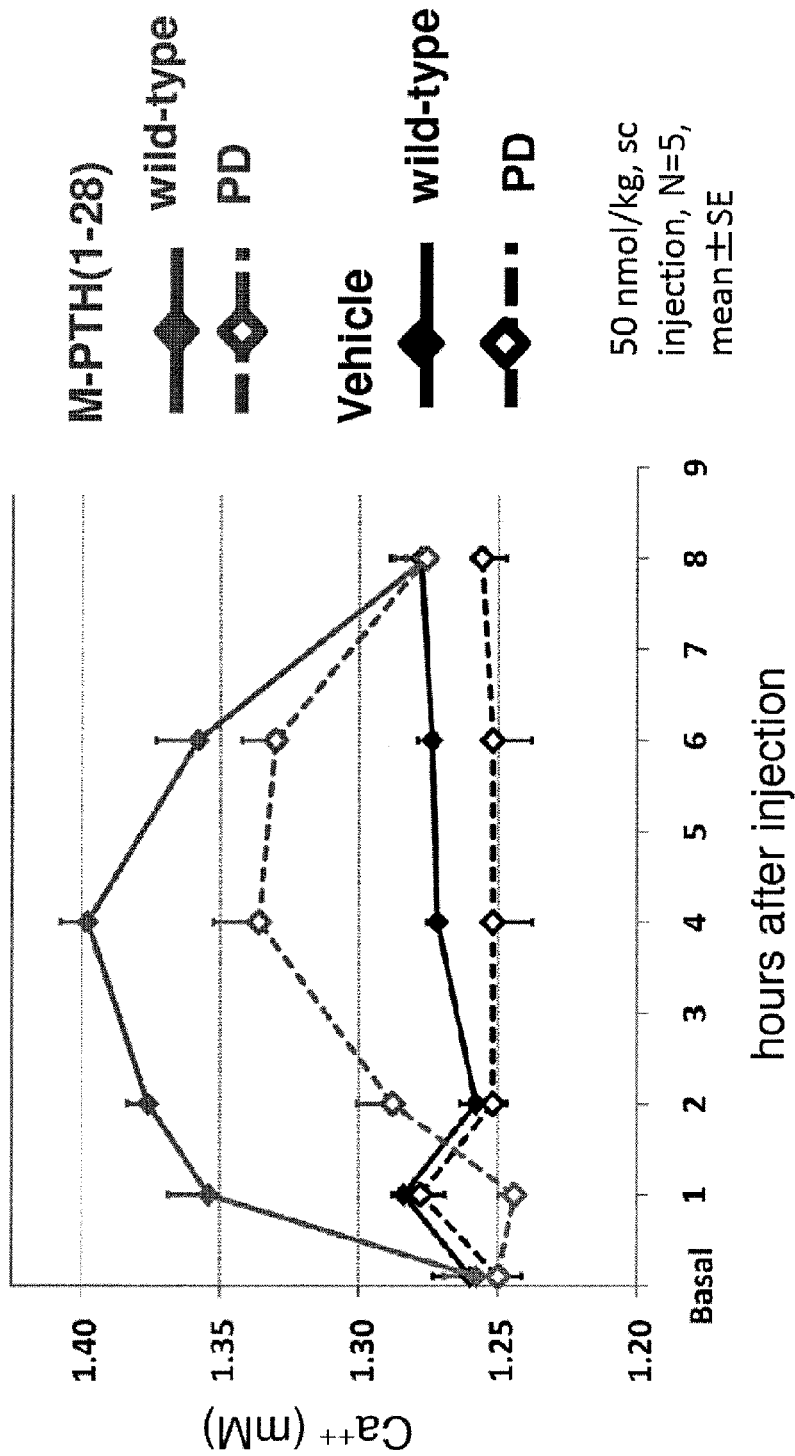

Both wild-type PTH(1-34) (SEQ ID NO:10) and the more potent M-PTH(1-28) were tested for their ability to alter blood calcium levels in wild-type and PD mice. As shown in FIGS. 17A and 17B, increases in blood calcium levels were either reduced or eliminated in the PD mice as compared to wild-type mice.

Figure 18A:
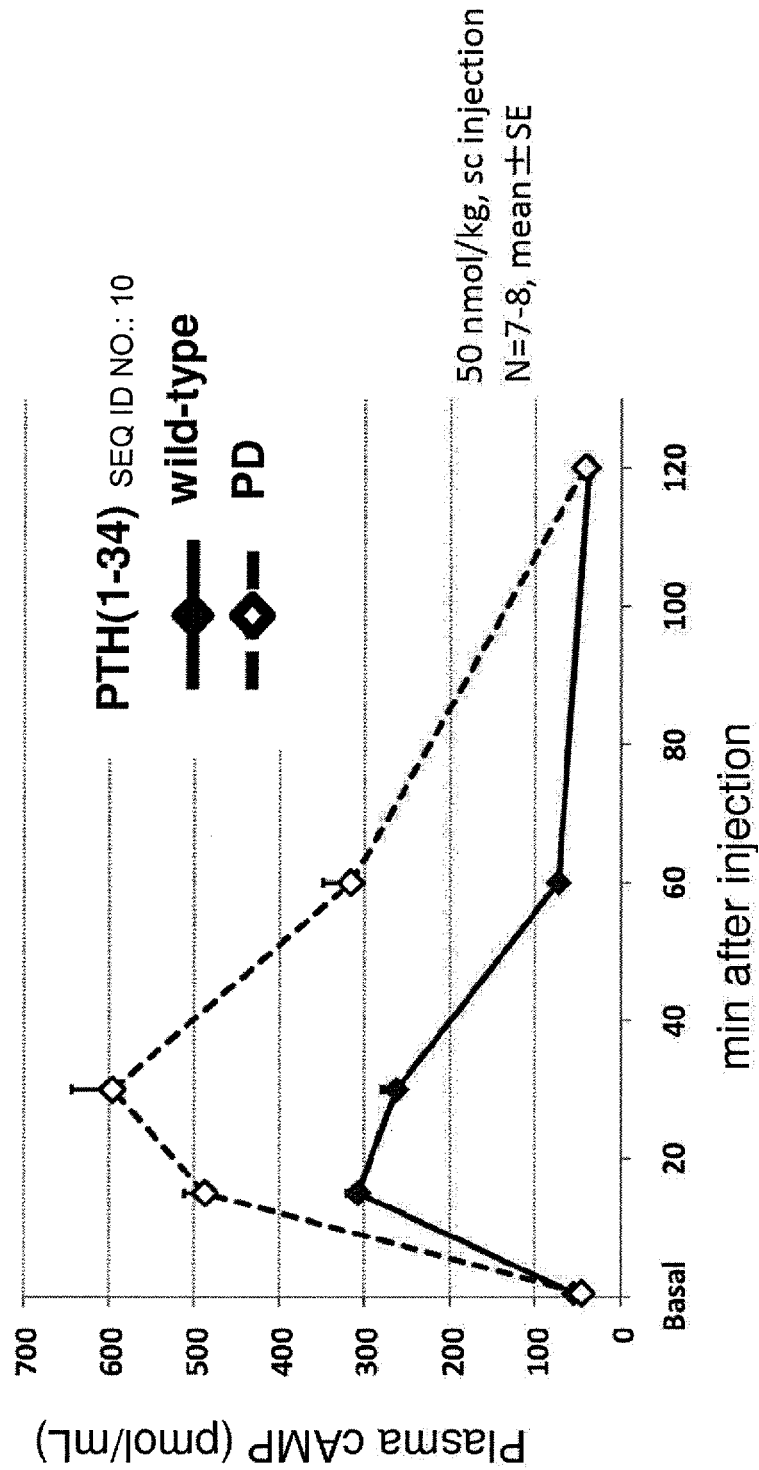
FIGS. 18A and 18B are graphs showing the effect of PTH(1-34) (SEQ ID NO:10) (FIG. 18A) and M-PTH(1-28) (FIG. 18B) on blood cAMP levels in mice that express either the wild-type or PD PTH receptor.
Figure 18B:
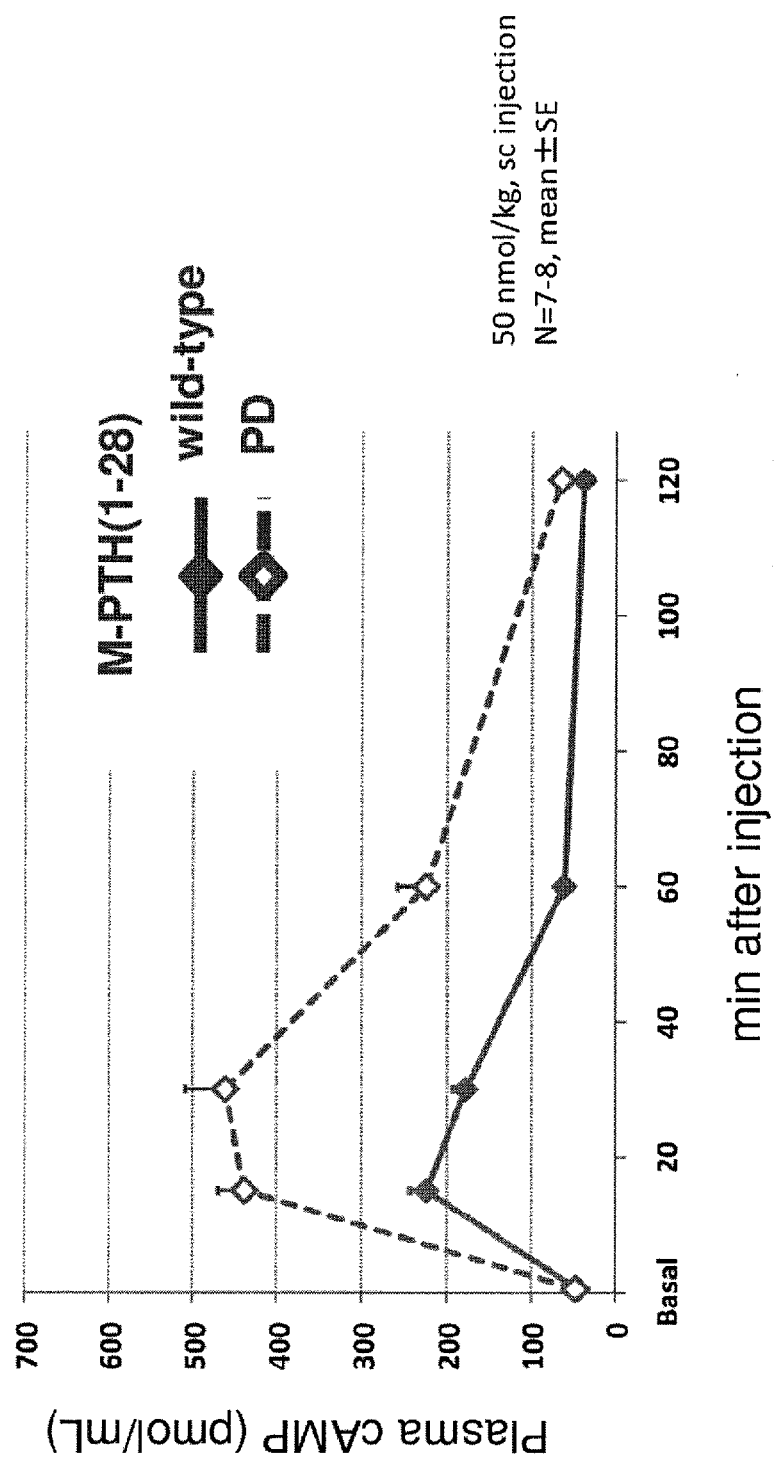

Blood cAMP levels were also compared between the two types of mice. For wild-type PTH(1-34) (SEQ ID NO:10) and for M-PTH(1-28), blood cAMP levels were increased in magnitude and prolonged in duration in the PD mice as compared to the wild-type mice (FIGS. 18A and 18B).

Figure 19:
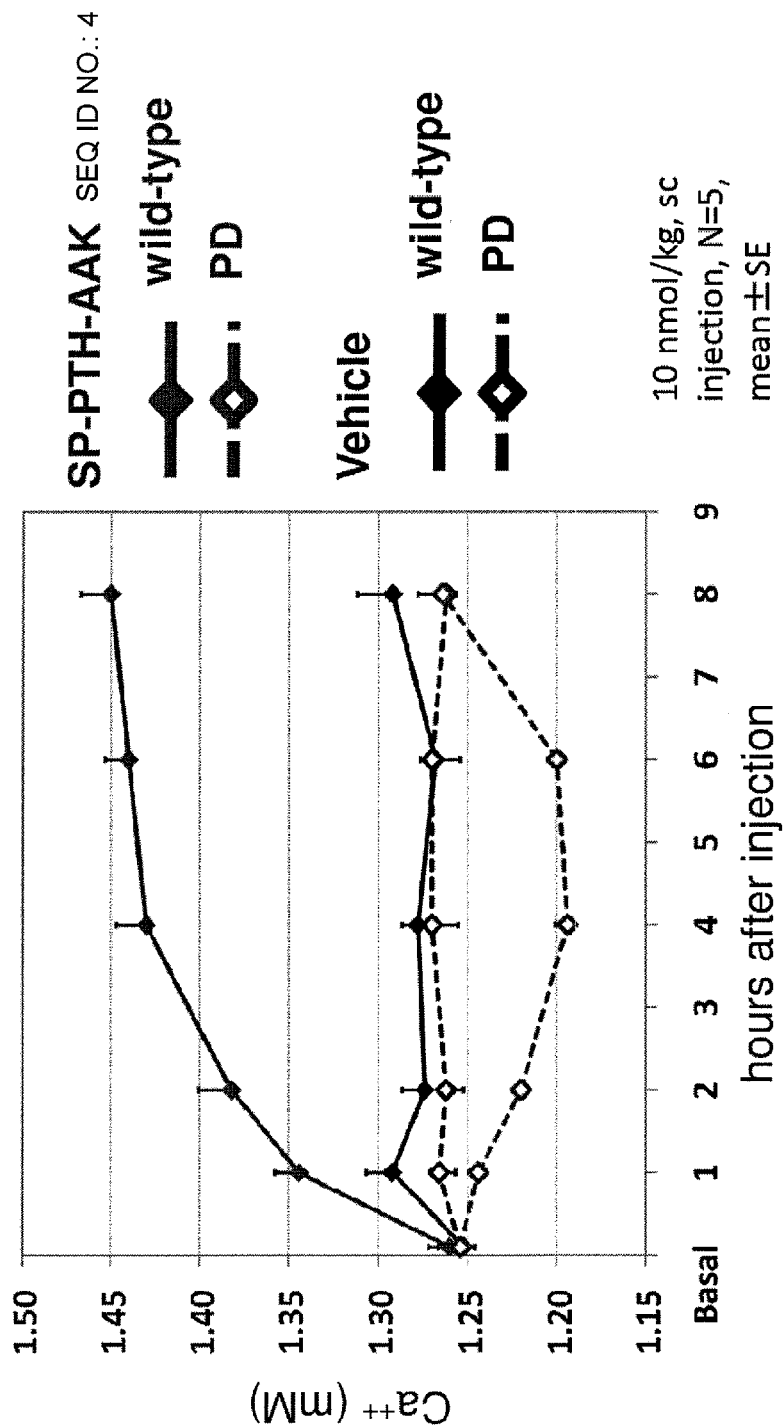
FIG. 19 is a graph showing the effect of SP-PTH-AAK (SEQ ID NO:4) on blood calcium levels in mice that expression either the wild-type or PD PTH receptor.

The effect of SP-PTH-AAK (SEQ ID NO:4) on blood calcium levels in wild-type and PD mice is shown in FIG. 19. Surprisingly, SP-PTH-AAK (SEQ ID NO:4) reduced blood calcium level for at least six hours after injection and never rose above the levels seen with the vehicle control.

Example 9

Repetitive Daily Dosing in TPTX Rats

Figure 20A:
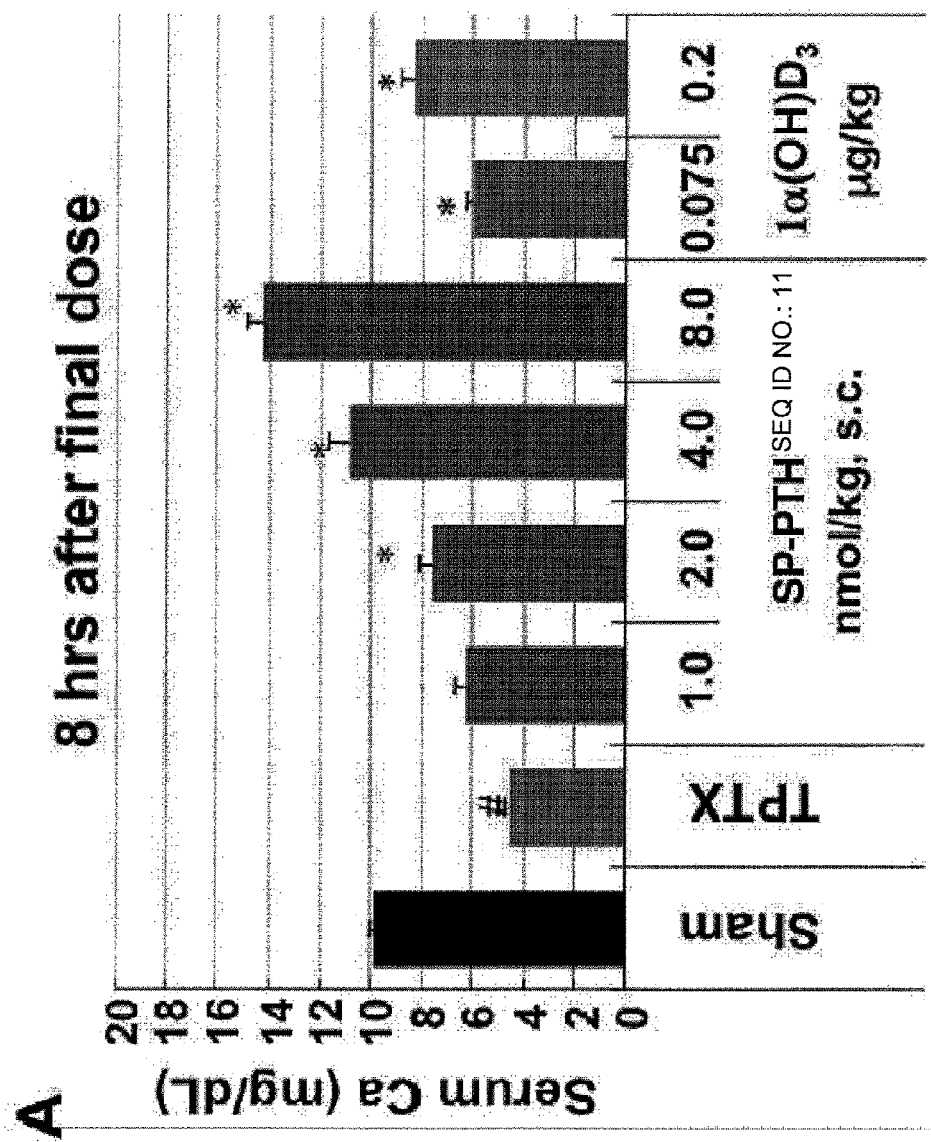
FIGS. 20A-20D are graphs showing effects of once-daily SP-PTH on serum and urine Ca in TPTX rats. TPTX and sham-control rats were treated once daily, for 10 days, via sc. injection with either vehicle (Sham and TPTX) or SP-PTH (SEQ ID NO:11) (1, 2. 4, or 8 nmol/kg), or with 1,25(OH)$_2$D (0.075 or 0.2 µg/kg. orn). After the last injection on day 10, the rats were placed in metabolic cages, and jugular vein blood was obtained at 8 (FIG. 20A) and 24 hrs (FIG. 20B); urine was collected for the intervals 0-8 (FIG. 20C) and 8-24 hrs (FIG. 20D); means±s.e.m: n=5; '~, P vs vehicle <005.
Figure 20B:
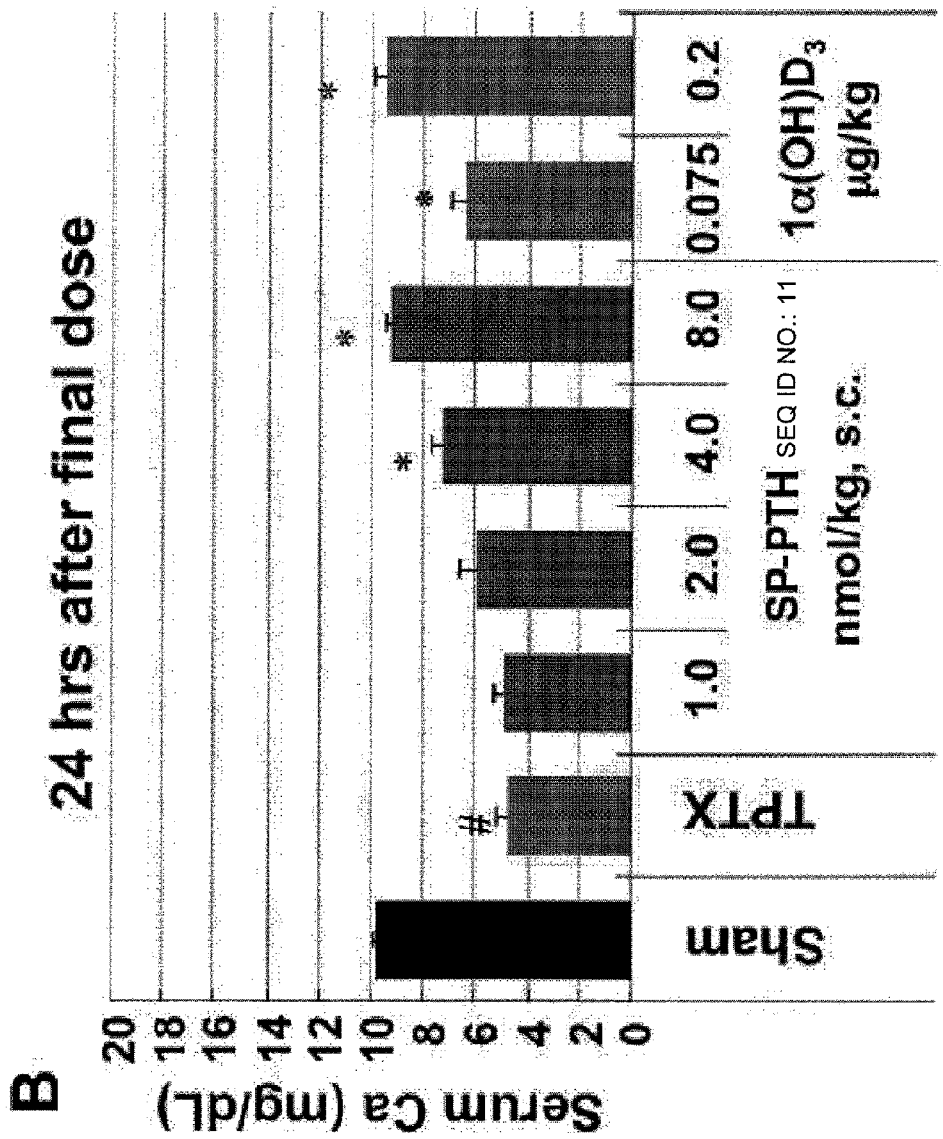
Figure 20C:
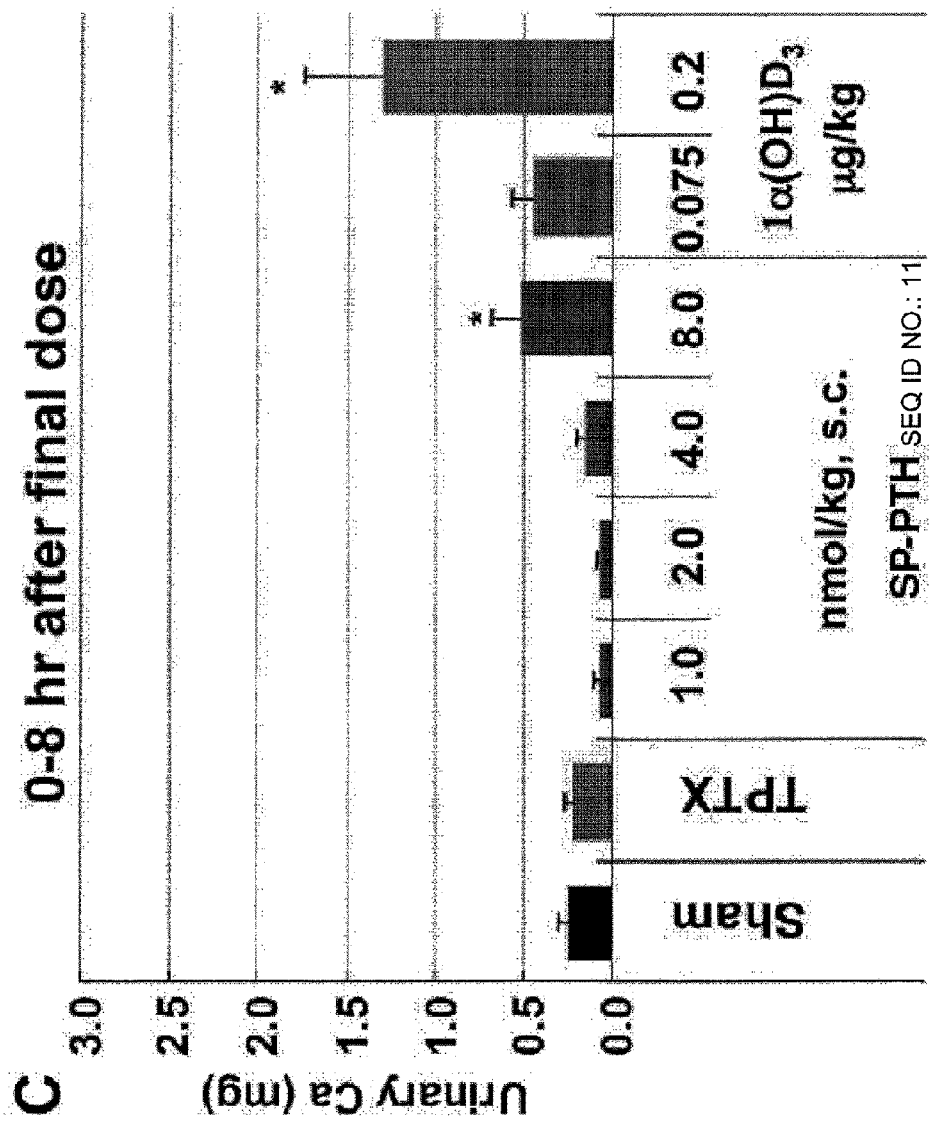
Figure 20D:
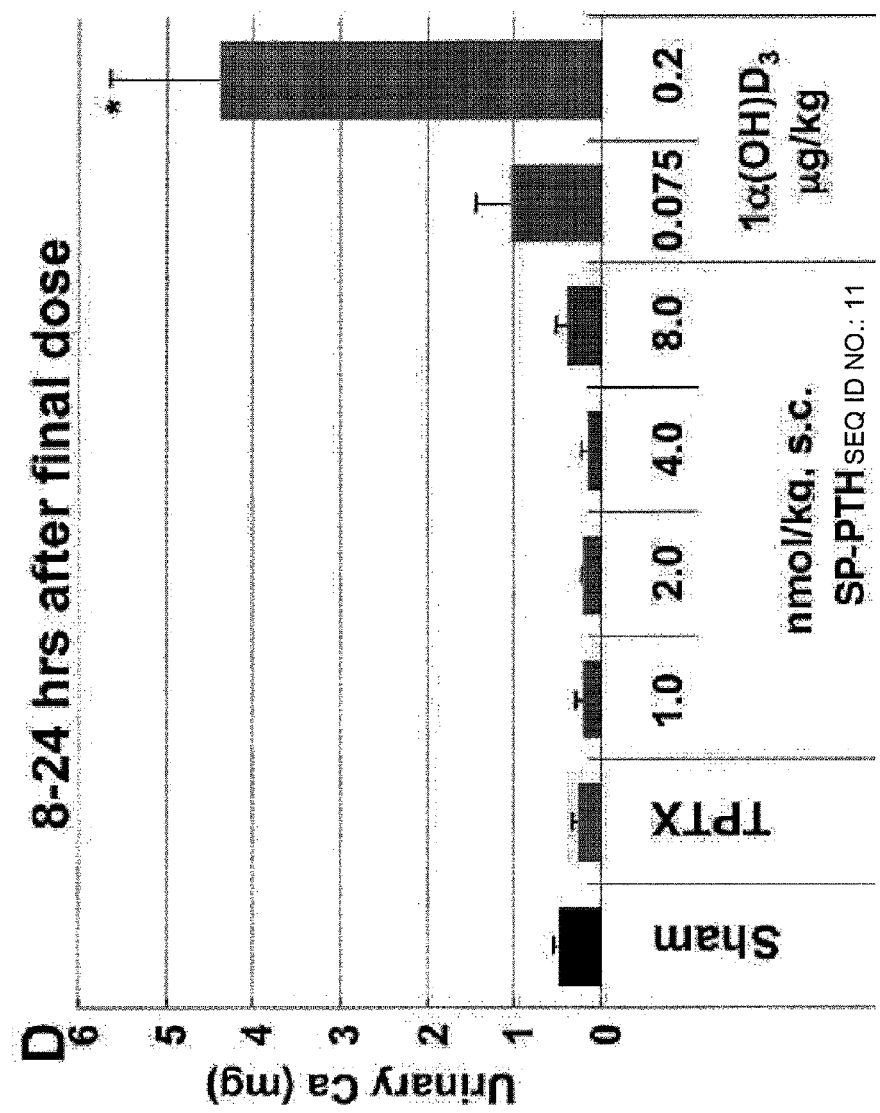

Our single injection experiments performed in rodents and monkeys revealed biological activities lasting, in some cases, for more than 24 hours, we believe hyperprolonged in these experiments due to the high doses used, as indicated by the marked hypercalcemia. In therapeutic use in humans, one would administer doses sufficient to only normalize blood Ca. A key experiment is to determine if it is indeed feasible to normalize sCa following a repetitive dosing regimen. We thus performed the experiment of FIGS. 20A-2D, in which TPTX rats were treated daily for 10 days with SP-PTH at doses of 1, 2, 4 and 8 nmol/kg (s.c). For comparison, $1,25(OH)_2$-vitamin-D (calcitriol) at doses of 0.075 and 0.2 mcg/kg (oral) were used for the same time periods. In this study, the 4 nmol/kg dose of SP-PTH (SEQ ID NO:11) gave the most satisfactory control of sCa, as it both avoided hypercalcemia at 8 hours after the last injection (FIG. 20A), and it maintained near-normal sCa at 24 hours (FIG. 20B). Impressively, urine calcium excretion was low at all time points with the 4 nmol/kg dose of SP-PTH (SEQ ID NO:11), which contrasts with elevated urine calcium with calcitriol at 0.2 µg/kg, the dose needed to achieve sCa in the 8-9 mg/dl range (FIGS. 20C and 20D).

Statistical Analysis

The data described above are generally represented as the mean±standard error (SEM). Statistical significance was determined using SAS software (Ver.5.00.010720, SAS Institute Japan, Tokyo, Japan). A difference in p values of <0.05 was considered statistically significant. *P<0.05, P<0.01, *P<0.001.

OTHER EMBODIMENTS

All patents, patent applications, and publications mentioned in this specification, including U.S. Application No. 61/334,319, filed May 13, 2010, and 61/415,141, filed Nov. 18, 2010, are hereby incorporated by reference to the same extent as if each independent patent, patent application, or publication was specifically and individually indicated to be incorporated by reference.

The invention claimed is:

1. A polypeptide comprising formula (I):

(I) SEQ ID NO: 1
$X_{01}$-Val-$X_{03}$-Glu-Ile-Gln-Leu-$X_{08}$-His-$X_{10}$-$X_{11}$-$X_{12}$-$X_{13}$-$X_{14}$-$X_{15}$-$X_{16}$-$X_{17}$-$X_{18}$-Arg-Arg-Arg-$X_{22}$-Phe-Leu-$X_{25}$-$X_{26}$-Leu-Ile-Ala-Glu-Ile-His-Thr-Ala-Glu-Ile $X_{01}$ is Ser or Ala;
$X_{03}$ is Ser, Ala, or Aib;
$X_{08}$ is Met, Leu, or Nle;
$X_{10}$ is Asn or Gln;
$X_{11}$ is Leu, Arg, or Har;
$X_{12}$ is Gly or Ala;
$X_{13}$ is Lys;
$X_{14}$ is His or Trp;
$X_{15}$ is Ile;
$X_{16}$ is Gln;
$X_{17}$ is Asp;
$X_{18}$ is Ala;
$X_{22}$ is Ala;
$X_{25}$ is His; and
$X_{26}$ is Lys;
or a pharmaceutically acceptable salt thereof.

2. The polypeptide of claim 1, wherein $X_{01}$ and $X_{03}$ are Ala; $X_{10}$ is Gln; $X_{11}$ is Arg; $X_{12}$ is Ala; and $X_{14}$ is Trp.

3. The polypeptide of claim 1, wherein $X_{01}$ is Ala; $X_{03}$ is Aib; $X_{10}$ is Gln; $X_{11}$ is Har; $X_{12}$ is Ala; and $X_{14}$ is Trp.

4. The polypeptide of claim 1, wherein said polypeptide is fewer than 50 amino acids in length.

5. The polypeptide of claim 1, or a pharmaceutically acceptable salt thereof, comprising the amino acid sequence:

(SEQ ID NO: 4)
Ala-Val-Ala-Glu-Ile-Gln-Leu-Met-His-Gln-Arg-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile.

6. The polypeptide of claim 1, or a pharmaceutically acceptable salt thereof, comprising the amino acid sequence:

(SEQ ID NO: 5)
Ala-Val-Aib-Glu-Ile-Gln-Leu-Met-His-Gln-Har-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile.

7. The polypeptide of claim 1, or a pharmaceutically acceptable salt thereof, comprising an amino acid sequence selected from the group consisting of:

(SEQ ID NO: 6)
Ala-Val-Ala-Glu-Ile-Gln-Leu-Nle-His-Gln-Arg-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile;

(SEQ ID NO: 7)
Ala-Val-Ala-Glu-Ile-Gln-Leu-Leu-His-Gln-Arg-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile;

(SEQ ID NO: 8)
Ala-Val-Aib-Glu-Ile-Gln-Leu-Nle-His-Gln-Har-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile; and (SEQ ID NO: 9)
Ala-Val-Aib-Glu-Ile-Gln-Leu-Leu-His-Gln-Har-Ala-Lys-Trp-Ile-Gln-Asp-Ala-Arg-Arg-Arg-Ala-Phe-Leu-His-Lys-Leu-Ile-Ala-Glu-Ile-His-Thr-Ala-Glu-Ile.

8. A pharmaceutical composition comprising a polypeptide of claim 1 and a pharmaceutically acceptable carrier.

9. A method for treating a subject having a disease selected from the group consisting of hypoparathyroidism, hyperphosphatemia, osteoporosis, fracture repair, osteomalacia, arthritis, and thrombocytopenia, said method comprising administering a polypeptide of claim 1 to said subject in an amount sufficient to treat said disease.

10. The method of claim 9, wherein the route of administration is selected from the group consisting of subcutaneously, intravenously, intranasally, transpulmonarily, transdermally, and orally.

* * * * *

SEQUENCE LISTING

```
<160> NUMBER OF SEQ ID NOS: 15

<210> SEQ ID NO 1
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser, Ala, or Aib
<220> FEATURE:
<221> NAME/KEY: MOD_RES
<222> LOCATION: (3)..(3)
<223> OTHER INFORMATION: Ser, Ala, or Aib
<220> FEATURE:
<221> NAME/KEY: MOD_RES
<222> LOCATION: (8)..(8)
<223> OTHER INFORMATION: Met, Leu, or Nle
<220> FEATURE:
<221> NAME/KEY: MOD_RES
<222> LOCATION: (10)..(10)
<223> OTHER INFORMATION: Asn, Ala, Val, Asp, Glu, or Gln
<220> FEATURE:
<221> NAME/KEY: MOD_RES
<222> LOCATION: (11)..(11)
<223> OTHER INFORMATION: Leu, Ala, Val, Met, Lys, Ile, Arg, Har, or Trp
```

```
<220> FEATURE:
<221> NAME/KEY: MOD_RES
<222> LOCATION: (12)..(12)
<223> OTHER INFORMATION: Gly, Ala, His, or Arg
<220> FEATURE:
<221> NAME/KEY: MOD_RES
<222> LOCATION: (13)..(13)
<223> OTHER INFORMATION: Lys, Ala, Leu, Gln, Arg, His, or Trp
<220> FEATURE:
<221> NAME/KEY: MOD_RES
<222> LOCATION: (14)..(14)
<223> OTHER INFORMATION: His, Leu, Arg, Phe, Trp, or Ser
<220> FEATURE:
<221> NAME/KEY: MOD_RES
<222> LOCATION: (15)..(15)
<223> OTHER INFORMATION: Ile or Leu
<220> FEATURE:
<221> NAME/KEY: MOD_RES
<222> LOCATION: (16)..(16)
<223> OTHER INFORMATION: Gln or Asn
<220> FEATURE:
<221> NAME/KEY: MOD_RES
<222> LOCATION: (17)..(17)
<223> OTHER INFORMATION: Asp or Ser
<220> FEATURE:
<221> NAME/KEY: MOD_RES
<222> LOCATION: (18)..(18)
<223> OTHER INFORMATION: Ala, Leu, Met, Glu, Ser, or Phe
<220> FEATURE:
<221> NAME/KEY: MOD_RES
<222> LOCATION: (22)..(22)
<223> OTHER INFORMATION: Ala, Phe, Glu, Ser, Leu, Asn, Trp, or Lys
<220> FEATURE:
<221> NAME/KEY: MOD_RES
<222> LOCATION: (25)..(25)
<223> OTHER INFORMATION: His, Arg, Leu, Trp, or Lys
<220> FEATURE:
<221> NAME/KEY: MOD_RES
<222> LOCATION: (26)..(26)
<223> OTHER INFORMATION: Lys, His, Ala, Ser, Asn, or Arg

<400> SEQUENCE: 1

Xaa Val Xaa Glu Ile Gln Leu Xaa His Xaa Xaa Xaa Xaa Xaa Xaa
1               5                   10                  15

Xaa Xaa Arg Arg Arg Xaa Phe Leu Xaa Xaa Leu Ile Ala Glu Ile His
                20                  25                  30

Thr Ala Glu Ile
            35

<210> SEQ ID NO 2
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser, Ala, or Aib
<220> FEATURE:
<221> NAME/KEY: MOD_RES
<222> LOCATION: (3)..(3)
<223> OTHER INFORMATION: Ser, Ala, or Aib
<220> FEATURE:
<221> NAME/KEY: MOD_RES
<222> LOCATION: (8)..(8)
<223> OTHER INFORMATION: Met, Leu, or Nle
<220> FEATURE:
<221> NAME/KEY: MOD_RES
<222> LOCATION: (10)..(10)
<223> OTHER INFORMATION: Asn, Gln, or Asp
<220> FEATURE:
<221> NAME/KEY: MOD_RES
<222> LOCATION: (11)..(11)
<223> OTHER INFORMATION: Leu, Arg, Har, or Lys
```

-continued

```
<220> FEATURE:
<221> NAME/KEY: MOD_RES
<222> LOCATION: (12)..(12)
<223> OTHER INFORMATION: Gly or Ala
<220> FEATURE:
<221> NAME/KEY: MOD_RES
<222> LOCATION: (14)..(14)
<223> OTHER INFORMATION: His, Trp, or Ser
<220> FEATURE:
<221> NAME/KEY: MOD_RES
<222> LOCATION: (15)..(15)
<223> OTHER INFORMATION: Ile or Leu
<220> FEATURE:
<221> NAME/KEY: MOD_RES
<222> LOCATION: (16)..(16)
<223> OTHER INFORMATION: Gln or Asn
<220> FEATURE:
<221> NAME/KEY: MOD_RES
<222> LOCATION: (17)..(17)
<223> OTHER INFORMATION: Asp or Ser
<220> FEATURE:
<221> NAME/KEY: MOD_RES
<222> LOCATION: (18)..(18)
<223> OTHER INFORMATION: Ala or Leu
<220> FEATURE:
<221> NAME/KEY: MOD_RES
<222> LOCATION: (22)..(22)
<223> OTHER INFORMATION: Ala or Phe
<220> FEATURE:
<221> NAME/KEY: MOD_RES
<222> LOCATION: (26)..(26)
<223> OTHER INFORMATION: Lys or His

<400> SEQUENCE: 2

Xaa Val Xaa Glu Ile Gln Leu Xaa His Xaa Xaa Xaa Lys Xaa Xaa Xaa
1               5                   10                  15

Xaa Xaa Arg Arg Arg Xaa Phe Leu His Xaa Leu Ile Ala Glu Ile His
            20                  25                  30

Thr Ala Glu Ile
        35

<210> SEQ ID NO 3
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser, Ala, or Aib
<220> FEATURE:
<221> NAME/KEY: MOD_RES
<222> LOCATION: (3)..(3)
<223> OTHER INFORMATION: Ser, Ala, or Aib
<220> FEATURE:
<221> NAME/KEY: MOD_RES
<222> LOCATION: (8)..(8)
<223> OTHER INFORMATION: Met, Leu, or Nle
<220> FEATURE:
<221> NAME/KEY: MOD_RES
<222> LOCATION: (10)..(10)
<223> OTHER INFORMATION: Asn or Gln
<220> FEATURE:
<221> NAME/KEY: MOD_RES
<222> LOCATION: (11)..(11)
<223> OTHER INFORMATION: Leu, Arg, or Har
<220> FEATURE:
<221> NAME/KEY: MOD_RES
<222> LOCATION: (12)..(12)
<223> OTHER INFORMATION: Gly or Ala
<220> FEATURE:
<221> NAME/KEY: MOD_RES
<222> LOCATION: (14)..(14)
<223> OTHER INFORMATION: His or Trp
```

```
<220> FEATURE:
<221> NAME/KEY: MOD_RES
<222> LOCATION: (16)..(16)
<223> OTHER INFORMATION: Gln or Asn
<220> FEATURE:
<221> NAME/KEY: MOD_RES
<222> LOCATION: (17)..(17)
<223> OTHER INFORMATION: Asp or Ser
<220> FEATURE:
<221> NAME/KEY: MOD_RES
<222> LOCATION: (18)..(18)
<223> OTHER INFORMATION: Ala or Leu
<220> FEATURE:
<221> NAME/KEY: MOD_RES
<222> LOCATION: (22)..(22)
<223> OTHER INFORMATION: Ala or Phe
<220> FEATURE:
<221> NAME/KEY: MOD_RES
<222> LOCATION: (26)..(26)
<223> OTHER INFORMATION: Lys or His

<400> SEQUENCE: 3

Xaa Val Xaa Glu Ile Gln Leu Xaa His Xaa Xaa Xaa Lys Xaa Ile Xaa
1               5                   10                  15

Xaa Xaa Arg Arg Arg Xaa Phe Leu His Xaa Leu Ile Ala Glu Ile His
            20                  25                  30

Thr Ala Glu Ile
        35

<210> SEQ ID NO 4
<211> LENGTH: 36
<212> TYPE: PRT
<213> ORGANISM: Artificial Sequence
<220> FEATURE:
<223> OTHER INFORMATION: Synthetic

<400> SEQUENCE: 4

Ala Val Ala Glu Ile Gln Leu Met His Gln Arg Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 5
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 5

Ala Val Xaa Glu Ile Gln Leu Met His Gln Xaa Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35
```

```
<210> SEQ ID NO 6
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (8)..(8)
<223> OTHER INFORMATION: Nle

<400> SEQUENCE: 6

Ala Val Ala Glu Ile Gln Leu Xaa His Gln Arg Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 7
<211> LENGTH: 36
<212> TYPE: PRT
<213> ORGANISM: Artificial Sequence
<220> FEATURE:
<223> OTHER INFORMATION: Synthetic

<400> SEQUENCE: 7

Ala Val Ala Glu Ile Gln Leu Leu His Gln Arg Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 8
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Har

<400> SEQUENCE: 8

Ala Val Xaa Glu Ile Gln Leu Xaa His Gln Xaa Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 9
<211> LENGTH: 36
<212> TYPE: PRT
<213> ORGANISM: Artificial Sequence
```

```
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 9

Ala Val Xaa Glu Ile Gln Leu Leu His Gln Xaa Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 10
<211> LENGTH: 34
<212> TYPE: PRT
<213> ORGANISM: Homo sapiens

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 11
<211> LENGTH: 36
<212> TYPE: PRT
<213> ORGANISM: Artificial Sequence
<220> FEATURE:
<223> OTHER INFORMATION: Synthetic

<400> SEQUENCE: 11

Ala Val Ala Glu Ile Gln Leu Met His Gln Arg Ala Lys Trp Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 12
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har
```

```
<400> SEQUENCE: 12

Ala Val Xaa Glu Ile Gln Leu Met His Gln Xaa Ala Lys Trp Ile Gln
1               5                   10                  15

Asp Leu Arg Arg Arg Phe Phe Leu His His Leu Ile Ala Glu Ile His
                20                  25                  30

Thr Ala Glu Ile
            35

<210> SEQ ID NO 13
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 13

Ala Val Xaa Glu Ile Gln Leu Met His Gln Xaa Ala Lys Trp Leu Asn
1               5                   10                  15

Ser Met Arg Arg Val Glu Trp Leu Arg Lys Lys Leu Gln Asp Val His
                20                  25                  30

Asn Phe

<210> SEQ ID NO 14
<211> LENGTH: 36
<212> TYPE: PRT
<213> ORGANISM: Homo sapiens

<400> SEQUENCE: 14

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Ile
            35

<210> SEQ ID NO 15
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (16)..(16)
<223> OTHER INFORMATION: Nle

<400> SEQUENCE: 15

Ser Glu Ile Gln Phe Xaa His Asn Leu Gly Lys His Leu Ser Ser Xaa
1               5                   10                  15

Glu Arg Val Glu Trp Leu Arg Lys Lys Leu Gln Asp Val His Asn Tyr
                20                  25                  30
```